US011497867B2

(12) United States Patent
Costella et al.

(10) Patent No.: US 11,497,867 B2
(45) Date of Patent: Nov. 15, 2022

(54) SMART NEBULIZER

(71) Applicant: TRUDELL MEDICAL INTERNATIONAL, London (CA)

(72) Inventors: Stephen Costella, London (CA); Andrew Dittmer, Woodstock (CA); Luke Kilroy, London (CA); Alanna Kirchner, London (CA); Robert Morton, London (CA); James N. Schmidt, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 269 days.

(21) Appl. No.: 15/705,943

(22) Filed: Sep. 15, 2017

(65) Prior Publication Data

US 2018/0161531 A1    Jun. 14, 2018

Related U.S. Application Data

(60) Provisional application No. 62/432,304, filed on Dec. 9, 2016.

(51) Int. Cl.
*A61M 16/00* (2006.01)
*A61M 15/00* (2006.01)
(Continued)

(52) U.S. Cl.
CPC ........ *A61M 16/0051* (2013.01); *A61M 11/02* (2013.01); *A61M 11/06* (2013.01);
(Continued)

(58) Field of Classification Search
CPC .............. A61M 16/0051; A61M 11/02; A61M 15/0086; A61M 15/009; A61M 15/0091;
(Continued)

(56) References Cited

U.S. PATENT DOCUMENTS

| 1,742,740 A | 1/1930 | Watters |
| 2,535,844 A | 12/1950 | Emerson |

(Continued)

FOREIGN PATENT DOCUMENTS

| AT | 2004202959 A1 | 7/2004 |
| AU | 29969/89 | 8/1990 |

(Continued)

OTHER PUBLICATIONS

PCT Notification of the International Search Report and Written Opinion of the International Search Authority dated Jan. 5, 2018, 10 pgs.

(Continued)

*Primary Examiner* — Elliot S Ruddie
(74) *Attorney, Agent, or Firm* — Crowell & Moring LLP

(57) ABSTRACT

A nebulizer system capable of identifying when activation has occurred and aerosol is being produced. The nebulizer system monitors the inhalation and exhalation flow generated by the patient and communicates proper breathing technique for optimal drug delivery. The nebulizer system may monitor air supply to the nebulizer to ensure it is within the working range and is producing, or is capable of producing, acceptable particle size and drug output rate. When a patient, caregiver or other user deposits or inserts medication into the nebulizer, the nebulizer system is able to identify the medication and determine the appropriate delivery methods required to properly administer the medication as well as output this information into a treatment log to ensure the patient is taking the proper medications. The system is able to measure the concentration of the medication and volume of the medication placed within the medication receptacle, e.g., bowl.

42 Claims, 42 Drawing Sheets

(51) Int. Cl.
    *A61M 11/06* (2006.01)
    *A61M 16/16* (2006.01)
    *A61M 11/02* (2006.01)
    *A61M 16/14* (2006.01)

(52) U.S. Cl.
    CPC .... *A61M 15/0021* (2014.02); *A61M 15/0086* (2013.01); *A61M 15/0091* (2013.01); *A61M 16/14* (2013.01); *A61M 16/161* (2014.02); *A61M 2016/0021* (2013.01); *A61M 2016/0027* (2013.01); *A61M 2016/0039* (2013.01); *A61M 2205/332* (2013.01); *A61M 2205/3327* (2013.01); *A61M 2205/3334* (2013.01); *A61M 2205/3358* (2013.01); *A61M 2205/3368* (2013.01); *A61M 2205/3375* (2013.01); *A61M 2205/3379* (2013.01); *A61M 2205/3569* (2013.01); *A61M 2205/3584* (2013.01); *A61M 2205/3592* (2013.01); *A61M 2205/505* (2013.01); *A61M 2205/581* (2013.01); *A61M 2205/582* (2013.01); *A61M 2205/583* (2013.01); *A61M 2230/63* (2013.01)

(58) Field of Classification Search
    CPC .......... A61M 16/14; A61M 2016/0039; A61M 2205/3327; A61M 2205/3331; A61M 2205/3334; A61M 2205/3379; A61M 2205/3382; A61M 2205/3386; A61M 2205/3584; A61M 2205/3546; A61M 2205/3553; A61M 2205/58; A61M 2205/581; A61M 2205/582; A61M 2205/583
    See application file for complete search history.

(56) References Cited

U.S. PATENT DOCUMENTS

| | | | |
|---|---|---|---|
| 2,882,026 A | 4/1959 | Eichelman | |
| 2,951,644 A | 9/1960 | Mahon et al. | |
| 3,001,524 A | 9/1961 | Maison et al. | |
| 3,172,406 A | 3/1965 | Bird et al. | |
| 3,269,665 A | 8/1966 | Cheney | |
| 3,467,092 A | 9/1969 | Bird et al. | |
| 3,490,697 A | 1/1970 | Best, Jr. | |
| 3,580,249 A | 5/1971 | Takaoka | |
| 3,584,621 A | 6/1971 | Bird et al. | |
| 3,630,196 A | 12/1971 | Bird et al. | |
| 3,658,059 A | 4/1972 | Steil | |
| 3,664,337 A | 5/1972 | Lindsey et al. | |
| 3,826,255 A | 7/1974 | Havstad et al. | |
| 3,838,686 A | 10/1974 | Szekely | |
| 3,874,379 A | 4/1975 | Enfield et al. | |
| 3,903,884 A | 9/1975 | Huston et al. | |
| 3,990,442 A | 11/1976 | Patneau | |
| 4,093,124 A | 6/1978 | Morane et al. | |
| 4,094,317 A | 6/1978 | Wasnich | |
| 4,106,503 A | 8/1978 | Rosenthal et al. | |
| 4,116,387 A | 9/1978 | Kremer, Jr. et al. | |
| 4,139,128 A | 2/1979 | Ewald | |
| 4,150,071 A | 4/1979 | Pecina | |
| 4,183,361 A | 1/1980 | Russo | |
| 4,198,969 A | 4/1980 | Virag | |
| 4,206,644 A | 6/1980 | Platt | |
| 4,210,140 A | 7/1980 | James et al. | |
| 4,210,155 A | 7/1980 | Grimes | |
| 4,251,033 A | 2/1981 | Rich et al. | |
| 4,253,468 A | 3/1981 | Lehmbeck | |
| 4,268,460 A | 5/1981 | Boiarski et al. | |
| 4,291,688 A | 9/1981 | Kistler | |
| 4,333,450 A | 6/1982 | Lester | |
| 4,413,784 A | 11/1983 | Dea | |
| 4,452,239 A | 6/1984 | Malem | |
| 4,456,179 A | 6/1984 | Kremer | |
| 4,470,412 A | 9/1984 | Nowacki et al. | |
| 4,484,577 A | 11/1984 | Sackner et al. | |
| 4,508,118 A | 4/1985 | Toth | |
| 4,509,688 A | 4/1985 | Gagne et al. | |
| 4,588,129 A | 5/1986 | Shanks | |
| 4,620,670 A | 11/1986 | Hughes | |
| 4,622,968 A | 11/1986 | Persson | |
| 4,627,432 A | 12/1986 | Newell et al. | |
| 4,649,911 A | 3/1987 | Knight | |
| 4,657,007 A | 4/1987 | Carlin et al. | |
| 4,674,491 A | 6/1987 | Brugger et al. | |
| 4,677,975 A | 7/1987 | Edgar et al. | |
| 4,746,067 A | 5/1988 | Svoboda | |
| 4,758,224 A | 7/1988 | Siposs | |
| 4,792,097 A | 12/1988 | Kremer, Jr. et al. | |
| 4,809,692 A | 3/1989 | Nowacki et al. | |
| 4,832,015 A | 5/1989 | Nowacki et al. | |
| 4,911,157 A | 3/1990 | Miller | |
| 4,951,659 A | 8/1990 | Weiler et al. | |
| 4,971,049 A | 11/1990 | Rotariu | |
| 4,981,158 A | 1/1991 | Brondolino et al. | |
| 4,984,158 A * | 1/1991 | Hillsman | A61B 5/091 128/200.14 |
| 5,012,803 A | 5/1991 | Foley et al. | |
| 5,012,804 A | 5/1991 | Foley et al. | |
| 5,020,527 A | 6/1991 | Dessertine | |
| 5,020,530 A | 6/1991 | Miller | |
| 5,042,467 A | 8/1991 | Foley | |
| 5,054,477 A | 10/1991 | Terada et al. | |
| 5,054,478 A | 10/1991 | Grychowski et al. | |
| 5,078,131 A | 1/1992 | Foley | |
| 5,086,765 A | 2/1992 | Levine | |
| 5,165,392 A | 11/1992 | Small | |
| 5,167,506 A | 12/1992 | Kilis et al. | |
| 5,170,782 A | 12/1992 | Kocinski | |
| 5,209,225 A | 5/1993 | Glenn | |
| 5,235,969 A | 8/1993 | Bellm | |
| 5,241,954 A | 9/1993 | Glenn | |
| 5,277,175 A | 1/1994 | Riggs et al. | |
| 5,280,784 A | 1/1994 | Kohler | |
| 5,284,133 A | 2/1994 | Burns et al. | |
| 5,299,565 A | 4/1994 | Brown | |
| 5,301,662 A | 4/1994 | Bagwell et al. | |
| 5,301,663 A | 4/1994 | Small, Jr. | |
| 5,309,900 A | 5/1994 | Knoch et al. | |
| 5,312,046 A | 5/1994 | Knoch et al. | |
| 5,312,281 A | 5/1994 | Takahashi et al. | |
| 5,318,015 A | 6/1994 | Mansson et al. | |
| 5,331,953 A | 7/1994 | Andersson et al. | |
| 5,333,106 A | 7/1994 | Lanpher et al. | |
| 5,337,926 A | 8/1994 | Drobish et al. | |
| 5,349,947 A | 9/1994 | Newhouse et al. | |
| 5,363,842 A * | 11/1994 | Mishelevich | A61B 8/0875 128/200.14 |
| 5,383,470 A | 1/1995 | Kolbly | |
| 5,385,140 A | 1/1995 | Smith | |
| 5,392,648 A | 2/1995 | Robertson | |
| 5,398,714 A | 3/1995 | Price | |
| 5,427,089 A | 6/1995 | Kraemer | |
| 5,431,154 A | 7/1995 | Seigel et al. | |
| 5,458,136 A | 10/1995 | Jaser et al. | |
| 5,461,695 A | 10/1995 | Knoch | |
| 5,477,849 A | 12/1995 | Fry | |
| 5,479,920 A | 1/1996 | Piper et al. | |
| 5,487,378 A | 1/1996 | Robertson et al. | |
| 5,497,765 A | 3/1996 | Praud et al. | |
| 5,503,139 A | 4/1996 | McMahon et al. | |
| 5,505,192 A | 4/1996 | Samiotes et al. | |
| 5,505,193 A | 4/1996 | Ballini et al. | |
| 5,505,195 A | 4/1996 | Wolf et al. | |
| 5,511,538 A | 4/1996 | Haber et al. | |
| 5,511,539 A | 4/1996 | Lien | |
| 5,515,842 A | 5/1996 | Ramseyer et al. | |
| 5,520,166 A | 5/1996 | Ritson et al. | |
| 5,522,380 A | 6/1996 | Dwork | |
| 5,533,497 A | 7/1996 | Ryder | |
| 5,533,501 A | 7/1996 | Denyer | |
| 5,544,647 A | 8/1996 | Jewett et al. | |
| 5,549,102 A | 8/1996 | Lintl et al. | |

(56) References Cited

U.S. PATENT DOCUMENTS

| | | |
|---|---|---|
| 5,570,682 A | 11/1996 | Johnson |
| 5,582,162 A | 12/1996 | Petersson |
| 5,584,285 A | 12/1996 | Salter et al. |
| 5,586,550 A | 12/1996 | Ivri et al. |
| 5,598,839 A | 2/1997 | Niles et al. |
| 5,613,489 A | 3/1997 | Miller et al. |
| 5,617,844 A | 4/1997 | King |
| 5,622,162 A | 4/1997 | Johansson et al. |
| 5,630,409 A | 5/1997 | Bono et al. |
| 5,645,049 A | 7/1997 | Foley et al. |
| 5,687,912 A | 11/1997 | Denyer |
| 5,701,886 A | 12/1997 | Ryatt |
| 5,704,344 A | 1/1998 | Cole |
| 5,740,793 A | 4/1998 | Hodson et al. |
| 5,743,250 A | 4/1998 | Gonda et al. |
| 5,752,505 A | 5/1998 | Ohki et al. |
| 5,758,638 A | 6/1998 | Kreamer |
| 5,765,553 A | 6/1998 | Richards et al. |
| 5,792,057 A | 8/1998 | Rubsamen et al. |
| 5,794,612 A | 8/1998 | Wachter et al. |
| 5,803,078 A | 9/1998 | Brauner |
| 5,809,997 A | 9/1998 | Wolf |
| 5,816,240 A | 10/1998 | Komesaroff |
| 5,819,726 A | 10/1998 | Rubsamen et al. |
| 5,823,179 A * | 10/1998 | Grychowski .......... A61M 11/06 128/200.18 |
| 5,839,429 A | 11/1998 | Marnfeldt et al. |
| 5,848,588 A | 12/1998 | Foley et al. |
| 5,865,172 A | 2/1999 | Butler et al. |
| 5,875,774 A | 3/1999 | Clementi et al. |
| 5,881,718 A | 3/1999 | Mortensen et al. |
| 5,890,490 A | 4/1999 | Aylsworth |
| 5,899,201 A | 5/1999 | Schultz et al. |
| 5,937,852 A | 8/1999 | Butler et al. |
| 5,954,049 A | 9/1999 | Foley et al. |
| 5,988,160 A | 11/1999 | Foley et al. |
| 6,026,807 A | 2/2000 | Puderbaugh et al. |
| 6,039,042 A | 3/2000 | Sladek |
| 6,033,841 A | 4/2000 | Verdun et al. |
| 6,044,841 A | 4/2000 | Verdun et al. |
| 6,073,628 A | 6/2000 | Butler et al. |
| 6,116,233 A | 9/2000 | Denyer et al. |
| 6,116,239 A | 9/2000 | Volgyesi |
| 6,129,080 A | 10/2000 | Pitcher et al. |
| 6,131,568 A | 10/2000 | Denyer et al. |
| 6,131,570 A | 10/2000 | Schuster et al. |
| 6,138,669 A | 10/2000 | Rocci, Jr. et al. |
| 6,148,815 A | 11/2000 | Wolf |
| 6,176,237 B1 | 1/2001 | Wunderlich et al. |
| 6,179,164 B1 | 1/2001 | Fuchs |
| 6,192,876 B1 | 2/2001 | Denyer et al. |
| 6,202,642 B1 | 3/2001 | McKinnon et al. |
| 6,223,745 B1 | 5/2001 | Hammarlund et al. |
| 6,230,704 B1 | 5/2001 | Durkin et al. |
| 6,234,167 B1 | 5/2001 | Cox et al. |
| 6,237,589 B1 | 5/2001 | Denyer et al. |
| 6,253,767 B1 | 7/2001 | Mantz |
| 6,293,279 B1 | 9/2001 | Schmidt et al. |
| 6,338,443 B1 | 1/2002 | Piper |
| 6,345,617 B1 | 2/2002 | Engelbreth et al. |
| 6,349,719 B2 | 2/2002 | Gonda |
| 6,358,058 B1 | 3/2002 | Strupat et al. |
| 6,435,177 B1 | 8/2002 | Schmidt et al. |
| 6,450,163 B1 | 9/2002 | Blacker et al. |
| 6,470,885 B1 | 10/2002 | Blue et al. |
| 6,481,435 B2 | 11/2002 | Hochrainer et al. |
| 6,513,519 B2 | 2/2003 | Gallem |
| 6,543,448 B1 | 4/2003 | Smith et al. |
| 6,546,927 B2 | 4/2003 | Litherland et al. |
| 6,554,201 B2 | 4/2003 | Klimowicz et al. |
| 6,557,549 B2 | 5/2003 | Schmidt et al. |
| 6,578,571 B1 | 6/2003 | Watt |
| 6,584,971 B1 | 7/2003 | Denyer et al. |
| 6,595,203 B1 | 7/2003 | Bird |
| 6,606,992 B1 | 8/2003 | Schuler et al. |
| 6,612,303 B1 | 9/2003 | Grychowski et al. |
| 6,644,304 B2 | 11/2003 | Grychowski et al. |
| 6,651,651 B1 | 11/2003 | Bonney et al. |
| 6,679,250 B2 | 1/2004 | Walker et al. |
| 6,698,421 B2 | 3/2004 | Attolini |
| 6,708,688 B1 | 3/2004 | Rubin et al. |
| 6,748,945 B2 | 6/2004 | Grychowski et al. |
| 6,796,513 B2 | 9/2004 | Fraccaroli |
| 6,823,862 B2 | 11/2004 | McNaughton |
| 6,839,604 B2 | 1/2005 | Godfrey et al. |
| 6,848,443 B2 | 2/2005 | Schmidt et al. |
| 6,857,427 B2 | 2/2005 | Ziegler et al. |
| 6,880,722 B2 | 4/2005 | Anderson et al. |
| 6,883,517 B2 | 4/2005 | Halamish |
| 6,885,684 B2 | 4/2005 | Ichino |
| 6,899,684 B2 | 5/2005 | Mault et al. |
| 6,904,907 B2 | 6/2005 | Speldrich et al. |
| 6,904,908 B2 | 6/2005 | Bruce et al. |
| 6,929,003 B2 | 8/2005 | Blacker et al. |
| 6,932,083 B2 | 8/2005 | Jones et al. |
| 6,934,220 B1 | 8/2005 | Cruitt et al. |
| 6,958,691 B1 | 10/2005 | Anderson et al. |
| 6,983,652 B2 | 1/2006 | Blakley et al. |
| 6,990,975 B1 | 1/2006 | Jones et al. |
| 6,994,083 B2 | 2/2006 | Foley et al. |
| 7,009,517 B2 | 3/2006 | Wood |
| 7,013,896 B2 | 3/2006 | Schmidt |
| 7,036,505 B2 | 5/2006 | Bacon et al. |
| 7,051,731 B1 | 5/2006 | Rogerson |
| 7,072,738 B2 | 7/2006 | Bonney et al. |
| 7,080,643 B2 | 7/2006 | Grychowski et al. |
| 7,089,786 B2 | 8/2006 | Walker |
| 7,091,864 B2 | 8/2006 | Veitch et al. |
| 7,131,439 B2 | 11/2006 | Blacker et al. |
| 7,131,440 B2 | 11/2006 | Sonntag |
| 7,151,456 B2 | 12/2006 | Godfrey |
| 7,159,533 B1 | 1/2007 | Redd et al. |
| 7,191,777 B2 | 3/2007 | Brand et al. |
| 7,198,172 B2 | 4/2007 | Harvey et al. |
| 7,201,164 B2 | 4/2007 | Grychowski et al. |
| 7,201,165 B2 | 4/2007 | Bruce et al. |
| 7,201,167 B2 | 4/2007 | Fink et al. |
| 7,233,228 B2 | 6/2007 | Lintell |
| 7,252,085 B2 | 8/2007 | Kunschir |
| 7,255,106 B2 | 8/2007 | Gallem et al. |
| 7,261,102 B2 | 8/2007 | Barney et al. |
| 7,267,120 B2 | 9/2007 | Rustad et al. |
| 7,270,123 B2 | 9/2007 | Grychowski et al. |
| 7,290,541 B2 | 11/2007 | Ivri et al. |
| 7,331,340 B2 | 2/2008 | Barney |
| 7,331,343 B2 | 2/2008 | Schmidt |
| 7,337,776 B2 | 3/2008 | Fishman et al. |
| 7,383,837 B2 | 6/2008 | Robertson et al. |
| 7,424,888 B2 | 6/2008 | Harvey et al. |
| 7,404,400 B2 | 7/2008 | Lulla et al. |
| RE40,591 E | 12/2008 | Denyer |
| 7,458,372 B2 | 12/2008 | Feiner et al. |
| 7,481,213 B2 | 1/2009 | Childers |
| 7,495,546 B2 | 2/2009 | Lintell |
| 7,559,322 B2 | 7/2009 | Foley et al. |
| 7,568,480 B2 | 8/2009 | Foley et al. |
| 7,581,718 B1 | 9/2009 | Chang |
| 7,597,099 B2 | 10/2009 | Jones et al. |
| 7,600,511 B2 | 10/2009 | Power et al. |
| 7,621,270 B2 | 11/2009 | Morris et al. |
| 7,634,995 B2 | 12/2009 | Grychowski et al. |
| 7,661,423 B2 | 2/2010 | Brand et al. |
| 7,730,847 B1 | 6/2010 | Redd et al. |
| 7,748,382 B2 | 7/2010 | Denyer et al. |
| 7,748,385 B2 | 7/2010 | Lieberman et al. |
| 7,758,886 B2 | 7/2010 | Jauernig et al. |
| 7,779,841 B2 | 8/2010 | Dunsmore et al. |
| 7,819,116 B2 | 10/2010 | Brand et al. |
| 7,837,648 B2 | 11/2010 | Blair et al. |
| 7,841,335 B2 | 11/2010 | Harrington et al. |
| 7,946,291 B2 | 5/2011 | Fink et al. |
| 7,954,487 B2 | 6/2011 | Grychowski et al. |
| 7,971,588 B2 | 7/2011 | Fink et al. |
| 7,984,712 B2 | 7/2011 | Soliman et al. |

(56) References Cited

U.S. PATENT DOCUMENTS

| | | |
|---|---|---|
| 8,113,194 B2 | 2/2012 | Boehm et al. |
| 8,165,892 B2 | 4/2012 | Carter et al. |
| 8,261,738 B2 * | 9/2012 | Denyer ................ A61M 11/005 |
| | | 128/203.14 |
| 8,333,190 B2 | 12/2012 | Addington et al. |
| 8,335,567 B2 | 12/2012 | Tehrani et al. |
| 8,336,545 B2 | 12/2012 | Fink et al. |
| 8,342,171 B2 | 1/2013 | Boehm et al. |
| 8,347,878 B2 | 1/2013 | Schuschnig et al. |
| 8,397,712 B2 | 3/2013 | Foley et al. |
| 8,403,861 B2 | 3/2013 | Williams et al. |
| D680,214 S | 4/2013 | Eckstein et al. |
| 8,424,517 B2 | 4/2013 | Sutherland et al. |
| 8,464,707 B2 | 6/2013 | Jongejan et al. |
| 8,474,448 B2 | 7/2013 | Oi et al. |
| 8,534,277 B2 | 9/2013 | Stenzler et al. |
| 8,550,067 B2 | 10/2013 | Bruce et al. |
| 8,550,069 B2 | 10/2013 | Alelov |
| 8,596,264 B2 | 12/2013 | Sommer |
| 8,607,783 B2 * | 12/2013 | Takei ..................... B05B 11/02 |
| | | 128/200.23 |
| 8,616,195 B2 | 12/2013 | Power et al. |
| 8,668,901 B2 | 3/2014 | Muellinger et al. |
| 8,707,950 B1 | 4/2014 | Rubin |
| 8,738,395 B2 | 5/2014 | Hyde et al. |
| 8,740,808 B2 | 6/2014 | Curti et al. |
| 8,807,131 B1 | 8/2014 | Tunnell et al. |
| 8,844,520 B2 | 9/2014 | Foley et al. |
| 9,022,023 B2 | 5/2015 | Korneff |
| 9,035,765 B2 | 5/2015 | Engelhard et al. |
| 9,072,321 B2 | 7/2015 | Liu |
| 9,072,846 B2 | 7/2015 | Helmlinger |
| 9,108,211 B2 | 8/2015 | Ivri et al. |
| 9,155,846 B2 | 10/2015 | Kern |
| 9,242,056 B2 | 1/2016 | Andersen et al. |
| D757,926 S | 5/2016 | Van Sickle et al. |
| 9,352,107 B2 | 5/2016 | Von Hollen et al. |
| 9,364,618 B2 | 6/2016 | Blacker et al. |
| 9,427,534 B2 | 8/2016 | Bruin et al. |
| 9,452,317 B2 | 9/2016 | Arkush |
| 9,468,729 B2 | 10/2016 | Sutherland et al. |
| D771,800 S | 11/2016 | Engelhard et al. |
| 9,539,408 B2 | 1/2017 | Pevler |
| 9,764,104 B2 | 9/2017 | Gumaste et al. |
| 9,782,550 B2 | 10/2017 | Morrison et al. |
| 9,782,551 B2 | 10/2017 | Morrison et al. |
| 9,956,359 B2 | 5/2018 | Nikander et al. |
| 9,993,602 B2 | 6/2018 | Davidson et al. |
| 10,016,567 B2 | 7/2018 | Denyer et al. |
| 10,019,555 B2 | 7/2018 | Manice et al. |
| 10,092,712 B2 | 10/2018 | Power et al. |
| 10,130,779 B2 | 11/2018 | Denyer et al. |
| 10,220,166 B2 | 3/2019 | Van Sickle et al. |
| 10,258,754 B2 | 4/2019 | Nightingale et al. |
| 10,300,239 B2 | 5/2019 | Brand et al. |
| 10,363,384 B2 | 7/2019 | Dyche et al. |
| 10,406,302 B2 | 9/2019 | Andrade et al. |
| 10,406,303 B2 | 9/2019 | Anandhakrishnan |
| 10,463,813 B2 | 11/2019 | Vasandani et al. |
| 10,603,450 B2 | 3/2020 | Sutherland |
| 10,674,960 B2 | 6/2020 | Fridman |
| 10,751,500 B2 | 8/2020 | Lee et al. |
| 10,786,638 B2 | 9/2020 | Alizoti et al. |
| D912,072 S | 3/2021 | Liu et al. |
| 10,953,168 B2 | 3/2021 | Biswas et al. |
| 2002/0020762 A1 | 2/2002 | Selzer et al. |
| 2002/0036776 A1 * | 3/2002 | Shimaoka .......... G01N 15/0211 |
| | | 356/336 |
| 2002/0073991 A1 | 6/2002 | Conda |
| 2002/0090601 A1 | 7/2002 | Strupat et al. |
| 2002/0104531 A1 | 8/2002 | Malone |
| 2002/0157663 A1 * | 10/2002 | Blacker ................ A61M 11/007 |
| | | 128/200.21 |
| 2003/0075171 A1 | 4/2003 | Jones et al. |
| 2003/0089366 A1 | 5/2003 | Sommer |
| 2003/0136399 A1 | 7/2003 | Foley et al. |
| 2003/0159694 A1 | 8/2003 | McNaughton |
| 2003/0197068 A1 | 10/2003 | Abate |
| 2003/0205229 A1 | 11/2003 | Crockford et al. |
| 2003/0209238 A1 | 11/2003 | Peters |
| 2004/0007231 A1 | 1/2004 | Zhou |
| 2004/0055595 A1 | 3/2004 | Noymer et al. |
| 2005/0039741 A1 | 2/2005 | Gallem et al. |
| 2005/0066968 A1 | 3/2005 | Shofner et al. |
| 2005/0087178 A1 | 4/2005 | Milton |
| 2005/0145243 A1 | 7/2005 | Trombi |
| 2005/0183718 A1 | 8/2005 | Wuttke et al. |
| 2006/0005834 A1 | 1/2006 | Aylsworth et al. |
| 2006/0011196 A2 | 1/2006 | Gallem et al. |
| 2006/0089545 A1 | 4/2006 | Ratjen et al. |
| 2006/0157052 A1 | 7/2006 | Foley et al. |
| 2006/0178394 A1 | 8/2006 | Staniforth et al. |
| 2007/0017506 A1 | 1/2007 | Bell et al. |
| 2007/0023036 A1 | 2/2007 | Grychowski et al. |
| 2007/0068513 A1 | 3/2007 | Kreutzmann et al. |
| 2007/0125372 A1 | 6/2007 | Chen |
| 2007/0204864 A1 | 9/2007 | Grychowski et al. |
| 2007/0235028 A1 | 10/2007 | Bruce et al. |
| 2007/0289590 A1 | 12/2007 | Kreutzmann et al. |
| 2008/0011292 A1 | 1/2008 | Sugita et al. |
| 2008/0083407 A1 | 4/2008 | Grychowski et al. |
| 2008/0230053 A1 | 9/2008 | Kraft |
| 2008/0257345 A1 | 10/2008 | Snyder et al. |
| 2009/0025718 A1 * | 1/2009 | Denyer ................ A61M 11/005 |
| | | 128/203.14 |
| 2009/0178672 A1 | 7/2009 | Mullinger et al. |
| 2009/0194104 A1 | 8/2009 | Van Sickle |
| 2009/0272820 A1 | 11/2009 | Foley et al. |
| 2009/0314292 A1 | 12/2009 | Overfield et al. |
| 2010/0191192 A1 | 7/2010 | Prasad et al. |
| 2010/0192948 A1 | 8/2010 | Sutherland et al. |
| 2010/0196483 A1 | 8/2010 | Muellinger et al. |
| 2010/0250280 A1 | 9/2010 | Sutherland |
| 2010/0252036 A1 | 10/2010 | Sutherland et al. |
| 2010/0324439 A1 | 12/2010 | Davenport |
| 2011/0137290 A1 | 6/2011 | Flickinger |
| 2011/0180563 A1 | 7/2011 | Fitchett et al. |
| 2011/0209700 A1 | 9/2011 | Kreutzmann et al. |
| 2011/0226237 A1 | 9/2011 | Morrison |
| 2011/0226242 A1 | 9/2011 | Von Hollen et al. |
| 2012/0012106 A1 | 1/2012 | Bari |
| 2012/0165693 A1 | 6/2012 | Williams et al. |
| 2012/0240923 A1 * | 9/2012 | Denyer ................ A61M 15/00 |
| | | 128/202.22 |
| 2012/0266872 A1 | 10/2012 | Tanaka et al. |
| 2012/0285236 A1 | 11/2012 | Haartsen et al. |
| 2012/0285447 A1 | 11/2012 | Schipper et al. |
| 2012/0291779 A1 | 11/2012 | Haartsen et al. |
| 2012/0312302 A1 | 12/2012 | Cardelius et al. |
| 2013/0008436 A1 * | 1/2013 | Von Hollen ...... A61M 15/0005 |
| | | 128/200.14 |
| 2013/0034534 A1 | 2/2013 | Kroneberg et al. |
| 2013/0037020 A1 | 2/2013 | Tanaka et al. |
| 2013/0053719 A1 | 2/2013 | Wekell |
| 2013/0092158 A1 | 4/2013 | Levy et al. |
| 2013/0151162 A1 | 6/2013 | Harris et al. |
| 2013/0186392 A1 | 7/2013 | Haartsen et al. |
| 2013/0213115 A1 * | 8/2013 | Chu ......................... B07B 7/00 |
| | | 73/28.04 |
| 2013/0247903 A1 | 9/2013 | Foley et al. |
| 2014/0000598 A1 | 1/2014 | Sutherland et al. |
| 2014/0000599 A1 | 1/2014 | Dyche et al. |
| 2014/0106324 A1 | 4/2014 | Adams et al. |
| 2014/0182584 A1 | 7/2014 | Sutherland et al. |
| 2014/0257126 A1 | 9/2014 | Vink et al. |
| 2014/0261474 A1 | 9/2014 | Gonda |
| 2014/0318534 A1 | 10/2014 | Engelbreth |
| 2014/0352690 A1 | 12/2014 | Kolb et al. |
| 2015/0011906 A1 | 1/2015 | Wallach |
| 2015/0020804 A1 * | 1/2015 | Van Der Mark ... A61M 16/026 |
| | | 128/203.14 |
| 2015/0059739 A1 | 3/2015 | Aslam |
| 2015/0061867 A1 | 3/2015 | Engelhard et al. |
| 2015/0099994 A1 | 4/2015 | Spencer et al. |

(56) References Cited

U.S. PATENT DOCUMENTS

| | | |
|---|---|---|
| 2015/0100276 A1 | 4/2015 | Huang et al. |
| 2015/0100335 A1 | 4/2015 | Englehard et al. |
| 2015/0112707 A1 | 4/2015 | Manice et al. |
| 2015/0122248 A1 | 5/2015 | Power et al. |
| 2015/0122261 A1 | 5/2015 | Pettit |
| 2015/0164373 A1 | 6/2015 | Davis et al. |
| 2015/0174348 A1 | 6/2015 | Tunnell et al. |
| 2015/0174349 A1 | 6/2015 | Tunnell et al. |
| 2015/0231341 A1 | 8/2015 | Korneff |
| 2015/0235548 A1 | 8/2015 | Engelhard et al. |
| 2015/0283337 A1 | 10/2015 | Adams et al. |
| 2015/0352281 A1 | 10/2015 | Pfrang |
| 2016/0045681 A1 | 2/2016 | Cheatham, III et al. |
| 2016/0045682 A1 | 2/2016 | Boyden et al. |
| 2016/0045683 A1 | 2/2016 | Cheatham, III et al. |
| 2016/0045685 A1 | 2/2016 | Hyde et al. |
| 2016/0051776 A1 | 2/2016 | Von Hollen |
| 2016/0058960 A1* | 3/2016 | Papania ............ A61B 1/00195 600/103 |
| 2016/0082208 A1 | 3/2016 | Ballam et al. |
| 2016/0106375 A1 | 4/2016 | Leydon |
| 2016/0106935 A1 | 4/2016 | Sezan et al. |
| 2016/0129182 A1 | 5/2016 | Schuster et al. |
| 2016/0129206 A1 | 5/2016 | Engelbreth |
| 2016/0136366 A1 | 5/2016 | Bennett |
| 2016/0136367 A1 | 5/2016 | Varney |
| 2016/0144141 A1 | 5/2016 | Biswas et al. |
| 2016/0144142 A1 | 5/2016 | Baker et al. |
| 2016/0158467 A1 | 6/2016 | Porteous |
| 2016/0166766 A1 | 6/2016 | Schuster et al. |
| 2016/0184535 A1 | 6/2016 | Edwards et al. |
| 2016/0193436 A1 | 7/2016 | Khasawneh |
| 2016/0213868 A1 | 7/2016 | Khasawneh et al. |
| 2016/0228656 A1 | 8/2016 | Vasandani et al. |
| 2016/0250426 A1* | 9/2016 | Morrison ............ A61M 15/0085 128/200.16 |
| 2016/0256639 A1 | 9/2016 | Van Sickle et al. |
| 2016/0287139 A1 | 10/2016 | Luttrell |
| 2016/0314256 A1 | 10/2016 | Su et al. |
| 2016/0325058 A1 | 11/2016 | Samson et al. |
| 2016/0331917 A1 | 11/2016 | Bennett et al. |
| 2016/0339187 A1* | 11/2016 | Smaldone ............ A61M 11/005 |
| 2016/0339190 A1 | 11/2016 | Morrison et al. |
| 2016/0346489 A1 | 12/2016 | Finke et al. |
| 2016/0354562 A1 | 12/2016 | Morrison |
| 2017/0020776 A1 | 1/2017 | Khasawneh et al. |
| 2017/0113006 A1 | 4/2017 | Pevler |
| 2017/0127945 A1 | 5/2017 | Reed |
| 2017/0173282 A1 | 6/2017 | O'Sullivan et al. |
| 2017/0296772 A1* | 10/2017 | Costella ................ A61M 11/06 |
| 2017/0333645 A1 | 11/2017 | Alizoti et al. |
| 2017/0333661 A1 | 11/2017 | Bennett et al. |
| 2018/0008789 A1 | 1/2018 | Alizoti et al. |
| 2018/0008790 A1* | 1/2018 | Costella ............ A61M 16/0006 |
| 2018/0036199 A1* | 2/2018 | Bougatef ............ A61H 23/02 |
| 2018/0140252 A1 | 5/2018 | Luxon et al. |
| 2018/0161531 A1 | 6/2018 | Costella et al. |
| 2018/0177959 A1 | 6/2018 | McLoughlin et al. |
| 2018/0264207 A1 | 9/2018 | Von Hollen et al. |
| 2018/0272080 A1 | 9/2018 | Porter et al. |
| 2018/0272081 A1 | 9/2018 | Porter et al. |
| 2018/0296124 A1 | 10/2018 | Karakaya et al. |
| 2018/0369509 A1 | 12/2018 | Power et al. |
| 2019/0038854 A1 | 2/2019 | Fuchs et al. |
| 2019/0298941 A1 | 10/2019 | Collins |
| 2020/0038611 A1 | 2/2020 | Isaza |
| 2020/0069893 A1 | 3/2020 | Vasandani et al. |
| 2020/0086069 A1 | 3/2020 | Riebe et al. |
| 2020/0147327 A1 | 5/2020 | Krasnow |
| 2020/0187556 A1 | 6/2020 | Raichman |
| 2020/0188613 A1 | 6/2020 | Van Sickle et al. |
| 2020/0315260 A1 | 10/2020 | Hubbard |
| 2020/0345588 A1 | 11/2020 | Merrell et al. |
| 2021/0008304 A1 | 1/2021 | Marcoz et al. |
| 2021/0046259 A1 | 2/2021 | Hasegawa et al. |
| 2021/0052225 A1 | 2/2021 | Shetty et al. |
| 2021/0069433 A1 | 3/2021 | Wang et al. |
| 2021/0077056 A1 | 3/2021 | Matsumoto et al. |

FOREIGN PATENT DOCUMENTS

| | | |
|---|---|---|
| CA | 2 607 458 A1 | 11/2006 |
| DE | 2804852 A1 | 8/1978 |
| DE | 8703534 U1 | 8/1987 |
| DE | 199 02 847 C1 | 5/2000 |
| DE | 199 53 317 C1 | 2/2001 |
| DE | 102010024912 B4 | 2/2013 |
| EP | 0 261 649 B2 | 9/1987 |
| EP | 0 281 650 A1 | 9/1988 |
| EP | 0 414 536 A2 | 2/1991 |
| EP | 0 281 650 B1 | 3/1992 |
| EP | 0 514 085 A1 | 11/1992 |
| EP | 0 587 380 | 3/1993 |
| EP | 0387222 B1 | 7/1993 |
| EP | 0 601 708 A2 | 6/1994 |
| EP | 0 641 570 A1 | 3/1995 |
| EP | 0 711 609 A3 | 7/1995 |
| EP | 0 786 263 B1 | 1/1997 |
| EP | 0824023 A1 | 2/1998 |
| EP | 0617628 B1 | 5/1998 |
| EP | 0 855 224 B1 | 7/1998 |
| EP | 0 938 906 | 3/1999 |
| EP | 0 855 224 A2 | 7/1999 |
| EP | 0 601 708 B1 | 3/2000 |
| EP | 1 439 875 B1 | 10/2002 |
| EP | 1338296 A1 | 8/2003 |
| EP | 1 673 124 B1 | 9/2004 |
| EP | 1330283 B1 | 9/2006 |
| EP | 2 548 599 A1 | 2/2011 |
| EP | 1993642 B1 | 1/2012 |
| EP | 1670533 B1 | 7/2012 |
| EP | 2300083 B1 | 5/2013 |
| EP | 2609954 A2 | 7/2013 |
| EP | 2376156 B1 | 1/2014 |
| EP | 2859906 A1 | 4/2015 |
| EP | 2868339 A1 | 5/2015 |
| EP | 2563436 B1 | 10/2015 |
| EP | 2512566 B1 | 5/2016 |
| EP | 1613214 B1 | 10/2016 |
| EP | 3053620 A3 | 10/2016 |
| EP | 3097937 A1 | 11/2016 |
| EP | 2638925 B1 | 4/2017 |
| EP | 2 758 111 B1 | 9/2017 |
| EP | 3219089 B1 | 3/2019 |
| EP | 3569276 A1 | 11/2019 |
| EP | 2020103517 A4 | 1/2021 |
| EP | 3 782 682 A1 | 2/2021 |
| EP | 3 368 114 B1 | 3/2021 |
| EP | 3 583 899 B1 | 3/2021 |
| EP | 3 653 247 B1 | 3/2021 |
| FR | 1 070 292 | 7/1954 |
| FR | 93306974.2 | 3/1993 |
| FR | 2 763 507 A1 | 11/1998 |
| GB | 497 530 | 12/1939 |
| GB | 675524 | 7/1952 |
| GB | 2 253 200 A | 9/1992 |
| GB | 2 299 512 A | 10/1996 |
| GB | 2 310 607 A | 9/1997 |
| GB | 2406283 A | 3/2005 |
| GB | 2479953 A | 2/2011 |
| GB | 2490770 A | 11/2012 |
| GB | 2512047 A | 9/2014 |
| GB | 2479953 B | 4/2015 |
| JP | A-2011-92418 | 5/2011 |
| JP | A-2016-533245 | 10/2016 |
| WO | 88/03419 A1 | 5/1988 |
| WO | 90/09203 | 8/1990 |
| WO | WO9010470 A1 | 9/1990 |
| WO | WO 92/15354 | 2/1992 |
| WO | WO9207599 A1 | 5/1992 |
| WO | WO9312823 A2 | 7/1993 |
| WO | 94/17753 A1 | 8/1994 |
| WO | WO9507723 A1 | 2/1995 |
| WO | WO9522365 A1 | 8/1995 |

(56) References Cited

FOREIGN PATENT DOCUMENTS

| | | |
|---|---|---|
| WO | WO 1996/037249 A1 | 11/1996 |
| WO | WO9729799 A2 | 8/1997 |
| WO | 98/26828 A2 | 6/1998 |
| WO | WO 1998/033433 A1 | 8/1998 |
| WO | 98/41265 A1 | 9/1998 |
| WO | 98/44974 | 10/1998 |
| WO | WO9911310 A1 | 3/1999 |
| WO | 99/40959 A1 | 8/1999 |
| WO | 99/53982 | 10/1999 |
| WO | 00/59565 | 10/2000 |
| WO | WO0205879 A1 | 1/2002 |
| WO | WO0209574 A2 | 2/2002 |
| WO | WO02058771 A1 | 8/2002 |
| WO | WO03020349 A2 | 3/2003 |
| WO | WO03063937 A1 | 8/2003 |
| WO | WO03092576 A2 | 11/2003 |
| WO | WO03107523 A1 | 12/2003 |
| WO | WO2005042076 A1 | 5/2005 |
| WO | WO2005074455 A2 | 8/2005 |
| WO | WO2006123956 A1 | 11/2006 |
| WO | WO2007101438 A1 | 9/2007 |
| WO | WO2008112353 A2 | 9/2008 |
| WO | WO 2008/130658 A1 | 10/2008 |
| WO | WO2009022139 A1 | 2/2009 |
| WO | WO2010023591 A2 | 3/2010 |
| WO | WO2010023591 A3 | 3/2010 |
| WO | WO2010110682 A1 | 9/2010 |
| WO | WO2010114392 A1 | 10/2010 |
| WO | WO2011003017 A1 | 1/2011 |
| WO | WO2011073806 A1 | 6/2011 |
| WO | WO2011083377 A1 | 7/2011 |
| WO | WO2011089486 A1 | 7/2011 |
| WO | WO2011089489 A1 | 7/2011 |
| WO | WO2011089490 A1 | 7/2011 |
| WO | WO2011130183 A2 | 10/2011 |
| WO | WO2011130583 A2 | 10/2011 |
| WO | WO 2011/135915 A1 | 11/2011 |
| WO | WO2011135353 A1 | 11/2011 |
| WO | WO 2011/158715 A1 | 12/2011 |
| WO | WO 2011/158716 A1 | 12/2011 |
| WO | WO2012038861 A1 | 3/2012 |
| WO | WO2012064540 A2 | 5/2012 |
| WO | WO2012173992 A1 | 12/2012 |
| WO | WO 2013/013852 A1 | 1/2013 |
| WO | WO2013028705 A2 | 2/2013 |
| WO | WO2013042002 A1 | 3/2013 |
| WO | WO2013043063 A1 | 3/2013 |
| WO | WO2013061240 A1 | 5/2013 |
| WO | WO2013061248 A1 | 5/2013 |
| WO | WO 2013/099397 A1 | 7/2013 |
| WO | WO 2013/099398 A1 | 7/2013 |
| WO | WO 2013/099399 A1 | 7/2013 |
| WO | WO2013098334 A1 | 7/2013 |
| WO | WO2013124624 A1 | 8/2013 |
| WO | WO2014004437 A1 | 1/2014 |
| WO | WO2014033229 A1 | 3/2014 |
| WO | WO 2014/068387 A1 | 5/2014 |
| WO | WO2014147550 A1 | 9/2014 |
| WO | WO2014202923 A1 | 12/2014 |
| WO | WO2014204511 A3 | 12/2014 |
| WO | WO2015002652 A1 | 1/2015 |
| WO | WO2015004554 A1 | 1/2015 |
| WO | WO2015004559 A2 | 1/2015 |
| WO | WO2015006701 A2 | 1/2015 |
| WO | WO2015008013 A1 | 1/2015 |
| WO | WO2015022595 A1 | 2/2015 |
| WO | WO 2015/042343 A1 | 3/2015 |
| WO | WO2015030610 A2 | 3/2015 |
| WO | WO2015031472 A1 | 3/2015 |
| WO | WO2015036010 A3 | 3/2015 |
| WO | WO2015036723 A1 | 3/2015 |
| WO | WO2015052519 A1 | 4/2015 |
| WO | WO 2015/071404 A1 | 5/2015 |
| WO | WO2015104522 A1 | 7/2015 |
| WO | WO2015109259 A1 | 7/2015 |
| WO | WO2015114285 A1 | 8/2015 |
| WO | WO2015128173 A1 | 9/2015 |
| WO | WO2015133909 A1 | 9/2015 |
| WO | WO2015138454 A1 | 9/2015 |
| WO | WO2015144442 A1 | 10/2015 |
| WO | WO2015150029 A1 | 10/2015 |
| WO | WO2015154864 A2 | 10/2015 |
| WO | WO2015154865 A2 | 10/2015 |
| WO | WO2015174856 A1 | 11/2015 |
| WO | WO2015178907 A1 | 11/2015 |
| WO | WO2016025553 A1 | 2/2016 |
| WO | WO2016030521 A1 | 3/2016 |
| WO | WO2016033419 A1 | 3/2016 |
| WO | WO2016033421 A1 | 3/2016 |
| WO | WO2016043601 A1 | 3/2016 |
| WO | WO2016048435 A1 | 3/2016 |
| WO | WO2016049066 A1 | 3/2016 |
| WO | WO2016060863 A3 | 4/2016 |
| WO | WO 2016/079461 A1 | 5/2016 |
| WO | WO2016075525 A1 | 5/2016 |
| WO | WO2016081294 A1 | 5/2016 |
| WO | WO2016085988 A2 | 6/2016 |
| WO | WO2016090260 A1 | 6/2016 |
| WO | WO 2016/110804 A1 | 7/2016 |
| WO | WO2016111633 A1 | 7/2016 |
| WO | WO2016116591 A1 | 7/2016 |
| WO | WO2016162699 A1 | 10/2016 |
| WO | WO2016165029 A1 | 10/2016 |
| WO | WO2016181048 A1 | 11/2016 |
| WO | WO 2017/071879 A1 | 5/2017 |
| WO | WO 2017/178776 A1 | 10/2017 |
| WO | WO 2017/187116 A1 | 11/2017 |
| WO | WO 2017/194906 A1 | 11/2017 |
| WO | WO 2018/083711 A1 | 5/2018 |
| WO | WO 2018/172562 A1 | 9/2018 |
| WO | WO 2018/172563 A1 | 9/2018 |
| WO | WO 2019/007950 A1 | 1/2019 |
| WO | WO 2019/236896 A1 | 12/2019 |
| WO | WO 2019/236899 A1 | 12/2019 |

OTHER PUBLICATIONS

Product information excerpt, Boehringer Ingelheim, from web address: http://www.torpex.com/product_information/, Aug. 11, 2003 (4 pages).

Product Information, Boerhinger Ingelheim, "Introducing TORPEX™ Kaerosol albuteral sulfate): The Ultimate Tool for Equine Inhalation Treatment", from website http://www.torpex.com/product_information/, Mar. 21, 2002, pp. 1-3.

PARI LC Plus Instructions for Use (GB), PARI GmbH, dated Jul. 2001.

Photographs of nebulizer manufactured by PARI GmbH with detachable gas flow interrupter believed to have been publicly available prior to Feb. 13, 1996.

YouTube Video of "Revolizer Inhaler for Asthma Treatment", Cipla Company, dated Sep. 14, 2010: https://www.youtube.com/watch?v=2xrl4KQITw.

Japanese Office Action for Patent Application No. 2019-530773 dated Jan. 13, 2022 including translation (5 pages).

Indian Examination Report for Application No. 201917022769 dated Dec. 17, 2021 (7 pages).

* cited by examiner

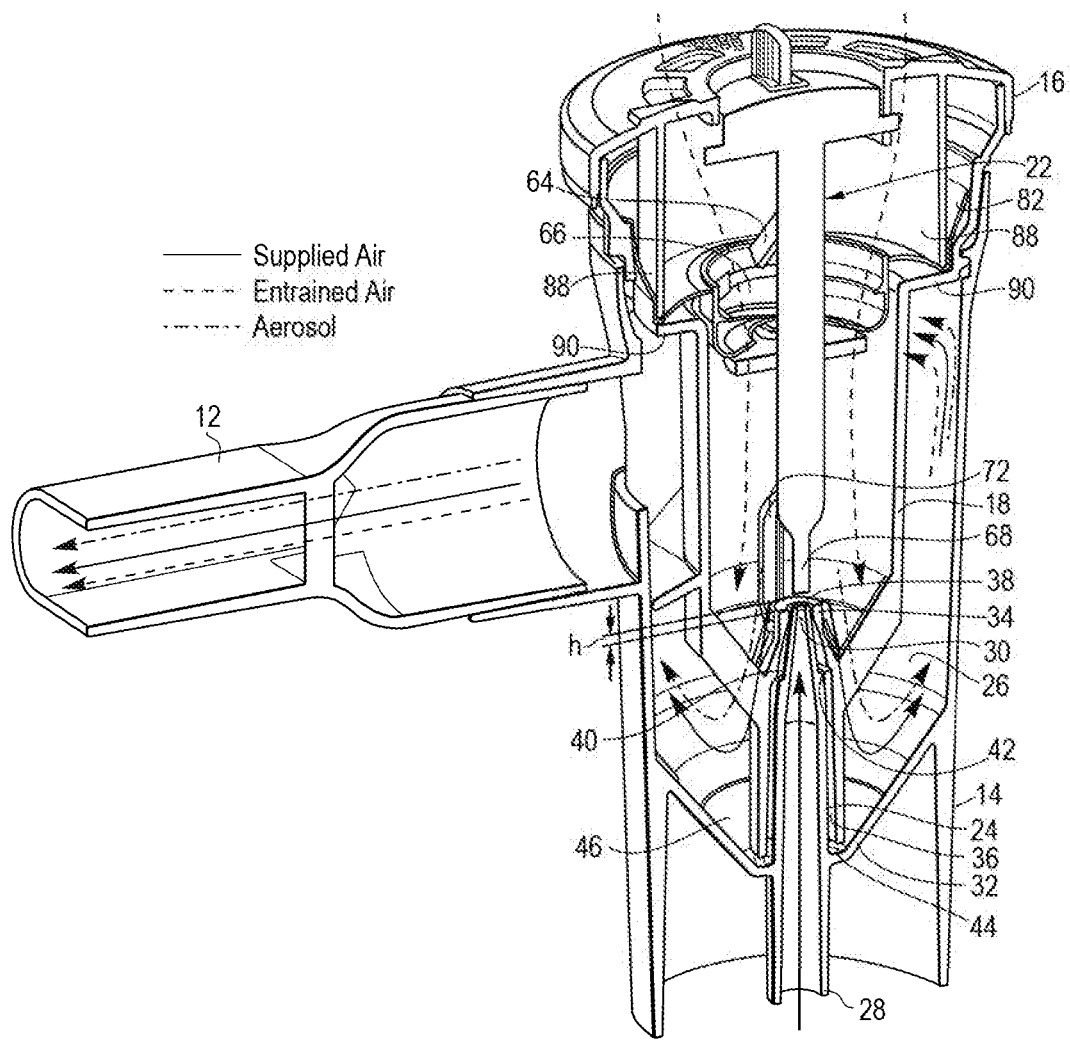

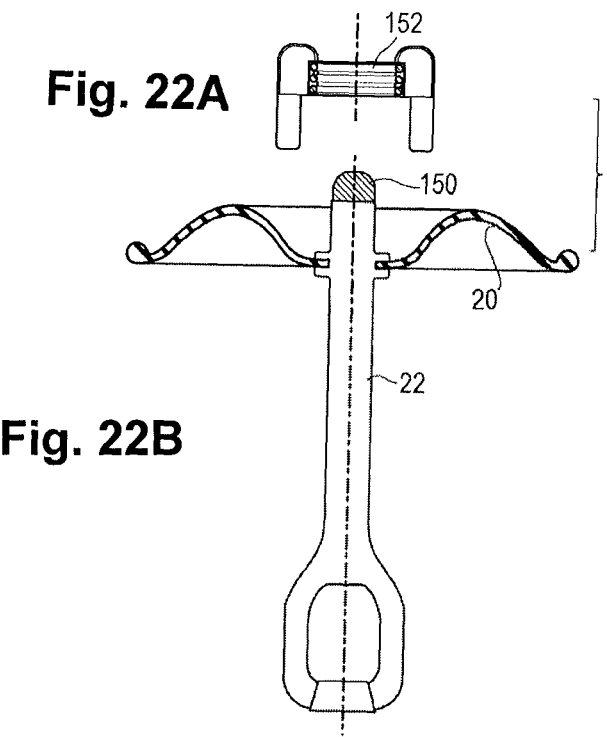
Fig. 22A
Fig. 22B
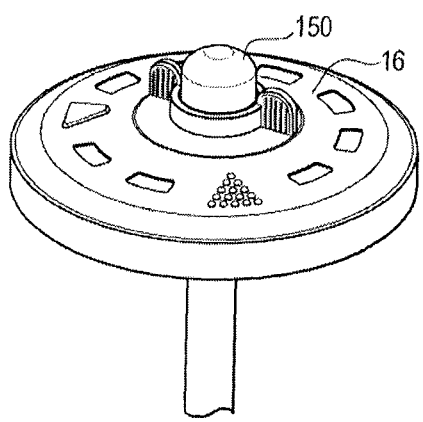
Fig. 23A
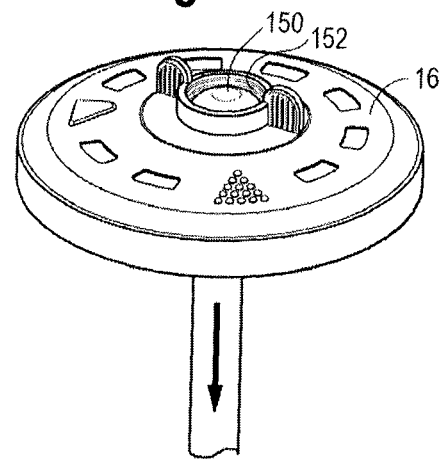
Fig. 23B

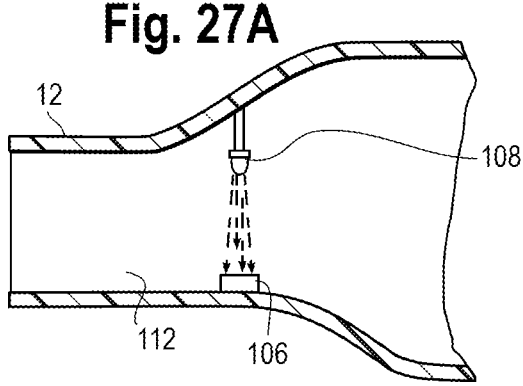
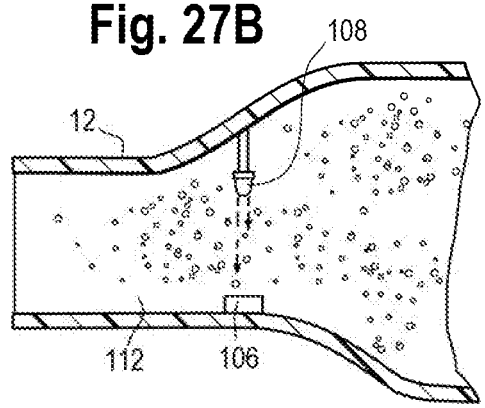
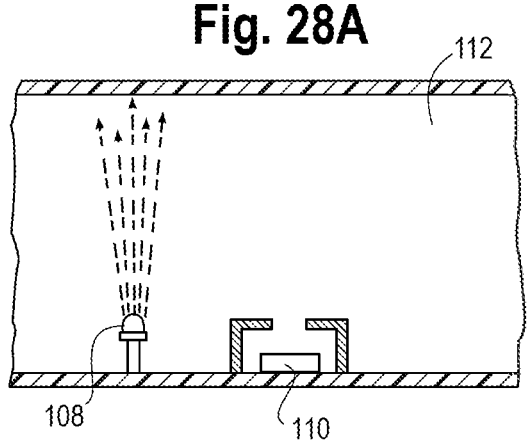
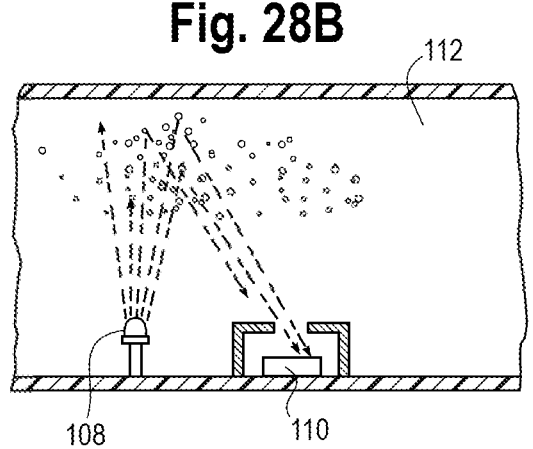

Fig. 97
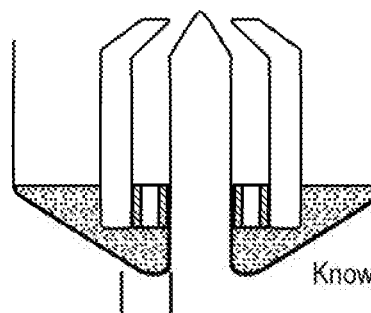
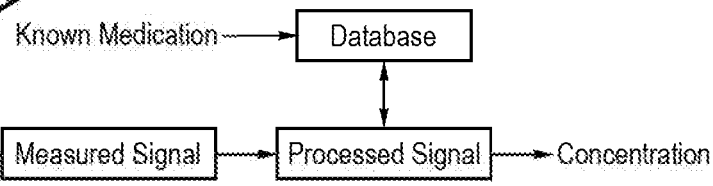
Fig. 98
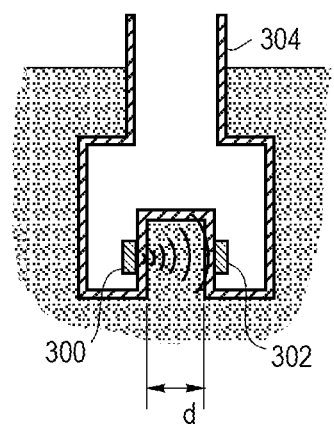
Fig. 99
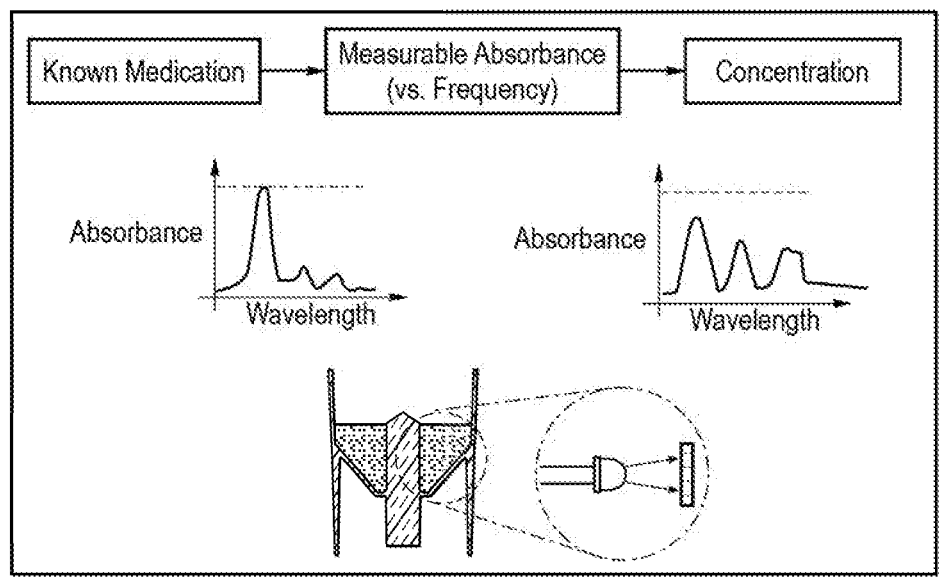

SMART NEBULIZER

This application claims the benefit of U.S. Provisional Application No. 62/432,304, filed Dec. 9, 2016, the entire disclosure of which is hereby incorporated herein by reference.

TECHNICAL FIELD

The embodiments disclosed herein relate generally to a smart nebulizer, and to methods for the use and assembly thereof.

BACKGROUND

Current nebulizers provide little or no feedback about various medication compliance aspects, including without limitation treatment adherence, drug delivery, dose assurance and proper breathing techniques. Medication compliance, while often difficult to monitor, can provide important information to the user, care providers and insurance providers.

SUMMARY

Whether in breath actuated or continuous mode, a smart nebulizer system identifies when activation has occurred and aerosol is being produced. The smart nebulizer system may provide real time feedback regarding a patient's treatment progression, the identity and amount of drug delivered, and an indication of when treatment is complete. As the patient undergoes treatment, the smart nebulizer system monitors the inhalation and exhalation flow generated by the patient and communicates proper breathing technique for optimal drug delivery. The smart nebulizer system may monitor air supply to the nebulizer to ensure it is within the working range and is producing, or is capable of producing, acceptable particle size and drug output rate.

When a patient, caregiver or other user deposits or inserts medication into the nebulizer, the smart nebulizer system is able to identify the medication and determine the appropriate delivery methods required to properly administer the medication as well as output this information into a treatment log to ensure the patient is taking the proper medications. The system is able to measure the concentration of the medication and volume of the medication placed within the medication receptacle, e.g., bowl.

In addition to analyzing when the device has activated and the flow generated by the patient, the system may also analyze the particle sizes of the aerosol and determine the respirable fraction. The device is capable of determining when end of treatment has been reached and thereafter communicating this information to the patient, or other user such as a caregiver. Upon completion of the treatment, the nebulizer system recognizes the residual volume and outputs/stores this information in a treatment log.

Using these methods, or any subset of these methods, allows the nebulizer system to determine the identity and amount of medicament delivered to patient and to provide dose assurance to the patient, healthcare provider and insurer. This information can then be stored in the nebulizer system and viewed by the appropriate parties.

The nebulizer system may also provide coaching about proper breathing techniques and posture to optimize drug delivery to the lower airways. For the health care provider, the nebulizer system can provide a treatment history record to ensure the patient is complying with the proper treatment regimen, and aid in the continued development of such a treatment regimen. This treatment log may be automated, and thereby avoid patient input and reduce the treatment burden when compared with similar logging methods, e.g., daily diaries. A treatment history record, coupled with regular check-ups helps a healthcare provider develop a proper treatment regimen, as it removes uncertainty as to whether any disease progression is due to inadequate medication or sub-optimal adherence by the patient. To provide such information, the nebulizer system is able to detect activation and deactivation, monitor the breathing pattern of the patient, measure the performance of the air supply to the nebulizer, identify the medication types and concentrations as well as the particle size the nebulizer is producing. The nebulizer system may also identify end of treatment and the residual volume of medication left in the nebulizer.

In one embodiment, the electronic portion of the smart nebulizer system is detachable from the mechanical portion, which allows for the relatively more expensive, intelligent component to be used with multiple nebulizers when such nebulizers have exceeded their useful life and/or are no longer performing optimally. The smart nebulizer system may also act as a treatment reminder for the patient to track treatment, and also prompt adherence. The detachable portion, which his portable, may be carried by the patient/user, for example by way of a clip, tether/lanyard, carrying case, wristband, etc. The portable portion may further provide a reminder about upcoming treatment requirements by way of visual, audible, tactile (e.g., vibratory) and/or haptic feedback.

The smart nebulizer system may have a user interface that can communicate information to the patient/user, including without limitation treatment progression, inhalation flow rate and breathing rate, preferably with low latency. The interface may be incorporated into the nebulizer, such as the housing, or information from the nebulizer may be communicated to a standalone device, such as a peripheral device, including for example a smartphone or tablet, for viewing. Communication of the information is not limited to visual information, such as graphics or text, but may also include audible and haptic information, communication methodologies and components.

It should be understood that the various embodiments, features and processes discussed herein are applicable to both breath actuated and continuous nebulizers.

The foregoing paragraphs have been provided by way of general introduction, and are not intended to limit the scope of the following claims. The present embodiments, together with further objects and advantages, will be best understood by reference to the following detailed description taken in conjunction with the accompanying drawings.

BRIEF DESCRIPTION OF THE DRAWINGS

The Figures show different embodiments of a medication delivery or nebulizer system, block/flow diagrams and methods for the use and assembly thereof.

FIG. 22A is a side view of an actuator and diaphragm.

FIG. 22B is a cross-sectional view of a dial.

FIGS. 23A and B are perspective view of a top of a nebulizer, showing a dome in different positions.

FIGS. 27A and B are cross-sectional views of an alternative embodiment of a flow path.

FIGS. 28A and B are cross-sectional views of one embodiment of a flow path.

FIG. 97 is a cross-sectional view of one embodiment of a reservoir and nozzle.

FIG. 98 is a cross-sectional view of one embodiment of a reservoir.

FIG. 99 is a cross-sectional view of one embodiment of a reservoir and absorbance wave lengths.

FIGS. 104A and B are cross-sectional views of an actuator and diaphragm with a contact switch.

FIG. 105 is a schematic showing a smart nebulizer system.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent, and further may be mechanical or electrical, including for example a wireless communication. The phrase "fluid communication," and variants thereof, refers to fluid being able to pass between the components, whether directly or indirectly, for example through one or more additional conduits or components. It should be understood that the use of numerical terms "first," "second," "third," etc., as used herein docs not refer to any particular sequence or order of components. It should be understood that the term "user" and "patient" as used herein refers to any user, including pediatric, adolescent or adult humans, and/or animals.

The term "smart" refers to features that follow the general format of having an input, where information is entered into the system, analysis, where the system acts on or modifies the information, and an output, wherein new information leaves the system. The phrase "performance characteristics" refers to measurements, such as frequency or amplitude, which quantify how well a device is functioning.

Figure 1:
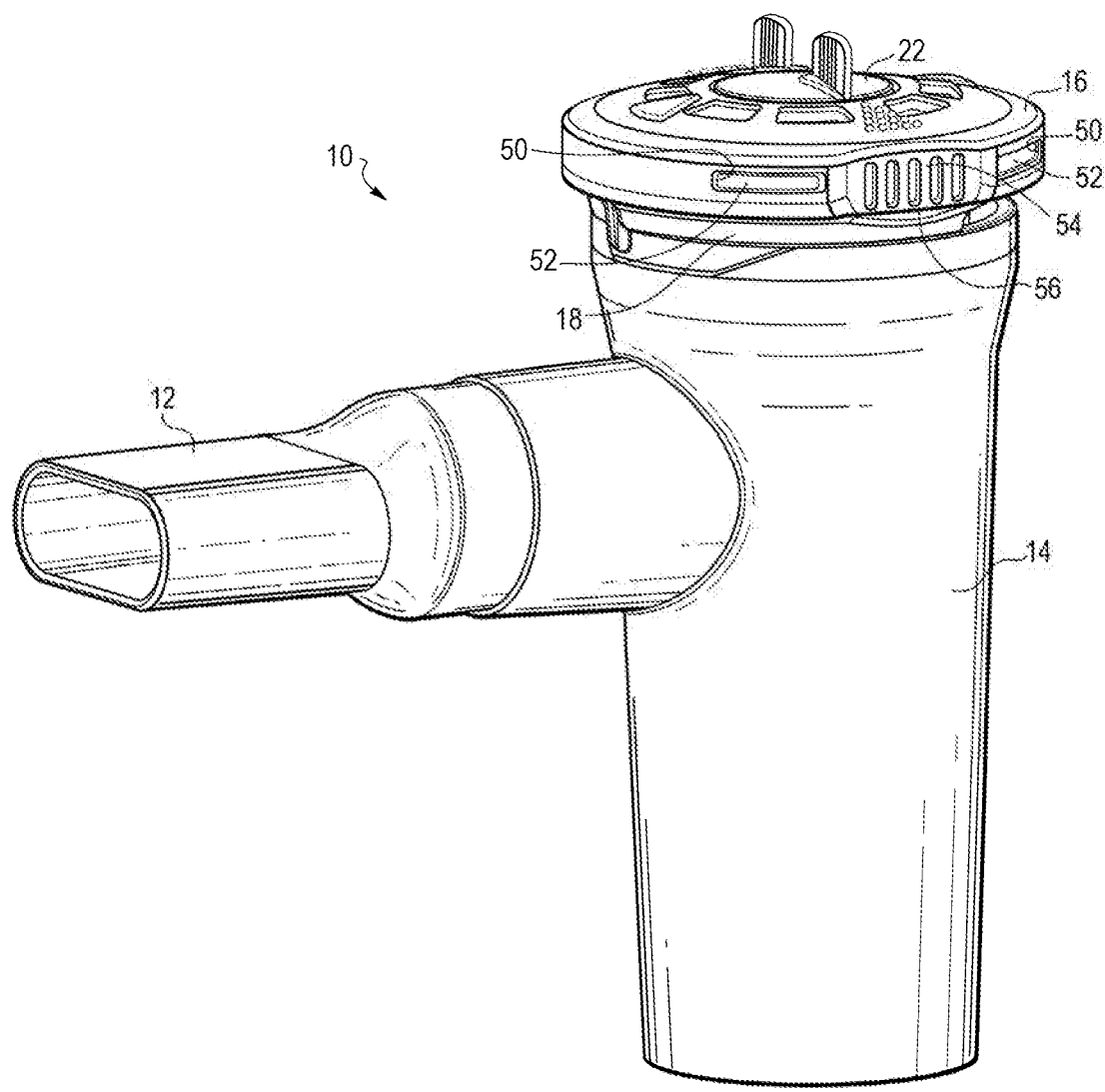
FIG. 1 is a perspective view of one embodiment of a nebulizer having a diaphragm.
Figure 2:
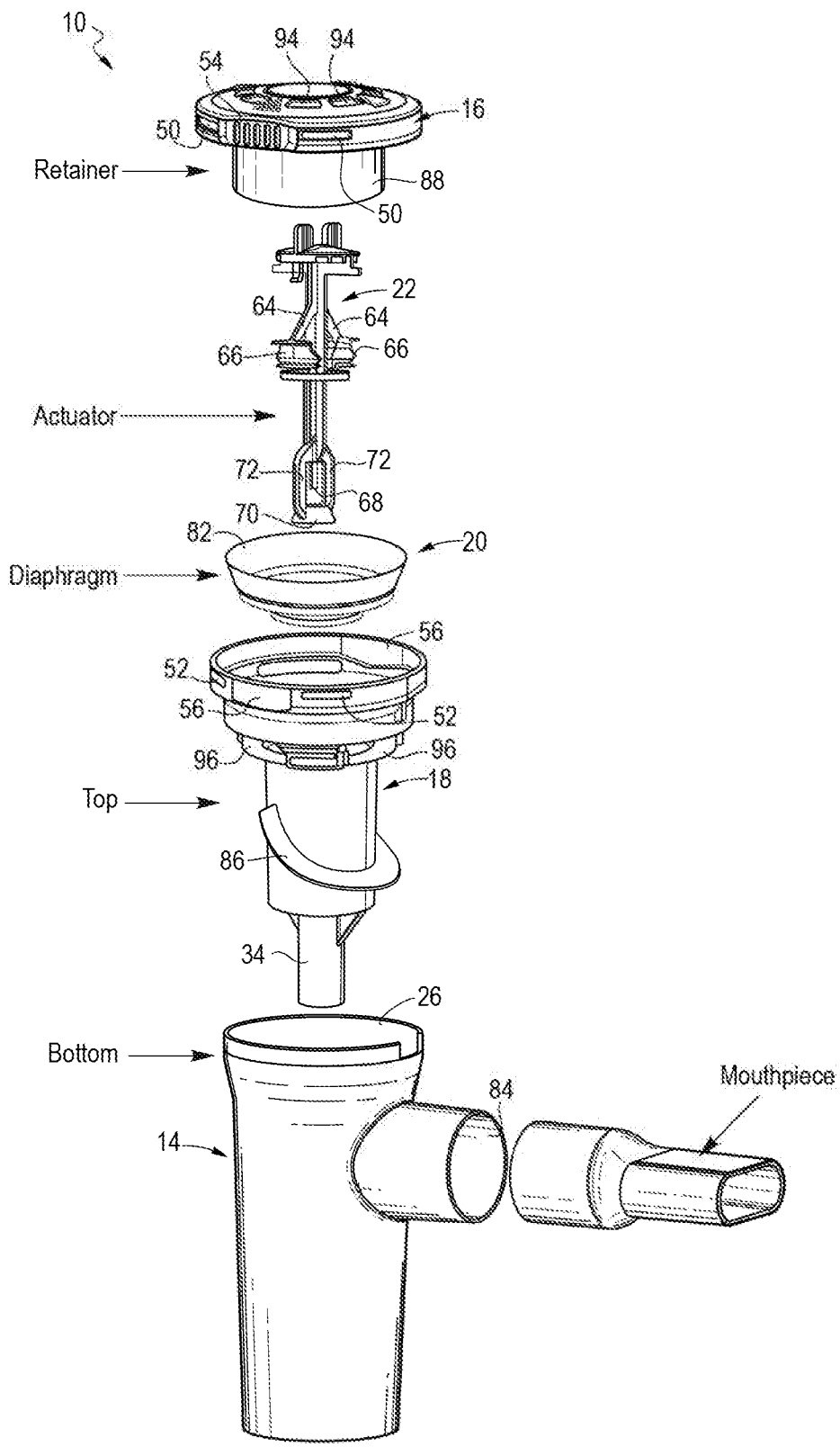
FIG. 2 is an exploded view of the nebulizer shown in FIG. 1.

Referring now to FIGS. 1-2, one implementation of a nebulizer 10 is shown. The nebulizer may include six discrete components (FIG. 2), five of which are capable of being assembled in a top-down method with each component (other than the mouthpiece 12) sharing a common central axis. This arrangement may assist with reducing complexity when implementing automated assembly. As can be seen, the components are also capable of being assembled manually and incorporate features to reduce a probability of human error in the assembly process.

The components of the nebulizer 10 include a bottom housing 14 having a cylindrical body. The nebulizer 10 also contains a top portion, referred to as the retainer 16, and an internal assembly, referred to as the inner housing 18. A flexible component is also included in the nebulizer 10, and is referred to as the diaphragm 20. A long, shaft-like component, referred to as the actuator 22, is also contained within the nebulizer 10. The final component is the tubular mouthpiece 12. The components of the nebulizer 10, other than the diaphragm 20, may be formed with a single piece of material by an injection molding process and assembled without the use of welding or adhesives and joined together using interference fits.

The retainer 16, actuator 22, inner housing 18, bottom hosing 14 and mouthpiece 12 may all be constructed from a plastic material such as, but not limited to, polypropylene. Any of a number of types of plastic may be used to construct these parts of the nebulizer 10. The diaphragm 20 may be constructed from, but not limited to, a flexible material such as silicone.

Referring to FIG. 3A, a pressurized gas inlet 24 of the bottom housing 14 extends into the chamber 26 of the bottom housing 14. The external opening 28 of the pressured gas inlet 24 is designed to press-fit with a pressured gas hose fitting (not shown). Inside the bottom housing 14, the pressurized gas inlet 24 tapers down into a nozzle with a pressurized gas orifice 30 having a predetermined diameter. Preferably the gas inlet 24 is coaxial with the cylindrical body of the bottom housing 14 and extends through the bottom wall 32 of the chamber 26. The inner housing 18 incorporates a nozzle cover 34 that slides over the pressurized gas inlet 24 on the bottom housing assembly 14.

The nozzle cover 34 is a tapered tubular member with openings at either end. When positioned over the pressurized gas inlet 24, the space between the nozzle cover 34 and the pressurized gas inlet 24 creates at least one passageway 36 between the radial opening created by the gap between the nozzle cover 34 and the bottom wall 32 of the bottom housing 14 and the annular opening 38 defined by the outer diameter of the nozzle end of the pressurized gas inlet 24 and the inner diameter of the nozzle cover 34. To maintain the proper size of the annular opening 38 and position of the nozzle cover 34 over the pressurized gas inlet 24, triangular ribs 40 may be included on the inside surface of the nozzle cover 34 and are designed to cooperate with a ledge 42 of the pressurized gas inlet 24, formed near the tip to locate the nozzle cover 34 concentrically and maintain the passageway opening 44 between the lower edge of the nozzle cover 34 and the bottom wall 32 of the bottom housing 14.

The lower chamber of the bottom housing 14 is preferably used as a reservoir 46 and holds a fluid for nebulizing, such as a solution containing medication. In one embodiment, the lower wall of the bottom housing 14 slopes down to the base of the pressurized gas nozzle so that gravity urges the fluid into the reservoir 46, towards of the opening 44 of the passageway 36. As shown in FIG. 3A, the wall of the reservoir may be set at an approximate angle of 45 degrees from the central axis of the nebulizer, although other wall angles can be used to reduce the residual volume of medication at the end of a treatment. The bottom housing 14 may be constructed from transparent plastic material to allow for the patient and medical personnel to monitor medication levels in the nebulizer 10.

Referring to FIGS. 3A and B, the passageway 36 formed between the pressurized gas inlet 24 and nozzle cover 34 guides fluid from the reservoir 46 through the opening 44 to the passageway 36 and to the annular orifice 38. In this configuration, the flow of a fluid through the passageway 36 and the flow of a pressured gas through the pressurized gas inlet 24 are roughly parallel. The initial portion of the passageway 36 through which fluid (for example a liquid) travels is an annular or cylindrical pathway that may be undivided vertically. The ribs on the nozzle cover 34 of the internal housing 18 that maintain the concentricity and height of the nozzle cover 34 with respect to the pressurized gas inlet 24 may divide the passageway 36 into three (3) separate passages near the tip of the nozzle cover 34, however the separate passages merge and become undivided past the ribs, prior to the pressurized gas orifice 30, The characteristics of the aerosol generated in the nebulizer 10, in addition to the mass output of the nebulizer, may be varied by varying the size of and number of these passages near the end of the passageway 36, as well as by extending the passages to the surface of the pressurized gas orifice 30. Other passageway dimensions and arrangements may be implemented to achieve the desired aerosol size and density during nebulization. The pressured gas orifice 30 is preferably circular in shape and concentrically aligned inside the annular orifice 38 in communication with the passageway 36.

The tip of the nozzle cover 34 and tip of the pressurized gas inlet 24 may be flat surfaces. In one implementation, the pressurized gas orifice 30 is positioned in the plane of the annular orifice 38. Alternatively, the plane of the gas orifice 30 may be parallel to, and offset from, the plane of the tip of the nozzle cover. The relative heights (offsets) of the tips of the pressurized gas inlet 24 and the nozzle cover 34 may be varied to achieve the desired nebulization characteristics.

On the opposite end of the bottom housing 14 from the pressurized gas inlet 24, the inner housing 18 is removably attached to the cylindrical wall of the bottom housing 14 through the use of three (3) equidistantly separated ledges on both the bottom housing 14 and inner housing 18 to which the inner housing 18 may be loosely rotated under for a frictional fit to the bottom housing 14. Rotational orientation of the inner housing 18 relative to the bottom housing 14 may be controlled by a tab incorporated into the inner housing 18 and a corresponding flat surface on the bottom housing 14 which arrests the rotational motion of the inner housing 18 when positioned correctly. A ramp profile in the bottom housing 14 ensures the ledges on the inner housing 18 move under the ledges on the bottom housing 14 as the tab follows the ramp profile. Though this example utilizes three (3) equidistantly spaced ledges around the outer surface of the bottom housing 14 and inner housing 18, any number of these threaded features may be used to the same effect in other implementations. When assembled, the outer surface of the inner housing 18 forms an interference fit with the inner surface of the bottom housing 14 to ensure that air and aerosol is unable to leak between the two components and into the ambient environment.

The outer flange of the retainer 16 contains four (4) cut-outs 50 which snap fit with corresponding male extrusions 52 on the outer surface of the inner housing 18 to assemble the retainer 16 to the inner housing 18. Two (2) textured flats 54 are included on the outer surface of the retainer 16 that break the circular profile of the outer flange, which aid in the assembly of the inner housing 18 to the bottom housing 14 as they mate with corresponding flats 56 on the outer surface of the inner housing 18. This aids in the implementation of automated assembly as the flats 54, 56 provide features for robotic assembly systems to grasp as well as for determining orientation with vision systems and reduce the probability of human error on assembly. The flats 54, 56 on the inner housing 18 and retainer 16 also allow the parts to be bowl fed to an automated assembly. The retainer 16 is designed such that the retainer 16 may be assembled to the inner housing 18 in either of the configurations possible that allow the flats on the inner housing 18 and bottom housing 14 to be parallel to each other on assembly as the features of the retainer 16 are symmetrical. The flats 54, 56 also help to hold the rotational orientation of the retainer 16 relative to the inner housing 18 after assembly.

Referring to FIGS. 2, 3A and B, the diaphragm 20 and retainer 16 are assembled coaxially and are mounted to each other through an interference fit between the actuator 22 latch feature of the diaphragm 20 and the receiving geometry of the actuator 22. In this configuration, the actuator 22 may be assembled with the diaphragm 20 by inserting the actuator through the inner, circular opening of the diaphragm 20 for a grommet style connection. A triangular-shaped ridge 58 around the surface of the inner opening 60 of the diaphragm 20 mates with complementary receiving triangular grooves 62 on the latching surface of the diaphragm 20. The actuator 22 incorporates two (2) curved surfaces of approximately equal diameter on the inner surface of the diaphragm 20 in this version of the latch feature.

When pushed through, the ridges slide into the receiving grooves on the actuator 22 and weakly hold the diaphragm 20 in place, relative to the actuator 22. The amount of interference between the actuator 22 and diaphragm 20 is an important element of the design as excessive force can cause deformation of the diaphragm 20, affecting the flow characteristics of the valves. No rotational orientation is required for the assembly of the diaphragm 20 and the actuator 22. There exists only a top-down orientation when assembling the diaphragm 20 to the actuator 22. Though only two (2) surfaces of contact 66 positioned at the end of support arms 64 extending from the central axis of the actuator 22, separated by 180 degrees around the common axis of the diaphragm 20 and the actuator 22, are used to stabilize the diaphragm 20, any number of such features could be used of various mating geometries though they are preferably equidistantly positioned around the actuator 22 to ensure the diaphragm 20 does not deform.

The diaphragm 20 and actuator 22 assembly is coaxially and slideably positioned within the nebulizer, inside the cavity created by the inner housing 18, with the coaxial body of the actuator 22 piston extending into the inner housing 18 along the longitudinal axis of the nebulizer as well as through a coaxial opening in the retainer 16 body. The closed, lower feature of the actuator 22 that extends into the cavity of the inner housing 18 defines a diverter 68 for diverting the flow of pressured gas emerging from the pressurized gas orifice 30. In one implementation, the diverter 68 has a flat, circular surface having a predetermined area. The surface is also preferably aligned parallel to the tip of the pressurized gas inlet 24 and perpendicular to the direction of flow of the pressurized gas through the pressurized gas orifice 30. Concentric alignment of the diverter 68 in relation to the pressurized gas orifice 30 is aided by a downward sloping flange 70 connected to the main actuator body with two arm protrusions 72. The downward sloping flange 70 acts as a guide and slides along the outer surface of the tapered end of the nozzle cover 34. The downward sloping flange 70 may be a short, tapered tubular feature with an opening at either end to allow pressured gas to travel unimpeded through its center, in addition to the tapered end of the nozzle cover 34. The flange 70 also helps to set a predetermined distance 'h' between the diverter surface and the surface of the pressurized gas orifice as the bottom of the flange 70 will contact a corresponding shoulder on the nozzle cover 34. The mouthpiece 12 is a tubular part with an ovular opening on one end for the patient to breathe through, and a cylindrical opening on the other end, that may be a 22 [mm] ISO standard fitting that is press-fit into the corresponding cylindrical tube extending from the bottom housing 14, perpendicular to the axis of assembly for all other components.

Referring to the embodiment of FIGS. 1-3B, the operation of the nebulizer will now be explained. During operation, pressured gas provided from a gas source to the pressurized gas inlet 24 is continually entering the nebulizer 10 through the pressurized gas orifice 10. There are two main positions that the actuator 22 can be in that cover the two states of the nebulizer during operation. In the first position, the diverter 68 is spaced a great enough distance away from the top of the pressurized gas orifice 30 so that nebulization is not initiated. The second position occurs during inhalation (and in a continuous nebulization mode when that mode is manually set) and is achieved when the actuator 22 moves downward in relation to the rest of the nebulizer so that the diverter 68 moves to a predetermined distance 'h' from the orifice of the nozzle appropriate for nebulization of the fluid within the reservoir 46 to occur. The pressurized gas, which may be oxygen or any other breathable gas, continually flowing from the gas orifice 30 is now deflected radially outward from the gas orifice in a 360 degree pattern by the diverter 68. The gas fans out over the annular orifice 38 at a high velocity creating a low pressure zone over the annular orifice. The low pressure zone, along with the capillary effect, draws the liquid from the reservoir 46 though the passageway 36 and into the stream of the pressurized gas. The liquid is aerosolized and drawn out of the air outlet 84 in the bottom housing 14 through the mouthpiece 12.

To improve the performance of the nebulizer 10 in eliminating non-optimally size particles, the outer surface of the inner housing 18 may include an extension 86 that extends to the inner surface of the bottom housing 14 and at least part way around the outer circumference of the inner housing. The extension 86 acts to intercept oversized particles entrained in the gas flow and condense on the lower surface of the extension 86 and fall back into the reservoir 46. This also helps to decrease the number of oversized particles being inhaled through the mouthpiece. The extension also ensures ambient air that is drawn into the nebulizer takes a more circuitous route through the aerosol before it leaves the nebulizer. This may assist to limit the particle density and reduce the chance of particle growth through accidental particle collisions. As stated above, the actuator is required to move from the UP/OFF (non-nebulizing) position and the DOWN/ON (nebulizing) position for nebulization to occur. Inhalation of ambient air into the nebulizer via the mouthpiece 12 and the exhalation of expired air through the nebulizer and out to the ambient atmosphere and the resistance to this airflow are important factors which must be controlled to minimize the work required to be done by the patient during a treatment.

The biasing element 78 integrated into the diaphragm 20 assists in the movement of the actuator 22 and is configured to ensure nebulization occurs on inhalation when in breath actuated mode yet remains off when inhalation is not occurring to reduce risk of medication released to the ambient environment. Minimizing the inhalation flow required to move the actuator 22 is desirable because lowering the flow required to actuate means that nebulization of the medication may start earlier during inhalation and stop closer to the end of exhalation, thus generating more aerosol in each breath and maximizing drug output. In the diaphragm 20 of FIGS. 1-3B, the exhalation valve 82 is incorporated into the upwards sloping, circumferential valve of the diaphragm and acts as a one-way pressure relief valve.

Inhalation airflow passes through the center-opening inhalation valve 80. In this configuration the inhalation valve 80 uses a donut valve design. As stated previously, the use of an inhalation valve 80 that seals onto the actuator 22 results in assembly that requires no rotational orientation between the actuator 22 and diaphragm 20 with only a vertical orientation needing to be considered. The diaphragm 20 is pinned in place between a ring-shaped extrusion 88 (also referred to herein as an exhalation skirt) located on the retainer 16 and a sealing surface 90 on the inner housing 18. This diaphragm retention technique helps to maintain a constant resting position for the diaphragm 20, locates the diaphragm 20 concentrically within the nebulizer 10, separates the movement of the biasing element 78 from the circumferential exhalation valve 82 and isolates the exhalation flow pathway and the inhalation flow pathway. On inhalation, the exhalation flange contacts a sealing surface incorporated into the inner housing 18 and the pathway is blocked. When sufficient negative pressure has been reached, the donut-shaped inhalation valve 80 is pulled away from the sealing surface 98 of the actuator 22 and air can flow around the sealing surface 98, through the pathway created by the donut-shaped inhalation valve 80, and into the main cavity of the nebulizer 10. Openings 94 located in the retainer 16 and openings 96 in the inner housing 18 allow air to move from the nebulizer's main chamber and into and out of the nebulizer 10.

Referring to FIGS. 3A and B inhalation and exhalation flow paths within the nebulizer 10 will now be described. Prior to inhalation by the patient, there exists an upwards force acting on the actuator 22, caused by the pressured gas entering the main chamber through the pressurized gas orifice 30 and striking the diverter 68. This upwards force raises the actuator 22 to its uppermost position, maintaining the diverter's 68 position away from the pressurized gas orifice 30, and thus in a non-nebulizing position. Maintenance of the uppermost position of the actuator is also helped by the spring characteristics of the biasing element 78 on the diaphragm 20 which biases the actuator 22 up and away from the pressured gas orifice 30. The pressured gas entering the nebulizer also creates a positive pressure within the nebulizer 10, pressing the inhalation valves against the sealing surface of the actuator.

On inhalation, the biasing element 78 of the diaphragm 20 rolls inward in response to negative pressure from within the nebulizer 10, acting on the lower surface of the diaphragm. This lowers the position of the actuator 22, bringing the diverter 68 closer to the pressured gas orifice 30 until the actuator 22 reaches the nebulizing position so that the diverter 68 it diverts the flow of the pressured gas. The negative pressure inside the nebulizer also opens the inhalation valve on the diaphragm, allowing atmospheric air to be drawn into the device to improve the delivery of fine particle mass and to maintain a low inhalation resistance to minimize the work needed to be done by the patient during inhalation. Atmospheric air is drawn into the nebulizer through openings 94 integrated into the retainer.

Figure 3B:
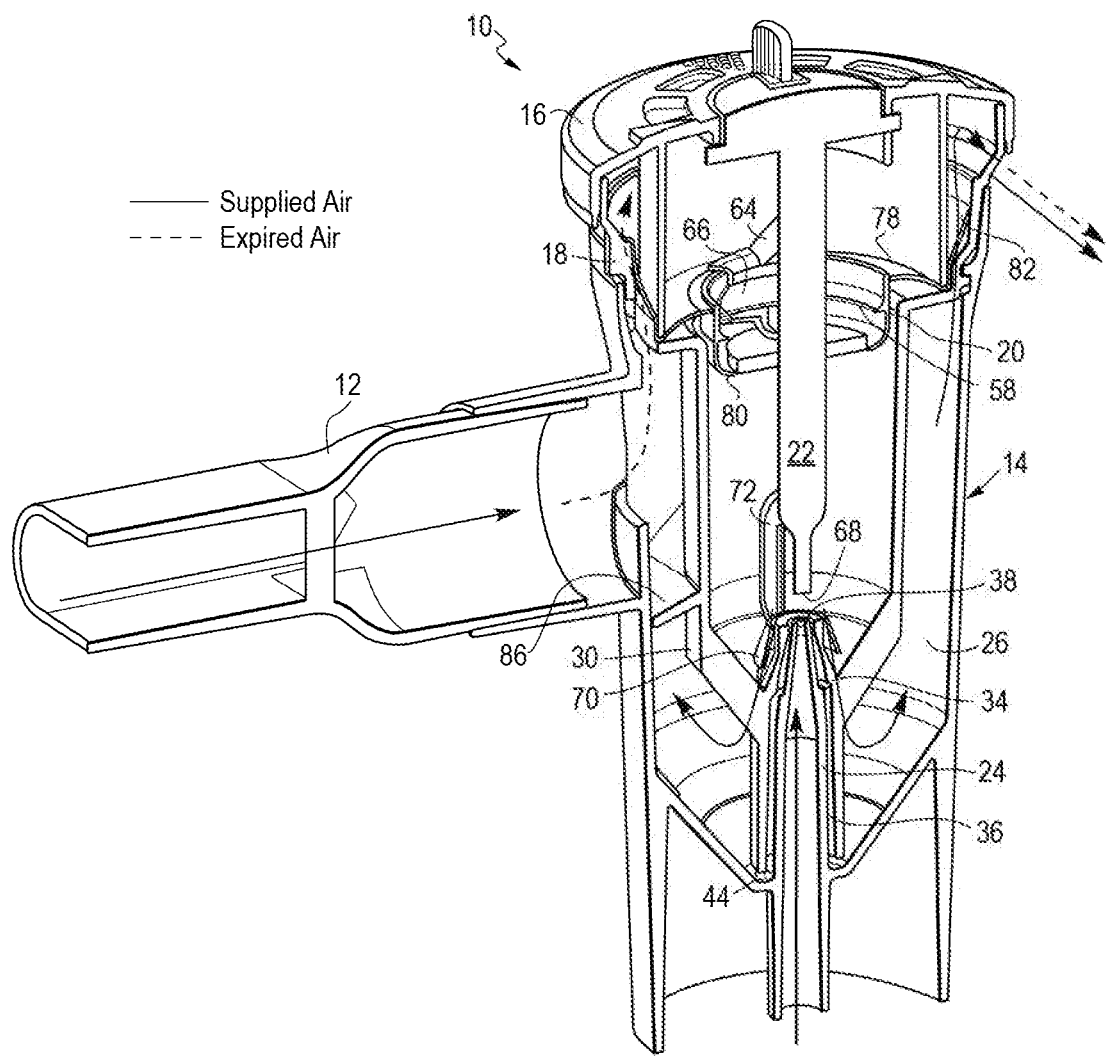
FIGS. 3A and B are cross-sectional side views of the nebulizer during inhalation and exhalation respectively.

FIG. 3A illustrates the airflow pathways of the entrained air, supplied air and aerosol on inhalation. The negative pressure generated inside the device during inhalation also ensures that the outer circumferential exhalation valve 82 on the diaphragm 20 is sealed against the inner surface of the inner housing 18, blocking the exhalation pathway from inhalation airflow. FIG. 3B illustrates the airflow pathways of the expired air and supplied air on exhalation.

On exhalation, expired air moves through the nebulizer 10 and exits through the rear of the nebulizer, away from the patient, to ensure no medication is deposited on the patient's face or eyes. In one embodiment, two (2) rectangular windows on the back and top of the inner housing 18 are used to allow the expired air to exit the nebulizer 10, however other variations in vent shape and sizing are contemplated. The vents in the inner housing 18 allow both the supplied air and expired air to exit the main chamber 26 of the nebulizer 10 and move under the circumferential exhalation valve 82. Expired air is blocked from exiting the top windows 94 of the retainer 16 due to the exhalation skirt 88 pinning the diaphragm 20 to the inner housing 18, isolating the exhalation 82 and inhalation 80 valves. Airflow is channeled around the retainer 16 between the exhalation skirt 88 and inner housing 18 and vented out of the back of the nebulizer 10 through vents 96 incorporated into the inner housing 18. The positive pressure generated within the nebulizer seals the inhalation valve 80 against the sealing surface 98 of the actuator 22 and prevents air from flowing out of the top windows 94 of the retainer 18.

Although preferably operated by breath actuation, the nebulizer 10 may also be manually actuated. The nebulizer 10 may include a manual actuating member connected with, integral to, or capable of contact with the actuator piston and extending out of the upper portion of the housing through an air inlet or other opening. The manual actuating member may be integrally formed with the actuator piston. The actuating member permits a caregiver or patient to move the actuator piston by hand, and thus move the nozzle cover, so that the nebulizer initiates nebulization. Although the manually actuable nebulizer may include a diverter that is integrally formed with the lid, any of the other diverter or nozzle configurations disclosed herein, or their equivalents, may be used.

Figure 4:
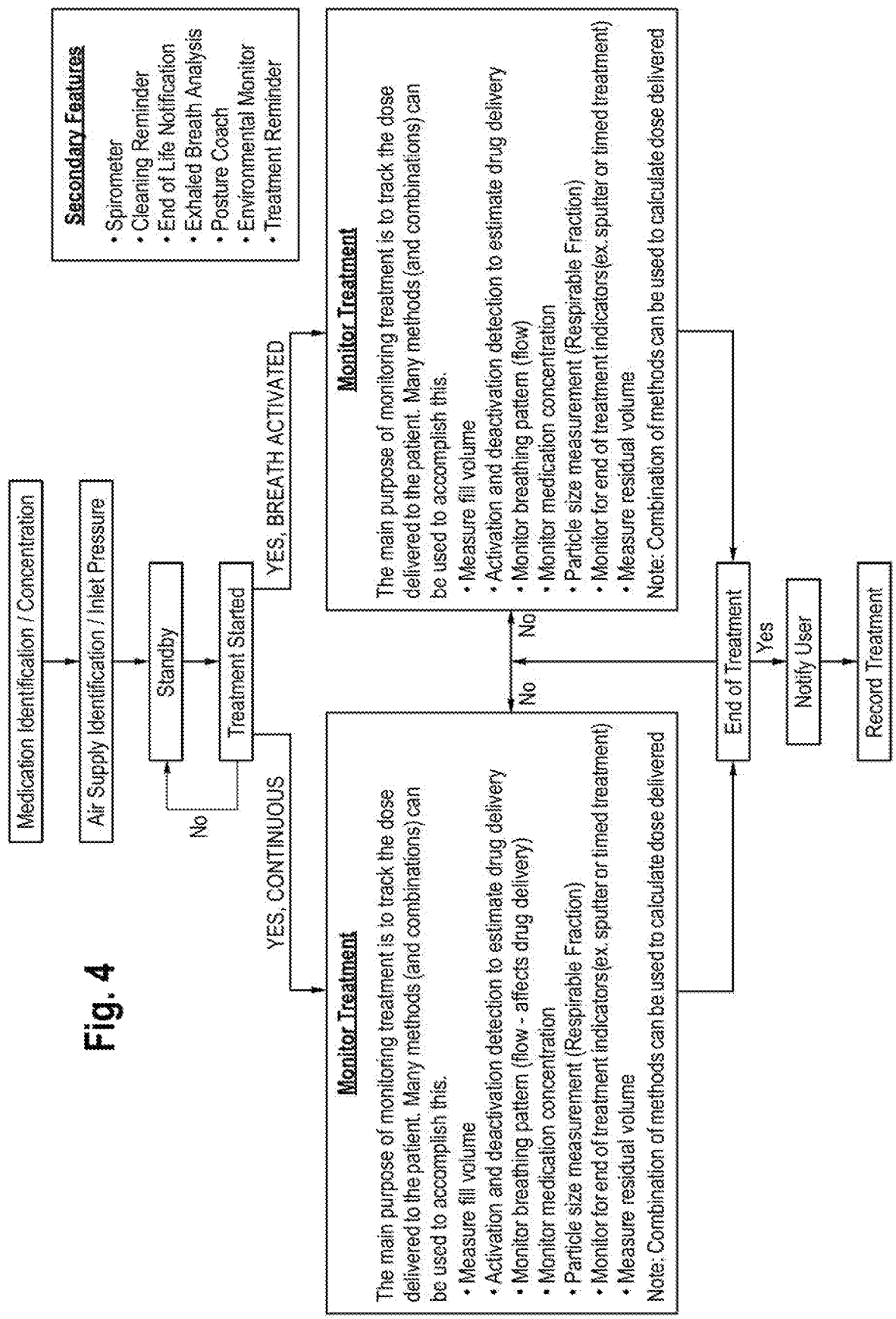
FIG. 4 is a flow chart illustrating the use and feedback loops for a smart nebulizer device.
Figure 5:
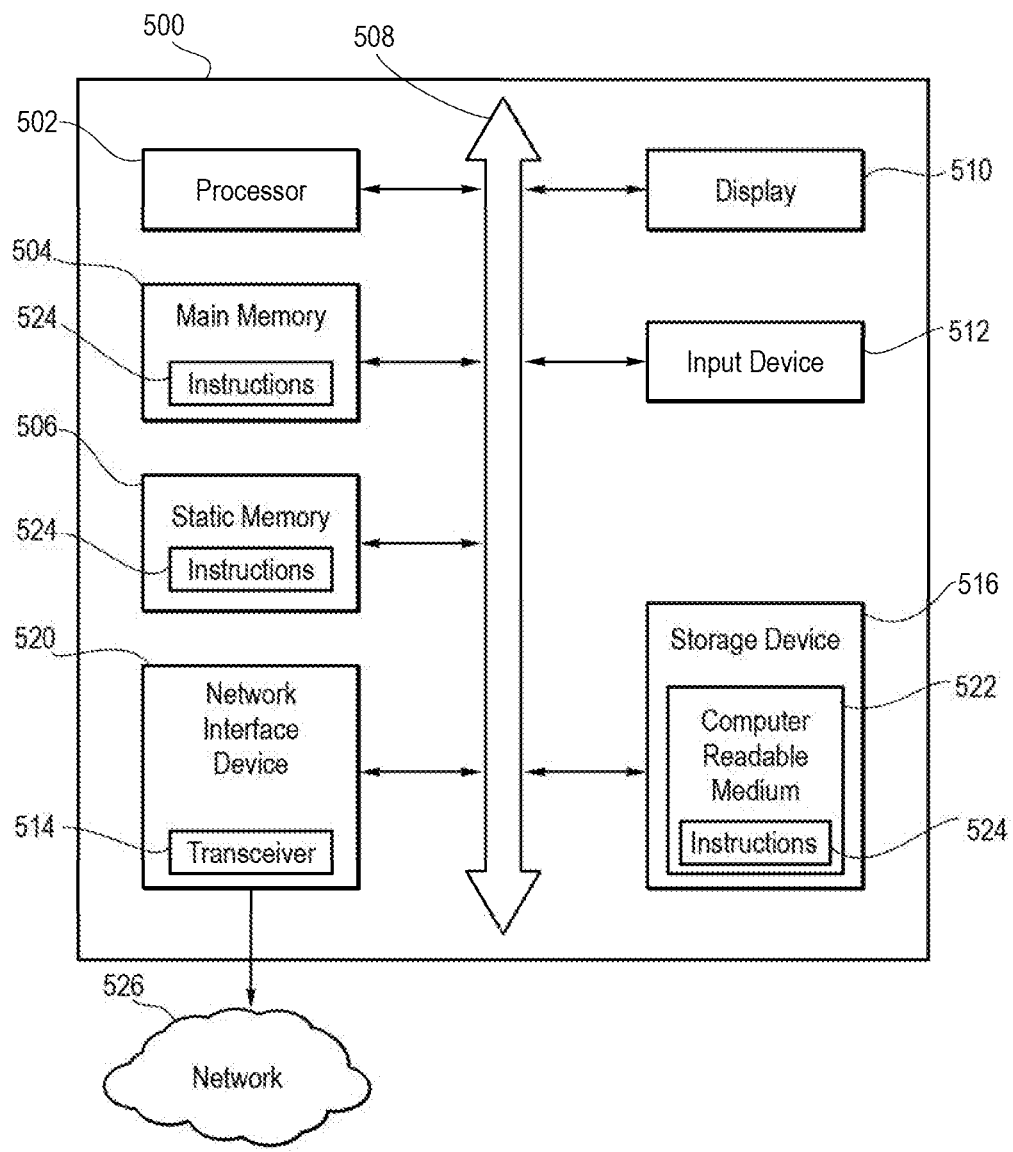
FIG. 5 is a schematic illustrating a computer structure.
Figure 6:
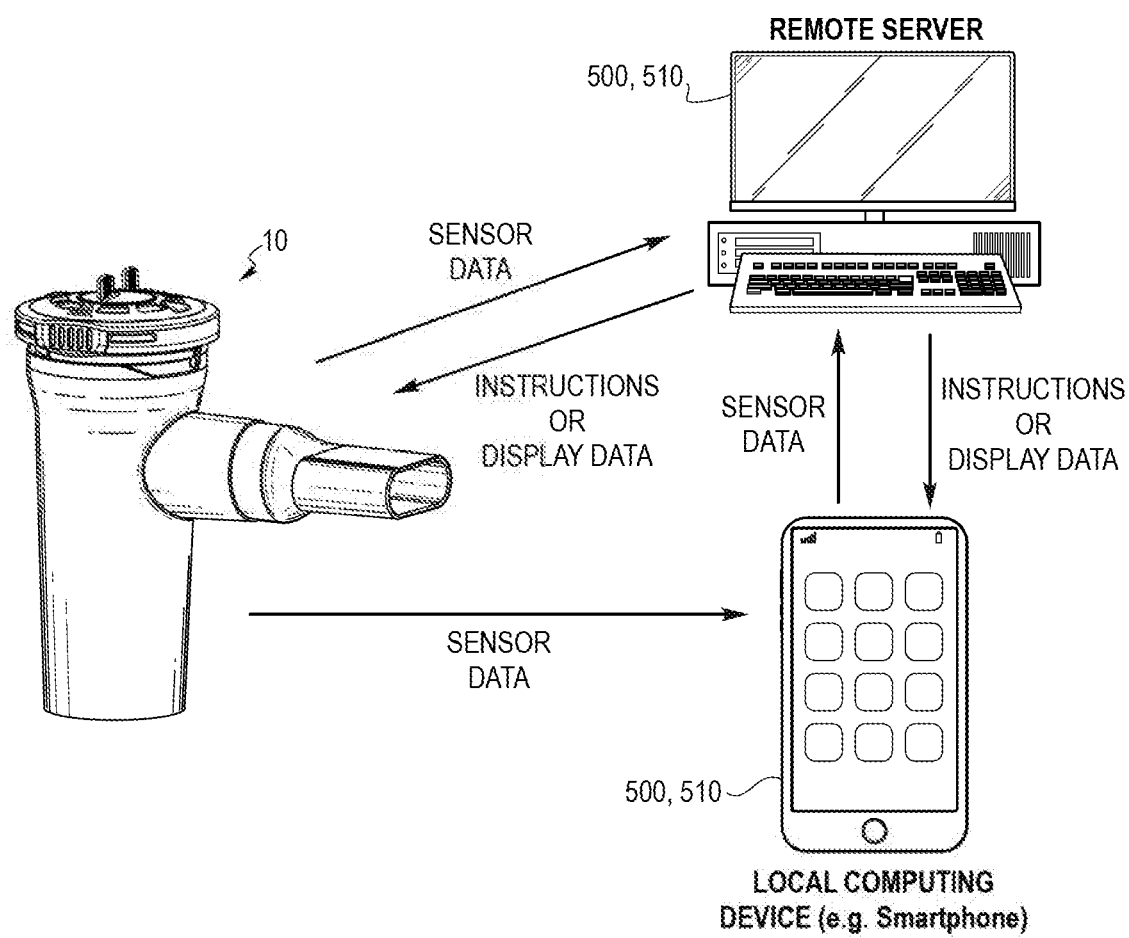
FIG. 6 is a schematic illustration of a communication system.

Referring to FIGS. 4-6, block diagrams and a schematic illustrate the operation of the device. One exemplary breath actuated nebulizer (BAN) device is the AEROECLIPSE BAN device available from Trudell Medical International, London. Various features of a BAN are disclosed in U.S. patent application Ser. No. 15/644,427, filed Jul. 7, 2017, U.S. Pat. No. 9,364,618, issued Jun. 14, 2016, and U.S. Publication No. 2013/0247903, all entitled Nebulizer Apparatus and Method and assigned to Trudell Medical International the Assignee of the present application, and the entire disclosures of which are hereby incorporated herein by reference. The various portions of the device, including the mechanical portions, may be made of a plastic material, including without limitation polypropylene. A biasing element may be made, for example and without limitation, of a flexible material, such as silicone.

The term "input" refers to any information that enters the smart nebulizer system, and may take the form of raw data from a sensor, a command to start a process or personal data entered by the user. For example, the input may be a signal from one or more sensors. For example, a pressure sensor generates an electrical signal as a function of the pressure in the system. The pressure sensor may be used to calculate any of the performance characteristics referred to above, as well as to evaluate the user's technique. A sensor assembly may include a pressure sensor placed on a printed circuit board (PCB), along with a blue tooth low energy (BTLE) module, a microprocessor, and a battery, and may communicate with a user's (patient, caregiver and/or other authorized user) computing device, such as a mobile device, including a smart phone or tablet computer, for example via bluetooth. A single pressure sensor may provide all of the measurement requirements. The pressure sensor may be a differential, absolute or gauge type of sensor. The sensor assembly may be coupled to the nebulizer device, for example with a cover disposed over the assembly.

The patient/user, care providers, physicians, insurers benefit from various features of a smart nebulizer, whether a BAN or a continuous device. For example and without limitation, the nebulizer may be linked via blue tooth to a mobile device, such as a personal digital assistant, tablet or smartphone, for example via an application. Various information that may be stored and/or communicated includes measuring flow and breathing patters, e.g., counting breaths, timing of inhalation, signal for end of treatment, recording of when (time and day) device was used, signal of correct inhalation flow, activation detection, identification of medication, concentration of medication, particle size measurement, air supply pressure, nozzle flow, and fill and residual volume determination.

In order to provide faster and more accurate processing of the sensor data generated within the smart nebulizer, data may be wirelessly communicated to a smart phone, local computing device and/or remote computing device to interpret and act on the raw sensor data. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the smart nebulizer.

In addition to simply presenting data, statistics or instructions on a display of the smart phone or other local computer in proximity of the smart nebulizer, proactive operations relating to the smart nebulizer may be actively managed and controlled. For example, if the smart phone or other local computer in proximity to the smart nebulizer determines that the sensor data indicates the end of treatment has been reached, the smart phone or other local computing device may communicate directly with a pressurized gas line relay associated with the gas supply to the smart nebulizer to shut down the supply of gas. Other variations are also contemplated, for example where a remote server in communication with the smart phone, or in direct communication with the smart nebulizer via a communication network, can make the decision to shut down the pressurized gas supply to the smart nebulizer when an end of treatment status is determined.

In yet other implementations, real-time data gathered in the smart nebulizer and relayed via to the smart phone to the remote server may trigger the remote server to track down and notify a physician or supervising caregiver regarding a problem with the particular nebulization session or a pattern that has developed over time based on past nebulization sessions for the particular user. Based on data from the one or more sensors in the smart nebulizer, the remote server may generate alerts to send via text, email or other electronic communication medium to the user's physician or other caregiver.

Figures 104A, 104B, 105:
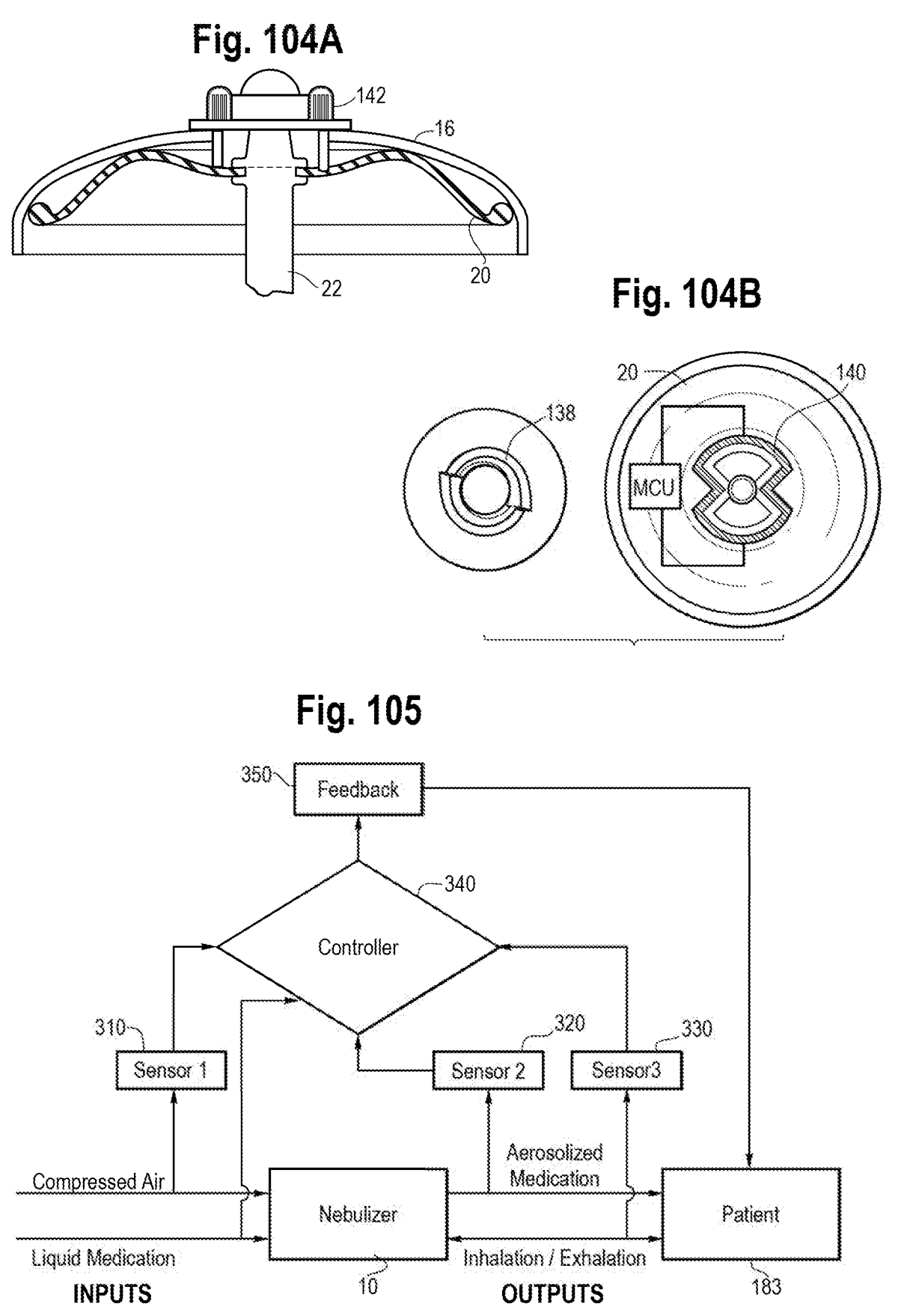

Referring to FIG. 105, one embodiment of a smart nebulizer system is shown as including a nebulizer 10 and a controller 340 with a plurality of sensors (referred to in some embodiments as detectors) (shown in one embodiment as three 310, 320, 330) providing inputs to the controller. The sensors 310, 320, 330 may be embodied, or take the form of, various sensors or detectors disclosed hereinafter. In one embodiment, the sensor 310 detects pressure and flow rates of compressed air entering the nebulizer, the sensor 320 detects aerosol generation, for example activation/actuation detection, and the sensor 330 detects inhalation and exhalation flow, breathing patterns and flow rates, with specific embodiments of each of these sensors described for example and without limitation below. Additional sensors for medicine identification, concentration identification, particle size measurement, fill/residual volume determination and end of treatment may also be incorporated into the system, as hereinafter described below. The system also includes a feedback component 350, which may include for example and without limitation, a visual, audible or haptic feedback component, or combinations thereof, including for example a display (user interface), speaker and vibratory component.

In order to calculate the respirable dose ($m_{respirable}$), the system needs input as to the total mass ($m_{total}$) delivered and the respirable fraction (RF).

$$M_{respirable}[\mu g] = m_{total}[\mu g] \times RF[\%]$$

Using a nebulizer with a consistent mass output rate [µg/min] for a given flow rate allows the system to make an assumption that the total mass output is equal to the total inspiratory time multiplied by the total mass output rate multiplied by a multiplication factor, k1, based on the average inhalation flow rate. The purpose of the multiplication factor is to account for the varying drug output and respirable fraction, based on the inhalation flow rate.

$$m_{total}[\mu g] = k1 \times m_{rate}[\mu g/min] \times t_{inspiratory}[min]$$

However, the output rate and the respirable fraction depend on the pressure and flowrate of the compressed air. Therefore, both the output rate and respirable fraction need to be expressed in terms of the input flowrate and pressure. These relationships may be empirically calculated and categorized according to nebulizer type. For example, the output rate of one nebulizer may be take the form of:

$$m_{rate} = k2 \times Q_{input} + k3 \times P_{input} + C$$

Where k2 and k3 are multiplication factors, $Q_{input}$ is the input flow, $P_{input}$ is the input pressure and C is an offset constant.

Referring to FIG. 105, sensor 310 senses the pressure and flowrate of the compressed air source and determines the output rate, which is used to calculate the total output, and the respirable fraction (RF), both of which are required to calculate the respirable dose.

Another variable required to calculate the respirable dose is the total time during which the patient/user is inhaling and the nebulizer is generating aerosol. The total time can be determined by calculating the duration of overlapping time that sensors 320 and 330 are detecting aerosol and inhalation, respectively.

Layered on top of this are the performance differences of different medications in the nebulizer system. A stored database of medications provides the necessary performance characteristics of each medication with the nebulizer. In one embodiment, the patient/user manually enters the medication information, for example by a smart device application, in wireless communication with the nebulizer system.

The smart nebulizer also provides a mechanism for improving inhalation technique through coaching and feedback. Proper breathing techniques, especially inhalation, can optimize drug delivery to the lower airways. Too forceful an inhalation can result in impaction of even respirable particles in the upper airways. Real time feedback of inhalation flow rate allows the smart nebulizer to provide a breathing coach that guides the breathing cycle of the user/patient to ensure they receive an ideal dosage of medication.

Figure 107:
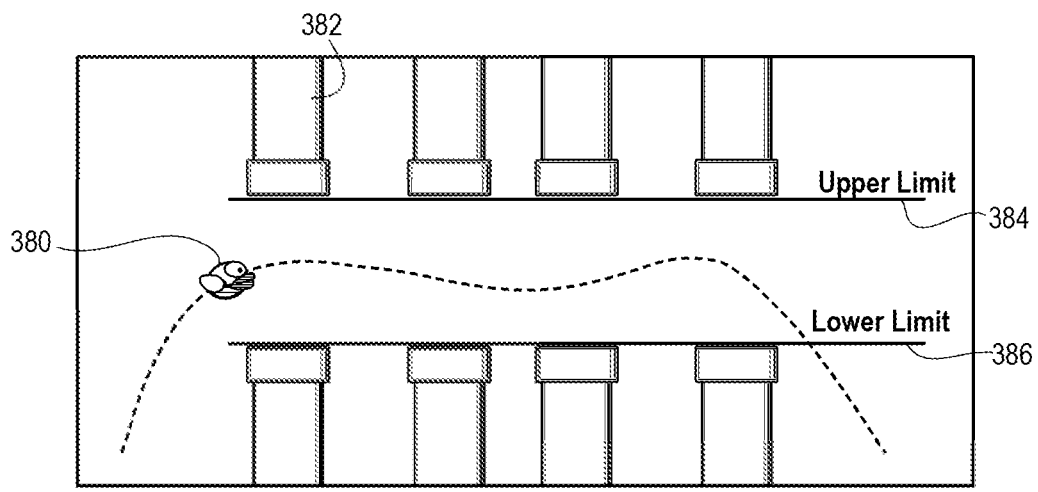
FIG. 107 is a view of a user interface with one embodiment of an output game.

For example, as shown in FIG. 107, the feedback, e.g., visual display, may be configured as a game. In one embodiment, the bird 380 represents the inhalation flow rate, which must pass through the pipes 382 without going outside the limits (upper and lower) 384, 386.

Figure 106:
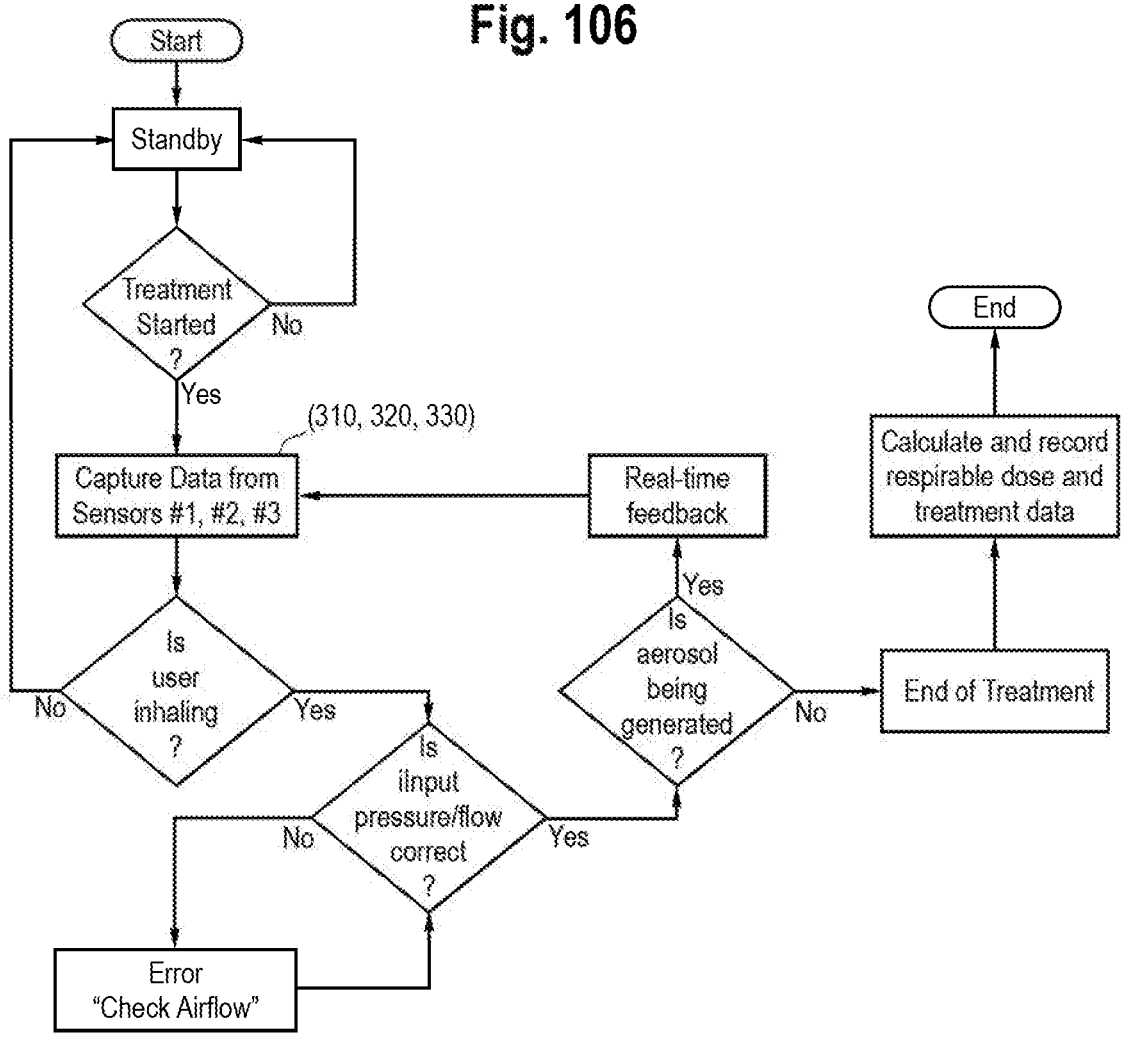
FIG. 106 is a flow chart showing a smart nebulizer treatment cycle.

Referring to FIG. 106, a smart nebulizer flow chart is shown. Once the system has detected that treatment has started, for example by sensing an activation/actuation detection, a flow from one or more sensors, or by pushing a start or on button, inputs from sensors 310, 320, 330, or other sensors disclosed hereinafter, are monitored and the data captured. If inhalation ceases for a predetermined period of time, the system will timeout and return to standby. If inhalation is detected, but the input compressed airflow is not correct, an error will be generated. If inhalation is detected and the input airflow is correct, but the nebulizer is not generating aerosol, the system will indicate the end of treatment and calculate the respirable dose and log the treatment data.

If inhalation is detected, the input airflow is correct, and aerosol is being generated, the system will provide real-time feedback via a feedback device about the user's inhalation flow rate and/or end of treatment in order to improve technique. This feedback can take several forms including visual (see e.g., FIG. 107), audible and haptic. The feedback may be provide a visual interface, an audible or vibratory warning if the inhalation flow rate is above or below a certain range. The feedback device may also provide a visual, audible or vibratory feedback indicia that the end of treatment has been reached. Acting on this feedback, the user/patient is able to control/adjust their inhalation flow rate and maintain that flow rate within an acceptable range, thereby maximizing their respirable dose.

When the nebulizer system has determined that the user has stopped using the nebulizer, the nebulizer system stores the treatment data locally, or transmits the data for storage on a separate device. The data may be viewed at a later time/date by the user or healthcare provider to track treatment adherence. Various feature, together with their respective technical requirements, are listed in Table 1, together with the value added to the nebulizer system.

TABLE 1

FEATURES, TECHNICAL REQUIREMENTS AND VALUE ADDED

| Value Added | Feature | Technical Requirements |
|---|---|---|
| Adherence/Compliance Identify when the device has been used (date/time) and for how long and/or prompt patient of treatment | Breath Counter | Identification of start and end of breathing cycle, record/track cycles |
| | Breathing Pattern Monitor | Measure and record flow measurements over the course of treatment(s) |
| | Actuation Recognition/Counter | Identify movement of actuator |
| | Treatment Log | Manual entry into app/webpage of drug type, fill volume, concentration or automatic recognition of this information. Historical display of treatment log. |
| | Treatment Time | Identification of start and end of treatment - ex. full fill volume to sputter |
| | Treatment Reminder | Software and GUI for setting reminders - displayed on device, app, SMS, email |
| Correct/Efficient Use Proper use of the device | Breathing Pattern Monitor | Measure and record flow measurements over the course of treatment(s) |
| | Treatment Time | Identification of start and end of treatment - ex. full fill volume to sputter |
| | Posture Coach | Identify patient and device orientation and provide real time feedback. App based or printed IFU. |
| | Breathing Coach | Identification of breathing pattern and real time adaptive feedback/instructions, IFU instructions. Could be made into a game |
| | Environmental Monitor | Measure the environment the device is being used/stored in (temperature, humidity, pressure) - ensure device is being used within proper operating conditions |
| Treatment Completion Awareness/Dose Assurance Identifying when treatment has been completed and notifying the patient | Breath Counter | Identification of start and end of breathing cycle, record/track cycles |
| | Breathing Pattern Monitor | Measure and record flow measurements over the course of treatment(s) |
| | Breathing Coach | Identification of breathing pattern and real time adaptive feedback/instructions, IFU instructions. Could be made into a game |
| | Dose Delivery Rate | Measure the quantity of drug passing into the user's mouth per unit of time |
| | Residual Dose | Measure the residual volume in the device after treatment |
| | Inlet Pressure | Measure and record inlet pressure, use in estimation of drug output |
| | Treatment Time | Identification of start and end of treatment - ex. full fill volume to sputter |
| Dosage Awareness/Control Provide information on how to use the device for different durations/breaths depending on drug and concentration | Breathing Coach | Identification of breathing pattern and real time adaptive feedback/instructions, IFU instructions. May include game |
| | Dose Delivery Rate | Measure the quantity of drug passing into the user's mouth per unit of time |
| | Residual Dose | Measure the residual volume in the device after treatment |
| | Treatment Time | Identification of start and end of treatment - ex. full fill volume to sputter |
| | Titration (Dose Delivered) | Calculate the mass of the drug delivered to the patient |
| Efficiency Awareness/Encouragement Positive feedback to promote faster treatments | Breathing Coach | Identification of breathing pattern and real time adaptive feedback/instructions, IFU instructions. May be incorporated into a game |
| Efficacy Awareness Real time measure of lung health or risk of exacerbation and establishment of baseline health metrics | Spirometry | Measure flow rates, time, pressure. Training required to interpret results/complicated algorithm |
| | Analysis of Exhaled Breath Condensate | Collection of exhaled air (cooling required) |

TABLE 1-continued

FEATURES, TECHNICAL REQUIREMENTS AND VALUE ADDED

| Value Added | Feature | Technical Requirements |
|---|---|---|
| Device Status Awareness Identify when device has exceeded usable life and/or should be replaced | Dose Delivery Rate | Measure the quantity of drug passing into the user's mouth per unit of time - deterioration over time |
| | Internal Nebulizer Pressure | Measure pressure inside device to provide information on leakages and compressor status |
| | Expiry Date Reminder | Identification of first use and number of treatments completed/time elapsed since first use |
| | Environmental Monitor | Measure the environment the device is being used/stored in (temperature, humidity, pressure) - recognize if storage conditions are exceeded |
| Hygiene/Safety Awareness Reality or perception of improved hygiene | Environmental Monitor | Measure the environment the device is being used/stored in (temperature, humidity, pressure) - determine if proper cleaning has been achieved |
| | Cleaning Reminder | Recognition of the number of treatments completed and prompt user that cleaning is required and cleaning method recommended |
| Sustainability/ Responsibility Awareness Provide information on proper disposal | Disposal Prompt/Instructions for Disposal (after expiry date is reached - app based) | Recognize end-of-life and prompt user to dispose of product and provide proper instructions for disposal. |

Activation Detection

In order for the system to be able to track dosage delivered to the patient and determine when the end of treatment has been reached, the nebulizer system identifies when the device has activated and aerosol is being produced. Knowing the duration of activation, in conjunction with known performance characteristics of the nebulizer, the delivered dosage may be tracked over time and end of treatment calculated. In a BAN device, aerosol is generated when the actuator moves from the OFF position to the ON position and aerosol is drawn up the liquid channels and impacts on the primary baffle to generate aerosol. In some BAN devices, e.g., the AEROECLIPSE nebulizer, a manual override button may be manually depressed to produce aerosol, or a mode selector dial may be actuated to position or configure the nebulizer in a continuous mode, where aerosol is produced continuously. It would be advantageous, but not necessary, if a smart nebulizer system can differentiate between a BAN device or mode and a continuous delivery device or mode, as each of these scenarios can affect the dosage that is delivered to the patient. The movement of the actuator, audible cues, pressure characteristics, transmissibility through aerosol flow, temperature and humidity variations in the presence of aerosol, capacitance and inductance can all be used, but are not limited, to determining when the nebulizer has been activated and deactivated.

Sound-Based Approach Sensor in Device

Figure 14:
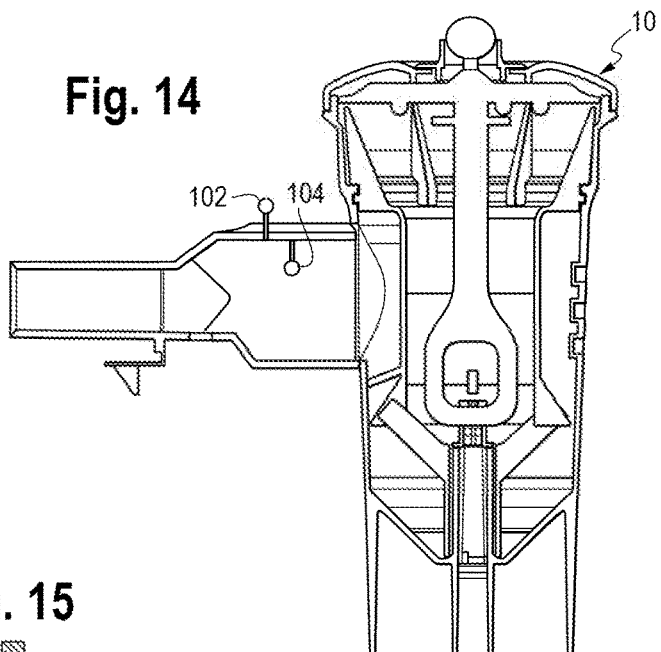
FIG. 14 is a cross-sectional view of one embodiment of a nebulizer.
Figure 15:
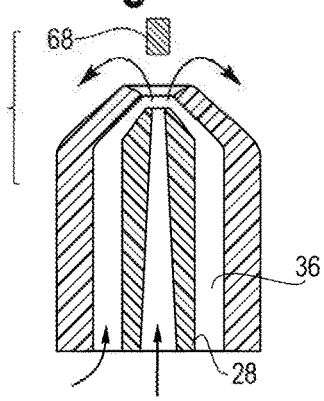
FIG. 15 is a cross-sectional view of a nozzle and cover.
Figure 16:
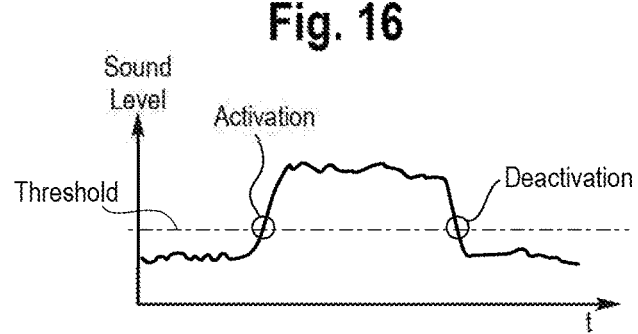
FIG. 16 is a graph showing sound level v. time during a breathing cycle.

Referring to FIGS. 14-16, in a sound based approach, microphone(s) 102, 104 are used to "listen" for audible cues that indicate activation has occurred and aerosol is being generated. Many time and frequency domain methods are available that may be used to analyze the signal provided by the microphone. A sound-based approach has the added benefit of being able to differentiate when the nebulizer is being run dry (e.g., when patient practices breathing technique prior to filling the medication bowl).

There is an audible difference in a device that is being run dry and one that is aerosolizing fluid. In addition, a microphone can be used to listen for sputter, an indication that treatment has been completed. Prior to actuation, comipressed air is flowing through the device. On actuation, liquid is drawn up the liquid channel and strikes the baffle/diverter, creating an audible cue that actuation has occurred. A second microphone may be used to measure background signal and noise level. The noise or sound level(s) may be recorded over time. The microphone may also record deactivation.

In all sound-based approaches, it should be understood that the role of the microphone 102, 104 may not be limited to listening for activation and deactivation but may also be used to record background noise and to cancel out this noise from inside the system so as to help determine which signals indicate activation has occurred. An example of this would be an algorithm used in many noise cancelling headphones where an external microphone provides a reference noise signal and the systems will add the signal of the same amplitude but inverted phase to the signal originating from inside the system as destructive interference.

External Microphone

In one embodiment of a smart nebulizer system, an external microphone 102 is used to "listen" to the nebulizer. In this application the microphone can be a standalone part that is separate from the nebulizer itself or it can be the microphone from a phone that is placed near the patient to record sounds that occur during the treatment and display information to the patient using an app based interface.

Light-Based Methods

Light Transmission—Actuator

Referring to FIG. 26, in a light transmission activation detection set-up, a light detector 106 is positioned opposite a light source 108 with an air gap separating them. In one embodiment, the gap between the light source and the detector is unobstructed when an opaque actuator 22 is in the OFF position. Movement of the actuator 22 breaks the air gap between the light source and sensor and changes the output from the light detector, indicating the actuator has travelled sufficiently to generate aerosol. In another embodiment, the air gap between the light source and light detector is obstructed by the actuator in the OFF position. When the actuator moves into the ON position, the gap is no longer impeded and the signal from the sensor changes. This is not limited to the visual spectrum of light. In one embodiment, infrared is used so that it is not visible by the patient.

Light Transmission—Aerosol

Referring to FIGS. 27A and B, as stated previously, in a light transmission method there is an air gap between the light source 108 and detector 106 and changes in the signal from the light sensor indicate that activation has occurred. In an aerosol based trigger, the light source and sensor are positioned such that the air gap between them is in an aerosol or flow pathway 112, for example in the mouthpiece 12 or chamber 14, and production of aerosol will disrupt the light due to scattering by the aerosol particles. This will reduce the light detected by the sensor, indicating that activation has occurred. This is not limited to the visual spectrum of light and may use multiple wavelengths. In one embodiment, infrared is used so that it is not visible by the patient.

Light Reflectance

Referring to FIGS. 28A and B, in a light reflectance embodiment, a light sensor 110 and light source 108 are located along the aerosol pathway 112. The components are isolated from each other and placed adjacent to each other such that, when the nebulizer is not activated and no aerosol is being produced, limited light is detected by the sensor due to limited reflectance by the opposite face of the device. In the presence of aerosol, there is increased reflection due to the close proximity to the adjacent light source and sensor which produces a measurable difference in the intensity of the light detected by the sensor. This is not limited to the visual spectrum of light and may use multiple wavelengths. In one embodiment, infrared is used so that it is not visible by the patient.

Colour Reflection

Also referring to FIGS. 28A and B, a white light source 108 is positioned adjacent to a detector 110 capable of identifying the colour spectrum of the detected light. The components are placed in the aerosol pathway such that on activation, aerosol is drawn in front of the components, such that the presence of the aerosol particles causes light to be reflected back at the sensor. In the presence of aerosol, the aerosol will absorb certain wavelengths of light thus changing the wavelengths that are free to pass back to the sensor. A change in the wavelengths detected by the sensor indicates that aerosol is present, and may identify the medication that is being aerosolized and the concentration thereof.

Acceleration

Figure 18:
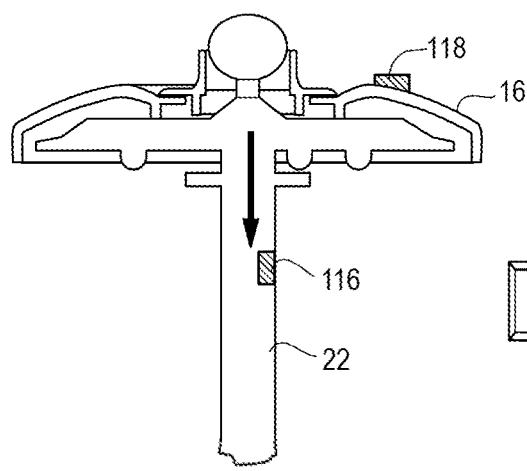
FIG. 18 is a schematic representation of an actuator.
Figure 17:
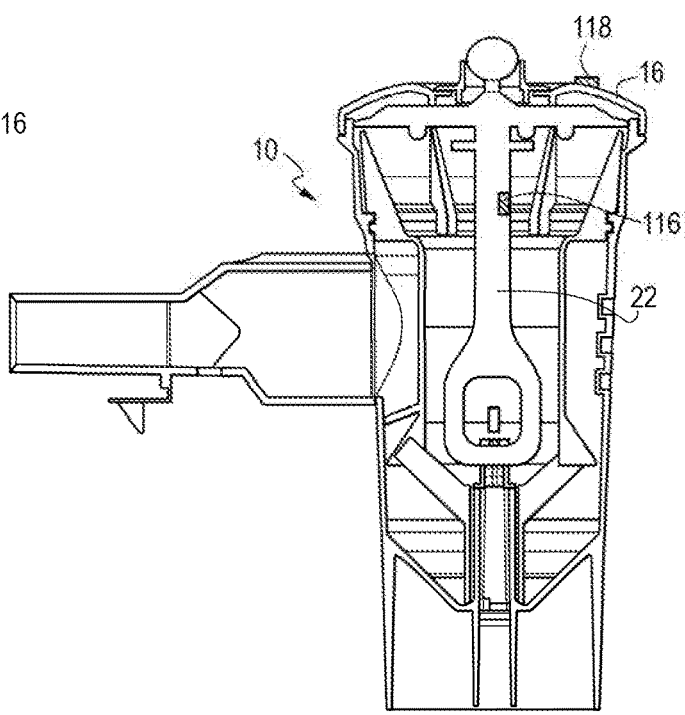
FIG. 17 is a cross-sectional view of one embodiment of a nebulizer.

Referring to FIGS. 17 and 18, in one embodiment of the breath actuated nebulizer, the actuator 22 moves between OFF and ON positions in response to inhalation sufficient to overcome the positive pressure within the device. An accelerometer 116 placed within or on the actuator 22 could be used to measure the movement of the actuator and duration at which it accelerates. The area under the generated acceleration versus time curve may then be used to determine the change in velocity and total displacement of the actuator. Determination of activation is not limited to calculating displacement of the actuator and other algorithms may be used to accomplish the same task, such as the acceleration on inhalation and sudden deceleration when the actuator bottoms out on the nozzle cover. To improve the accuracy of an accelerometer based activation detection method, a second accelerometer may 118 be used to serve as a baseline or frame of reference for the actuator movement. The second accelerometer would be placed in a portion of the nebulizer that is stationary in relation to the rest of the device and does not move in response to inhalation and exhalation flows (ex. placed within the mouthpiece 12, on retainer 16, top, bottom, etc.). By doing so, motion artifacts caused by the movement of the patient holding the device will not trigger a "false positive" activation detection as both accelerometers should register similar accelerations and the difference between them will be approximately zero. As the accelerometers 116, 118 are placed in separate components with the processing unit ideally located with the stationary accelerometer, a wired or wireless communication system may interface between the devices. In a wired connection embodiment, a single power supply may be used, while a wireless system embodiment may require multiple power supplies for the sensors.

Pressure

Absolute Pressure

Figure 10:
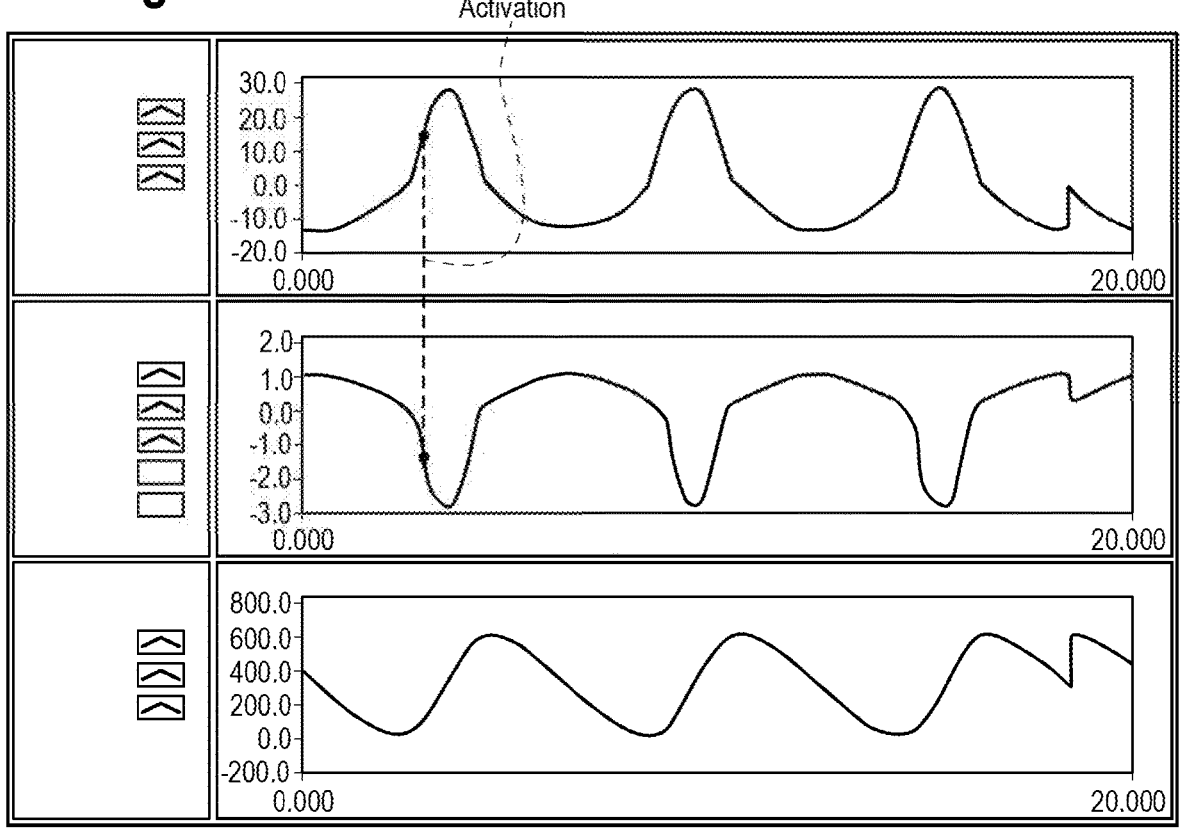
FIG. 10 shows one pressure and flow profile of one embodiment of a nebulizer.
Figure 11:
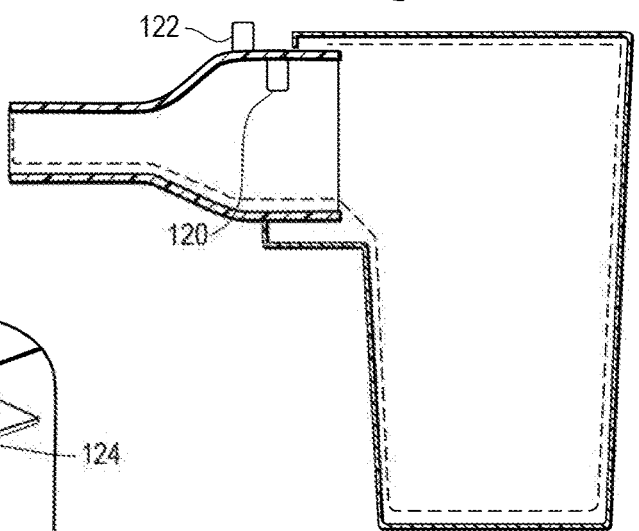
FIG. 11 is a side view of another embodiment of a nebulizer.
Figure 12:
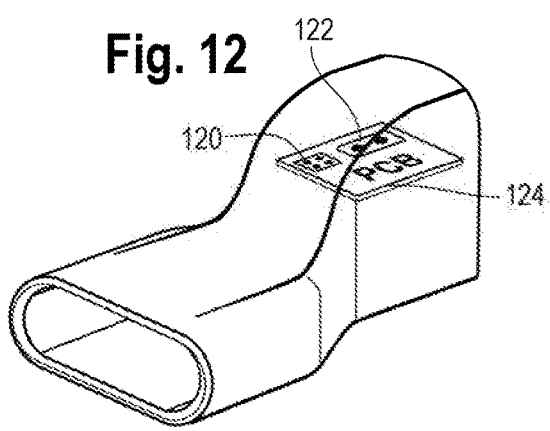
FIG. 12 is a perspective view of a mouthpiece for a nebulizer.

Referring to FIGS. 10-12, breath actuated nebulizers 10 are configured with a component 120 that responds to changing pressure within the device caused by inhalation and exhalation by the patient. When connected to a compressor, or positive pressure air supply, a positive pressure within the device pushes up on a biasing element/diaphragm 20 and maintains the actuator into the OFF position. When the patient inhales through the device, thereby causing the pressure within the device to become sufficiently negative to pull the actuator into the ON position, aerosol is generated. A pressure sensor 120 placed within the device, for example within the flow path 112 of the mouthpiece 12 can measure the pressure relative to atmospheric conditions (using a sensor 122) and identify when activation has occurred, based upon known pressure characteristics of the nebulizer on inhalation. As shown in FIG. 10, graphs of pressure and flow profiles are illustrated, with the actuation determined based on the measured pressures. A second pressure sensor 122 may be mounted exteriorly of the device, for example on the retainer or mouthpiece, to provide a reference data point for atmospheric pressure. A simple threshold analysis can be used to compare the current pressure reading with a minimum pressure required to activate the device.

The pressure sensors may provide information for determining breathing patterns, and the monitoring thereof. When connected to the mouthpiece, the sensor(s) 120, 122 may be removed with the mouthpiece so that the reset of the device may be cleaned. For example, as shown in FIG. 12, the sensor 120, 122 may be mounted with a printed circuit board 124 on the top or bottom of the mouthpiece in a location that is not disruptive of the oral interface with the user.

Another approach is to analyze the pressure profile within the nebulizer. The pressure curve of the system over the course of a breathing cycle is characteristic of the nebulizer device and responds to the movement of the inhalation and exhalation valves. Using this known characteristic profile and targeting the region that signals that activation has occurred, a signal originating from a pressure sensor 120 within the nebulizer system can be compared to a target signal, in both the time and frequency domain. This includes, but is not limited to, thresholds, autocorrelation, minimization of root-mean squares and spectral coherence. Multiple analysis techniques can be used together to improve the accuracy of the algorithm.

Strain Gauge

Figure 7:
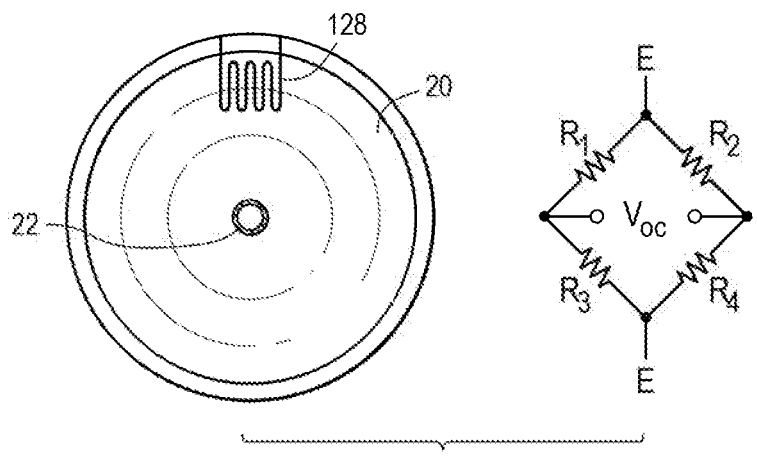
FIG. 7 is a top or bottom view of a diaphragm.
Figure 8:
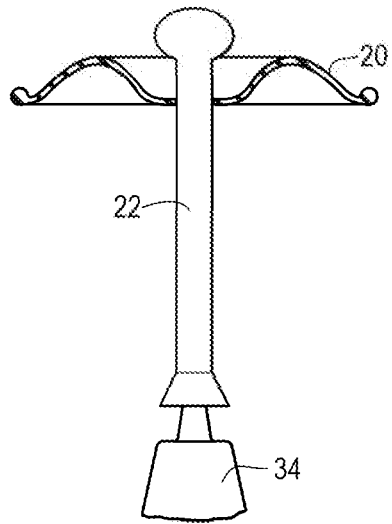
FIG. 8 is a side view of one embodiment of an actuator, diaphragm and nozzle cover.
Figure 9:
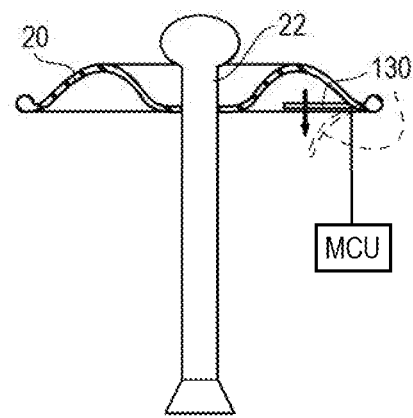
FIG. 9 is a side view of another embodiment of an actuator and diaphragm.

Referring to FIGS. 7-9, in one embodiment of a breath actuated nebulizer, the diaphragm 20 reacts to changing pressures within the device to move the actuator from an OFF to an ON position. As such, there is a minimum strain experienced by the diaphragm 20 as the actuator 22 is moved and bottomed out on the nozzle cover 34. A strain gauge 128 may be applied to the flexible biasing element of the nebulizer, with the impedance of the gauge changing in response to changing pressures within the nebulizer. One embodiment of such a device would involve the printing of a circuit on the surface of the diaphragm 20. When strained, the circuit pathways becomes stretched and narrower, resulting in a higher resistance. Conversely, when compressed the circuit becomes shorter and wider, lowering the resistance. Another embodiment of this system may have a separate flex sensor/strain gauge 130 whose movement is driven by the movement of the diaphragm 20 or actuator 22, accomplishing the same function as a strain gauge printed on the surface of the diaphragm. A simple threshold algorithm would be required to determine when sufficient strain on the diaphragm has occurred to move the actuator to the ON position. The amount of strain experienced by the gauge is related to the pressure experienced within the device and the flow rates generated by the user. In addition, the initial strain experienced by the diaphragm is indicative of the air supply pressure (compressor versus central wall air) and may be used in calculating the dose delivered.

Physical Switch

Single Pole, Single Throw (SPST) Switch

Referring to FIGS. 103A-104B, in a SPST switch embodiment, a moving element in the nebulizer, such as the actuator 22 or diaphragm 20, is used to close or open a switch. In a normally "off" switch embodiment, the actuator 22 and the hood seat of the nozzle cover 34 form a single pole, single throw switch 132. An electrical power supply is connected to a conductive path that is discontinuous in the area of the hood seat on the nozzle cover. The bottom surface 134 of the hood of the actuator contains a conductive path that bridges the discontinuous section 136 on the nozzle cover, completing the circuit and signaling that activation has occurred. When the nebulizer deactivates the circuit becomes discontinuous. A microcontroller is used to monitor the state of the switch.

As shown in FIGS. 104A and B, in a normally "on" switch embodiment, the inner surface 138 of the dial contains a conductive path that extends down the legs of the dial to where they meet the diaphragm. A conductive path 140 is printed onto the surface of the diaphragm 20 that connects the contact points of the dial legs. The path does not continue up the ramps that the legs move over when switched to continuous mode. When the nebulizer is off, the circuit is continuous. On inhalation the diaphragm 20 moves in response to the negative pressure inside the nebulizer and breaks the circuit. Conversely, when the dial 142 is rotated to continuous mode, the legs move over the ramps of the diaphragm which do not contain a conductive path. A microcontroller monitors the state of the switch to determine when activation or deactivation occurs.

It is important to note that while the two embodiments described in this section use existing components of the nebulizer to create a switch, an additional component may be added to the nebulizer that responds to inhalation and exhalation flows to indicate when activation and deactivation occurs. In addition, the method may be extended further than the two embodiments listed and may be expanded to include any normally on or normally off switch that changes state in response to activation or deactivation of the nebulizer. The embodiments used in this section were included for illustration purposes and show how such a method may be implemented.

Reed Switch

Figure 101A:
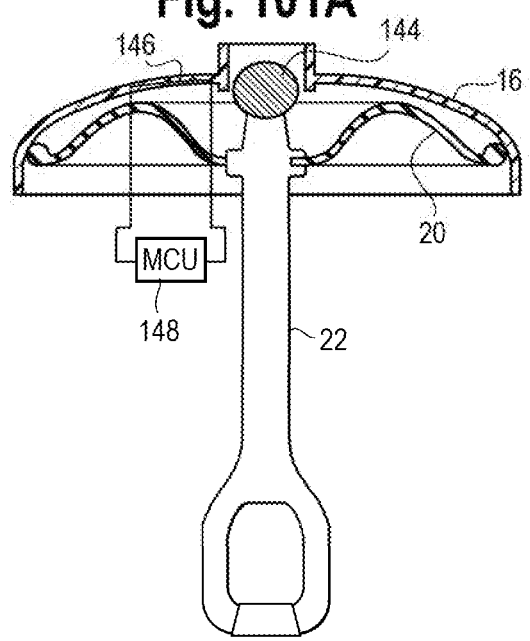
FIGS. 101A and B are cross-sectional views of an actuator and diaphragm in on and off configurations.
Figure 101B:
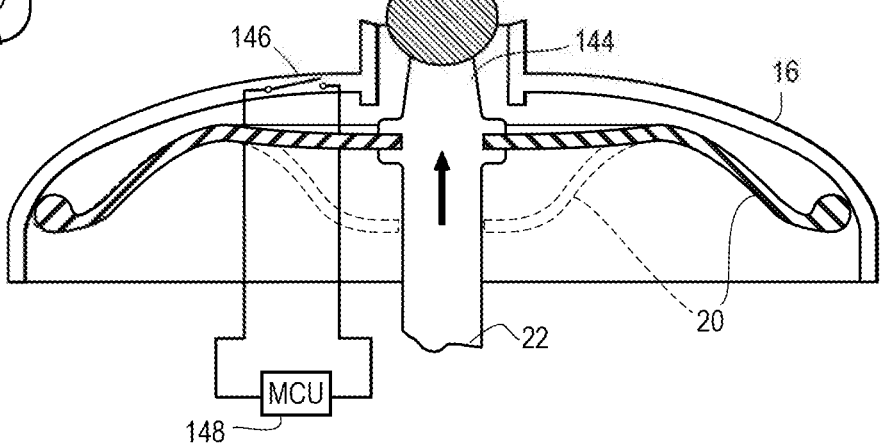

Referring to FIGS. 101A and B, in a reed switch embodiment, a magnetic component 144 is made to be movable relative to a stationary surface. As the magnetic element is displaced it changes the state of a reed switch 146 from ON to OFF or OFF to ON, indicating that activation or deactivation has occurred. In one embodiment, the dome of the actuator 22 is made of a magnetic material, and defines the magnetic component 144, and a reed switch is incorporated into the retainer 16. When the actuator has moved sufficiently, it changes the state of the reed switch, which is recognized by a microcontroller 148 and activation logged. When the actuator 22 moves back to its initial position, the reed switch 146 moves back to its initial state and the microcontroller 148 recognizes that deactivation has occurred. It is important to note that placement of the reed switch and the magnetic component are not limited to this one embodiment. Rather, the reed switch detects actuation and/or deactivation of the nebulizer and the embodiment described was for illustration purposes only.

Inductive Proximity Sensor/Switch

Referring to FIGS. 22A-23B, in one embodiment, a conductive element 150 is built into the moving component of the nebulizer, such as but not limited to, the dome of the actuator 22. A corresponding coil 152 is placed around or near the path that the component moves in, such as the inner diameter of the dial. On inhalation, the moving component (actuator) 22 moves from the OFF position to the ON position, bringing the conductive element 150 of the moving component closer to the coil 152 or loop of the stationary component of the nebulizer. High frequency current is passed though the coil 152 or loop to create an electric field. When the conductive element of the moving component is brought closer or farther away from the loop there is a measurable change in impedance in the coil 152 or loop. This change in impedance can signal when activation has occurred. This feature and principle may be applied to any of the movable components within the nebulizer.

Capacitance Switch

Figure 24:
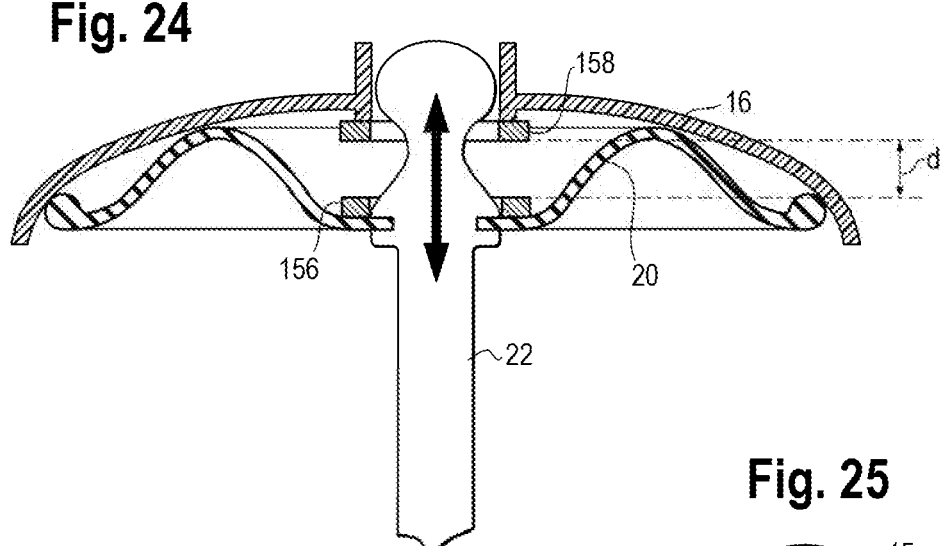
FIG. 24 is a cross-sectional view of one embodiment of an actuator, retainer and diaphragm.
Figure 25:
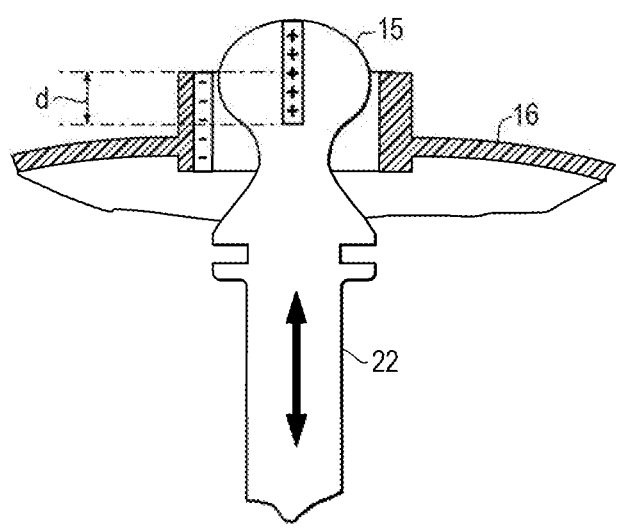
FIG. 25 is a cross-sectional view of an alternative embodiment of an actuator and diaphragm.
Figure 26:
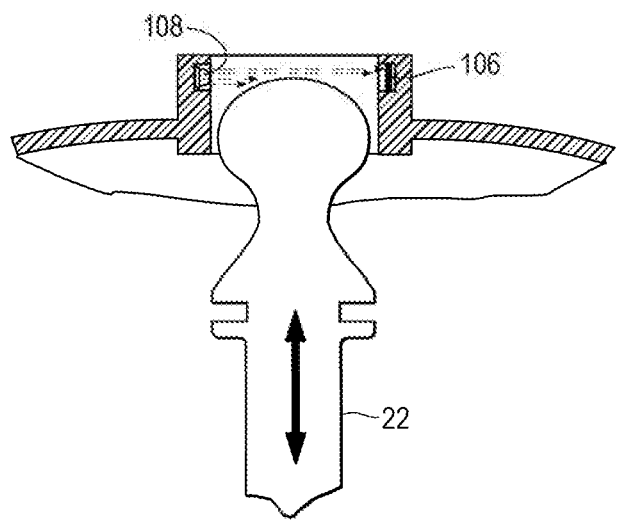
FIG. 26 is a cross-sectional view of an alternative embodiment of an actuator.

Referring to FIGS. 24 and 25, a capacitance switch/proximity sensor 154 may also be used to determine when activation has occurred. Two parallel plates 156, 158 are positioned such that one plate is placed on a "stationary" component of the nebulizer (does not move in response to the breathing cycle) and one plate is placed on a movable component, such as the actuator or diaphragm. The capacitance between parallel plates 156, 158 is dependent on the permittivity of the free space (d), dielectric constant of the material in the gap, overlapping area of the plates and the distance between the plates. If the plates are positioned in an area where the overlapping area of the plates, permittivity of the free space and dielectric constant of the material in the gap are fixed then the changing capacitance is due to the changing distance between the plates. In one embodiment two plates are separated by an air gap. One plate forms a ring around the underside of the dial/retainer while the other plate form a ring on the top surface of the diaphragm, opposite the plate on the dial/retainer. In response to inhalation flow the distance between the plates increases and the capacitance changes. Knowing the relationship between the capacitance and distance allows you to determine the distance the actuator is from the dial, thus if the actuator has travelled sufficiently to produce aerosol. Since the dielectric constant of the material in the air gap is preferably maintained as unchanging, the air gap preferably is not located in the aerosol pathway. Capacitance can be monitored with an oscillator or charge/discharge circuit and changes in frequency indicate aerosol generation has occurred or stopped.

In another embodiment shown in FIG. 25, the distance between the plates 156, 158, the permittivity of the free space and the dielectric constant of the material between the two plates is held constant and the overlapping area of the two plates is varied. One plate is located in the dome of the actuator while the other plate is located in the stationary retainer or dial. On inhalation, the overlapping area of the two plates increases or decreases, depending on their initial positioning. Since the actuator moves axially in the nebulizer, the distance between the plates would remain constant and only the overlapping area would change thus changing the capacitance. Since the dielectric constant of the material in the air gap is preferably maintained as unchanging, the air gap preferably is not located in the aerosol pathway. Capacitance can be monitored with an oscillator or charge/discharge circuit and changes in frequency indicate aerosol generation has occurred or stopped.

Hall Effect

Figure 102A:
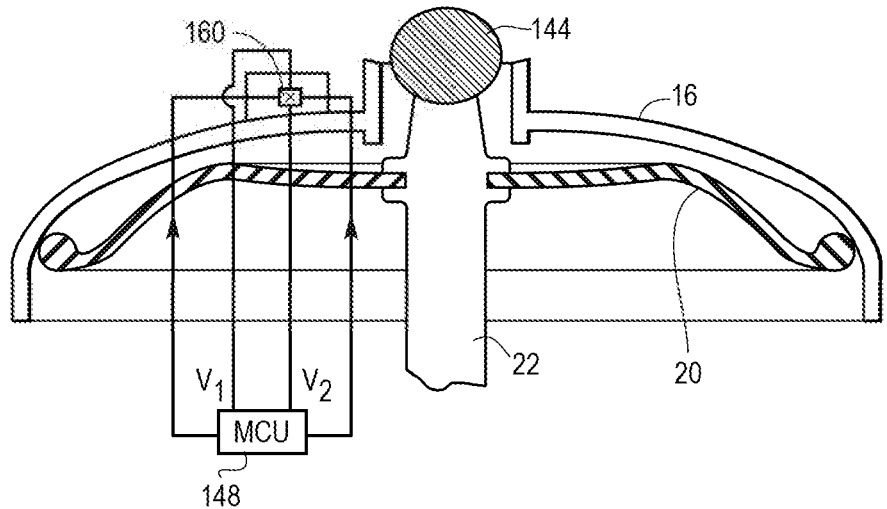
FIGS. 102A and B is a cross-sectional view of an actuator and diaphragm, and a voltage graph.
Figure 102B:
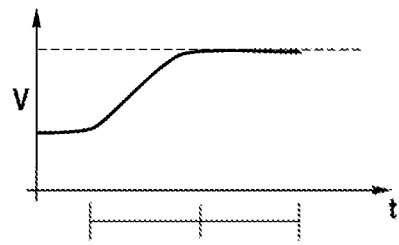
Figure 103A:
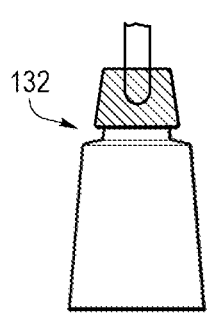
FIGS. 103A and B are cross-sectional views of an actuator with a contact switch.
Figure 103B:
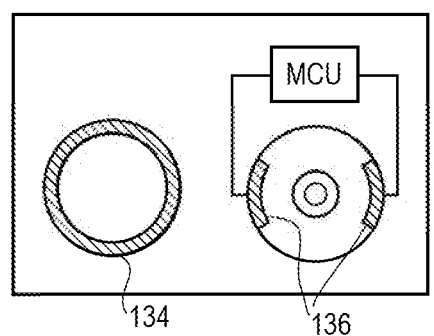

Referring to FIGS. 102A and B, a Hall Effect element 160 may be used to measure the activation and deactivation of the nebulizer. Hall Effect elements work by measuring the voltage of a Hall Effect element, perpendicular to the direction of current flow across the element. In the presence of a magnetic field, a voltage is induced across the element, proportional to the field strength. In one embodiment, a Hall Effect sensor 160 is mounted on the retainer 16 while the dome of the actuator contains a magnetic feature 144. On inhalation, the movement of the actuator 22 may be monitored by a microcontroller 148 measuring the transverse voltage of the Hall Effect element as the proximity of the magnetic dome to the sensor will change the output voltage. When a voltage threshold has been reached the microcontroller can signal that activation has occurred as the actuator has moved sufficiently to generate aerosol. Though this embodiment describes the movement of the actuator bringing the magnet closer to the Hall Effect sensor, an embodiment in which the magnetic component moves away from the sensor on inhalation would also be suitable. Also, the placement of the Hall Effect sensor and magnetic feature are not limited to the retainer and actuator and any Hall Effect element may be used to measure activation and deactivation.

Force Sensing Baffle

Figure 83:
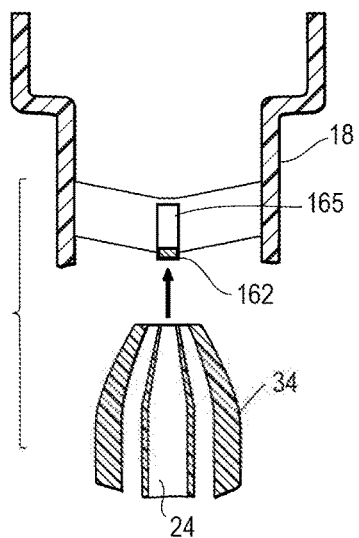
FIG. 83 is a cross-sectional view of one embodiment of a nozzle and baffle.
Figure 84:
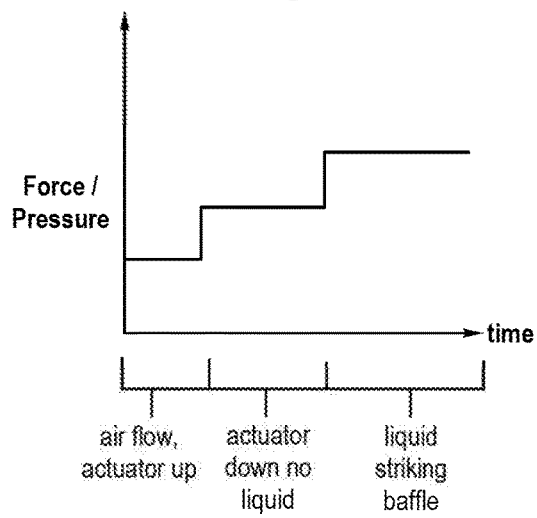
FIG. 84 is a force/pressure graph during a breathing cycle.

Referring to FIGS. 83 and 84, in one embodiment, a force or pressure sensing element 162 is incorporated into the baffle 165. When the actuator is in the OFF position, a reduced flow of air strikes the baffle as a portion of the flow escapes through vacuum break windows in the nozzle cover 34. When the actuator 22 is down, all air flow is directed at the baffle 165 as the windows in the nozzle cover are blocked as well as entrained air through the bottom opening of the nozzle cover. This force increases further when liquid is pulled through the liquid channel and strikes the baffle. This force/pressure reading may be recorded by the sensing element 162 and monitored by a control unit, with an increase over a certain threshold indicating aerosol formation, as shown in FIG. 84 for each of the air flow/actuator up, actuator down/no liquid and liquid striking baffle. This embodiment is capable of being able to differentiate between the patient practicing proper breathing technique while the device is being run dry and when aerosol is being produced.

Humidity

Figure 19:
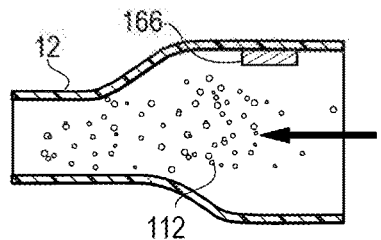
FIG. 19 is a cross-sectional view of one embodiment of a mouthpiece.
Figure 20:
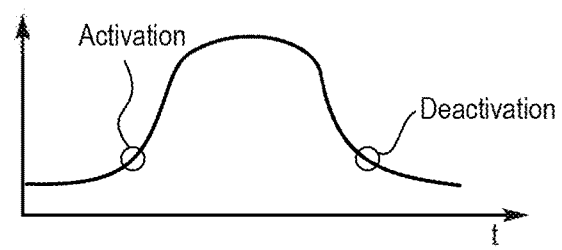
FIG. 20 is a graph of relative humidity v. time during a breathing cycle.

Referring to FIGS. 19 and 20, in one embodiment, a humidity sensor 166 is placed within the nebulizer, in the aerosol pathway 112. One possible location is within the mouthpiece 12 due to its proximity to the patent. Prior to aerosol generation pressured air from a central sir supply or compressor is moving past the sensor. On activation, aerosol generated within the device is collected by compressed and entrained air and flows along the inhalation pathway towards the patient. The air becomes saturated with the liquid droplets of the aerosolized medication and registers as an increase in humidity when it flows past the sensor. When the device deactivates, aerosol generation will cease and the compressed and entrained air flowing past the sensor is no longer saturated with water vapor. With an embodiment such as this, the sensor 166 is preferably calibrated before each treatment for the relative humidity of the environment it is being used in and the source of the compressed air. This calibration could be performed using a second, external humidity sensor. A minimum humidity change in a predefined period of time could be used to detect activation and deactivation however many detection algorithms can be used.

Temperature

Referring to FIGS. 13A-E, in one embodiment, a temperature sensor 168 is placed within the nebulizer, in the aerosol pathway 112. The temperature sensor 168 can determine if device is being supplied with compressed air as the flow of air over the temperature sensor will produce a measurable decrease in temperature when compared to stagnant air. This can be used to "wake" the device from a sleep or low power mode. When the actuator moves into the ON position and aerosol flows along the inhalation pathway (FIG. 13B) there is a decrease in temperature as particles are deposited on the sensor and evaporate. This further decrease in temperature indicates activation has occurred and a continued decreased temperature level signals the duration of aerosol production.

Figure 13A:
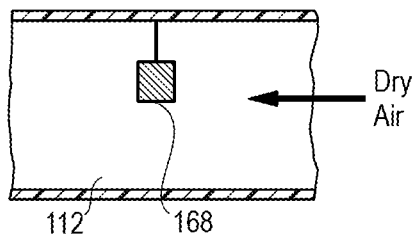
FIGS. 13A-E are flow paths through a nebulizer at various stages of a breathing cycle.
Figure 13B:
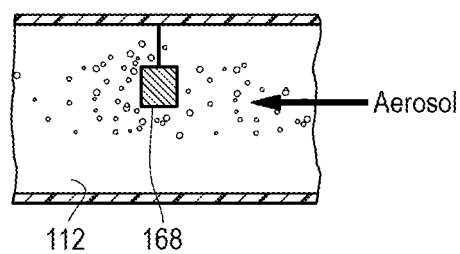
Figure 13C:
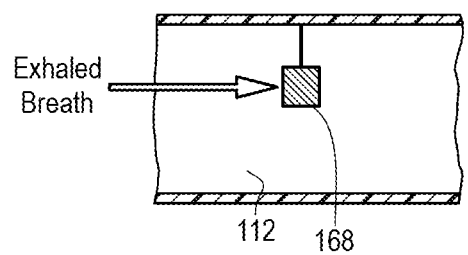
Figure 13D:
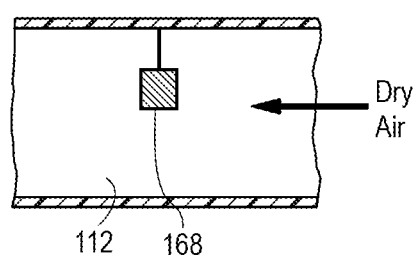
Figure 13E:
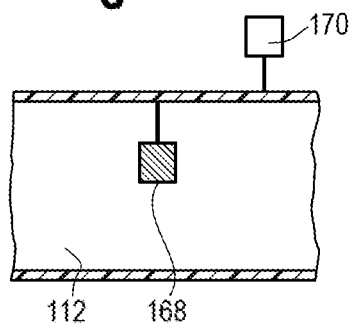

Deactivation can occur in two ways. The first scenario is when the patient exhales through the device (FIG. 13C). This creates positive pressure within the device and the actuator moves to the OFF position. An increase in temperature is experienced due to the cessation of aerosol and the warm, humid air from the patient's lungs passing the sensor. This indicates that activation has stopped. In the second scenario (FIG. 13D), the patient removes their mouth from the mouthpiece to exhale and the lack of a negative, inhalation flow allows the actuator to move back to the OFF position. As before, the lack of aerosol depositing and evaporating off the sensor registers as an increased temperature increase and the system recognizes that deactivation has occurred.

Though the above embodiment describes the pressure sensor being placed directly in the aerosol pathway, the pressure sensor may also be placed elsewhere on the device and measure the local temperature changes. Multiple temperature sensors 168, 170 (see FIG. 13E) may be used to measure relative temperature changes to the external environment in order to improve the accuracy of the system and set reference temperatures.

Capacitance—Dielectric Constant of Aerosol

Figure 21:
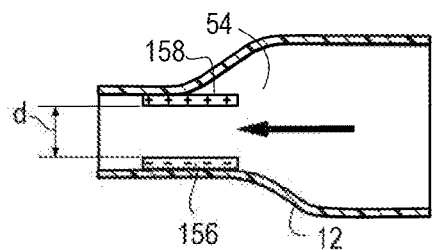
FIG. 21 is a cross-sectional view of one embodiment of a mouthpiece.

Referring to FIG. 21, assuming the dielectric constant of the aerosol is different than that of air, a capacitive sensing method can be used to determine when activation has occurred. A capacitor 154 can be created by separating two conductive materials 156, 158 by an insulating air gap, for example in a flwo pathway 112 of a mouthpiece 12. The air gap is situated such that on aerosol production, aerosol flows through the gap. If the aerosol does have a different dielectric constant than air than the presence of aerosol between the conductive change will result in a measurable change in capacitance. Capacitance can be monitored with an oscillator or charge/discharge circuit and changes in frequency indicate aerosol generation has occurred or stopped.

Flow

Measuring the flow through the device is not a direct method of determining when activation takes place but using known performance characteristics of the device, such as the known flow to actuate, actuation may be registered. Measuring flow is also important for monitoring of the breathing pattern of the patient over the course of the treatment. As such, all embodiments and methods covered in the next section, Measuring Flow, are also applicable in determining when activation has occurred.

It is important to note that the various embodiments and methods disclosed herein may be combined to register actuation. Indeed, combinations of any of these techniques is contemplated as the different embodiments/techniques can be linked together to improve the accuracy and expand the capability of the nebulizer system.

Measuring Flow/Breathing Pattern

It would be advantageous for a smart nebulizer to be able to monitor the inhalation and exhalation of the patient over the course of their treatment. Proper breathing techniques, especially inhalation, can optimize drug delivery to the lower airways. Too forceful of an inhalation can result in impaction of even respirable particles in the upper airways. Real time feedback of inhalation flow rate would allow the smart nebulizer system to provide a breathing coach feature that guides the breathing cycle of the patient/user to ensure that the patient/user receives the ideal dosage. Various electronic devices are available for measuring flow, including internal sensors that may be placed within the nebulizer, external sensors and standalone devices that are capable of interpreting operating characteristics of the nebulizer and relating these signals into the flow through the device. The breath monitoring embodiment and method may be adaptable and able to determine flow when used with a variety of air supply sources at varying pressures. The breath monitoring embodiment is preferably robust enough to reject environmental noise and isolate the signal of interest.

Sound Based Approach

Intrinsic Sound

Figure 29:
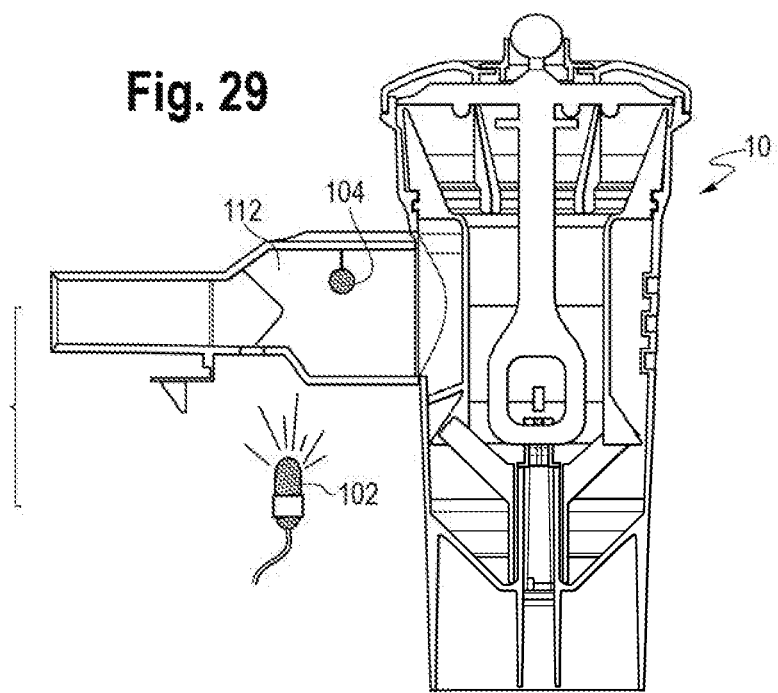
FIG. 29 is a cross-sectional view of one embodiment of a nebulizer.
Figure 30:
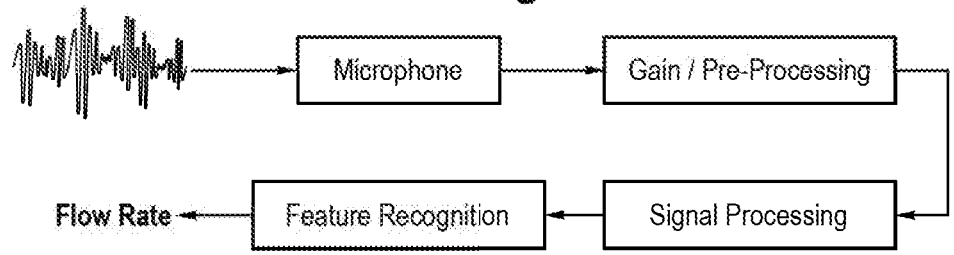
FIG. 30 is a flow chart showing the calculation of flow rate using a microphone.

Referring to FIGS. 29 and 30, a microphone 104 may be used to measure the intrinsic sounds produced by the device when flow is moving through it. The airflow pathway 112 within the nebulizer is often purposely torturous to control the aerosol particle size. This creates turbulent flow that must pass around complex, blunt geometry. With an increased flow there is a corresponding increase in the turbulence experienced and a change in the intrinsic sounds produced by the device. A microphone may be placed within the device, on the outer surface or as a standalone sensor to detect the sound caused by the airflow through the nebulizer. Through experimental testing the relationship between the detected sound and flow rate can be determined. Many signal processing and analysis techniques are available to relate the microphone data to flow such as a simple volume threshold to more complex frequency domain analysis techniques. The sound is not limited to that which is detectable by the human ear and a wide frequency band can be used.

The intrinsic sound based flow measurement techniques are not limited to using a single microphone and multiple microphones 102, 104 can be used to improve the accuracy of the flow measurement as well as to capture environmental noise.

Generated Sounds

Figure 31:
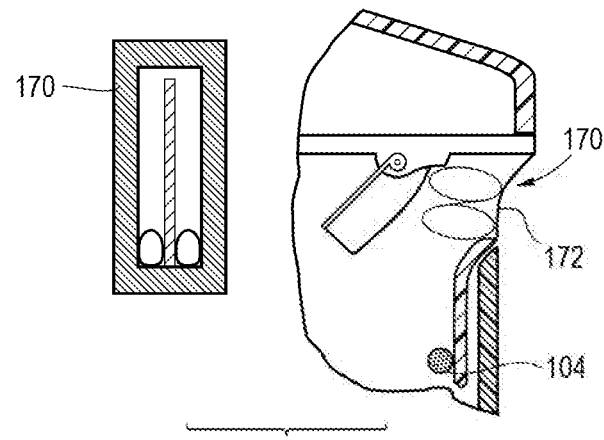
FIG. 31 is a partial cross-sectional view of an inhalation window.

Referring to FIG. 31, much like an intrinsic sound approach, a single microphone 104 or multiple microphones are used to detect sounds purposely produced by the nebulizer using special geometry 170 that emits a sound when airflow passes over it, much like the FLOWSIGNAL flow indicator in the AEROCHAMBER aerosol holding chamber. In one embodiment, sound producing geometry 170 such as a reed is placed in front of the inhalation windows 172 of the nebulizer. Alternatively, the sound producing geometry is molded into the inhalation window itself. On inhalation, air is drawn through the sound producing geometry and produces a known sound. The volume change or frequency shift caused by a varying flow rate can be recognized by the sound sensing unit of the nebulizer system and related to flow rate. A similar component can be added to the exhalation ports to recognize exhalation flow rates. The measurement of flow using generated sound is not limited to placement at the inhalation and exhalation windows and can be placed anywhere within the device that is in the inhalation and exhalation pathway. Different tones may be produced for each flow path in order to distinguish inhalation and exhalation flows. As with the intrinsic sounds methods, the generated noise is not limited to the audible range of humans.

Doppler

Figure 32:
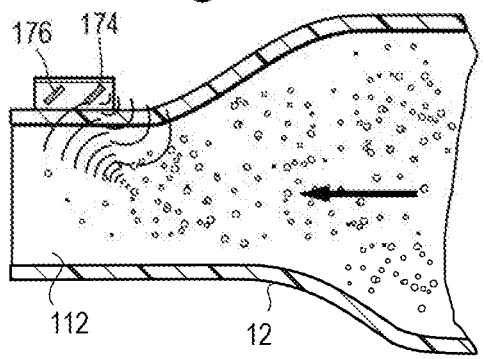
FIG. 32 is a cross-sectional view of one embodiment of a flow path.

Referring to FIG. 32, the Doppler Effect may be used to measure the velocity (and flow rate) of passing particles in the nebulizer. A transmitter and receiver unit 174, 176 are placed such that in the presence of aerosol the sound produced by the transmitter is reflected back at the receiver. This can be achieved by directing the transmitter and receiver at an angle to the flow path. Due to the velocity of the aerosol that is reflecting the sound, there is a shift in the frequency in the received sound. If the particles are moving opposite the direction of the transmitted sound, the reflected sound wave will be more compressed and therefore at a higher frequency. The level of the frequency shift can be related to the velocity of the particles. Knowing the cross sectional area of the gas flow allows for the calculation of flow rate using the velocity. This method works for flows in both directions except the received sound will have a lower frequency than the transmitted wave. It is important to note that this method requires the presence of aerosol to act as a reflecting agent. As such, this method may also be used to detect activation but may be unable to determine the flow rate of the dry air in the nebulizer prior to activation.

In one embodiment, the transmitting and receiving components are placed adjacent to each other on the wall of the mouthpiece. The transmitter and receiver are angled so that the signal is projected at an angle along the flow pathway and is not emitting perpendicular to the flow. This method is not limited to any one frequency range though it is often used with ultrasonic signals.

Time of Flight/Transit Time

Figure 33:
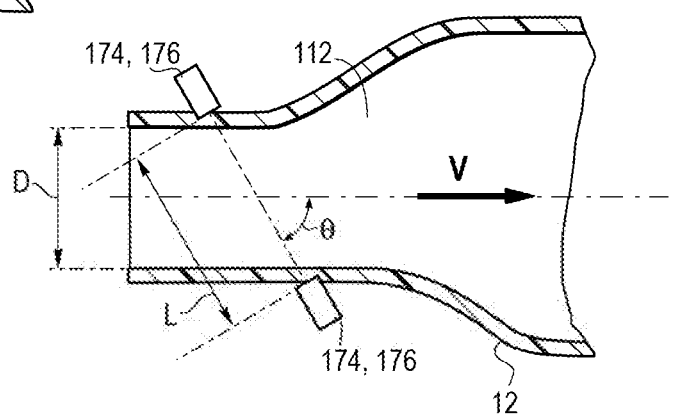
FIG. 33 is a cross-sectional view of one embodiment of a mouthpiece.

Referring to FIG. 33, in a time of flight or transit time flow measurement embodiment, two transmitter and receiver components 174, 176 are placed on opposing faces of a cylindrical element through which air flows. The sensors are placed at an angle $\Theta$ to the flow pathway with each transmitter/receiver of each component facing the other. In one embodiment this cylindrical element would be the mouthpiece. Sound is emitted by each component during opposing time intervals and the time it takes for the sound to reach the opposing sensor is calculated. Knowing the time of flight between the sensors in both directions gives an average velocity of the flow that is independent of the gas or particles passing through the air channel. Knowing the geometry of the nebulizer and the velocity allows for a calculation of the flow rate.

Pressure Based Approach
Pressure Relative to Atmospheric

Figure 34:
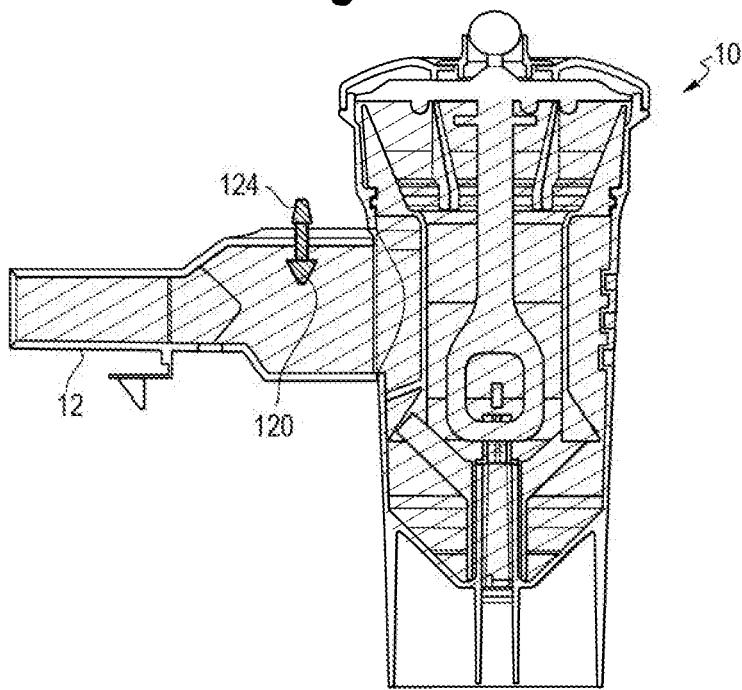
FIG. 34 is a cross-sectional view of one embodiment of a nebulizer.

Referring to FIG. 34, in one embodiment a pressure sensor 120 is placed within the device to measure the internal pressure. The sensor must be placed inside the closed system formed when the patient places their mouth on the mouthpiece. This is the region that changes pressure in response to the patient's breathing, for example in the mouthpiece 12. On inhalation the internal pressure of the nebulizer becomes negative relative to atmosphere and flow is drawn through the inhalation valve and into the patient's lungs. With increasing flow also comes a greater vacuum as flow of air into the nebulizer is limited by the inhalation valves restricting the inhalation ports. As a result, increasing airflow requires greater effort by the patient. On exhalation the pressure within the nebulizer becomes positive and increases with increasing exhalation flow as exit from the device is limited by the size of the exhalation ports and the valves covering them. A relationship exists between the internal pressure and flow rate though it is marginally dependent on the characteristics of each valve and possible leakages in the nebulizer. A second pressure sensor 124 may be included to measure atmospheric pressure and results in a more robust design that is capable of accurate internal pressure measurement, independent of the external environment.

Venturi

Figure 35:
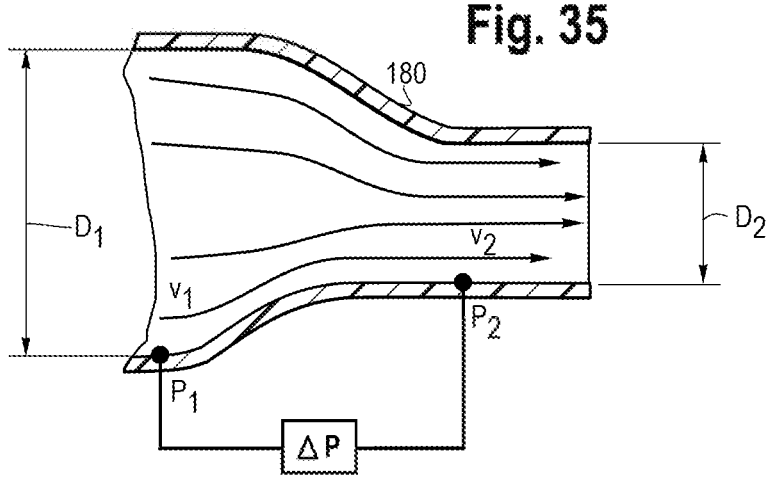
FIG. 35 is a cross-sectional view of one embodiment of a flow path.
Figure 36:
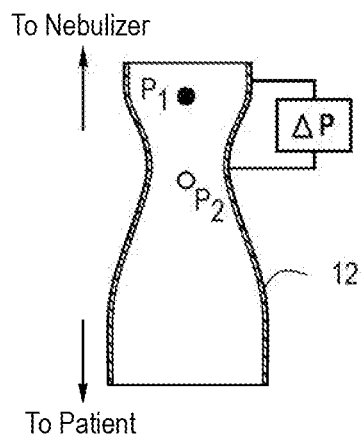
FIG. 36 is a cross-sectional view of one embodiment of a flow path.
Figure 37:
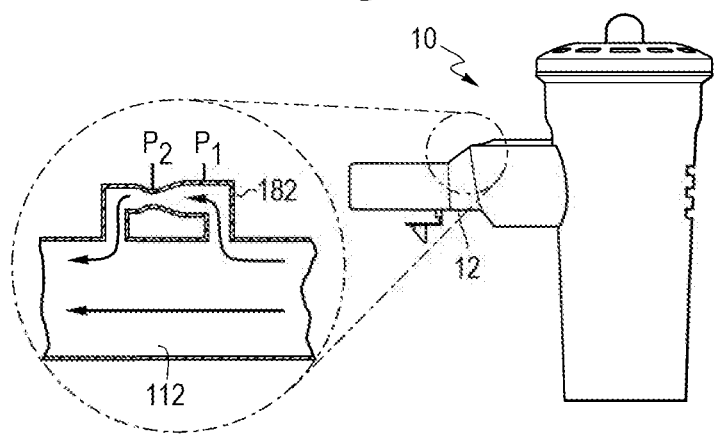
FIG. 37 is a cross-sectional view, with enlargement, of one embodiment of a nebulizer.
Figure 38:
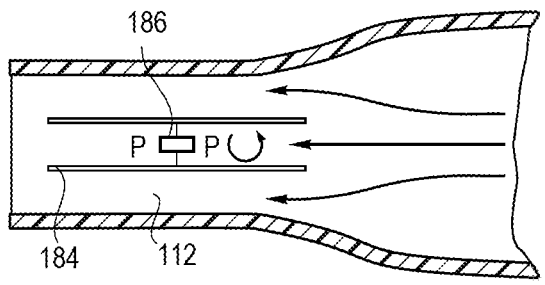
FIG. 38 is a cross-sectional view of one embodiment of a flow path.
Figure 39:
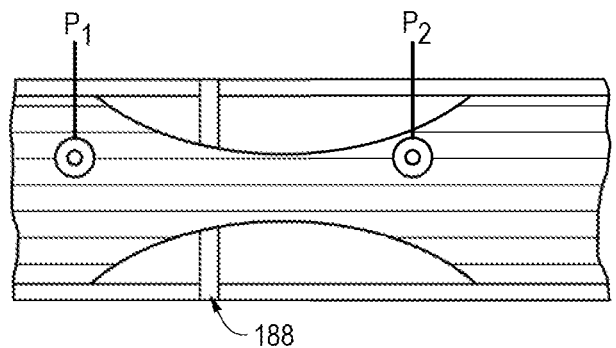
FIG. 39 is a cross-sectional view of one embodiment ora flow path.
Figure 40:
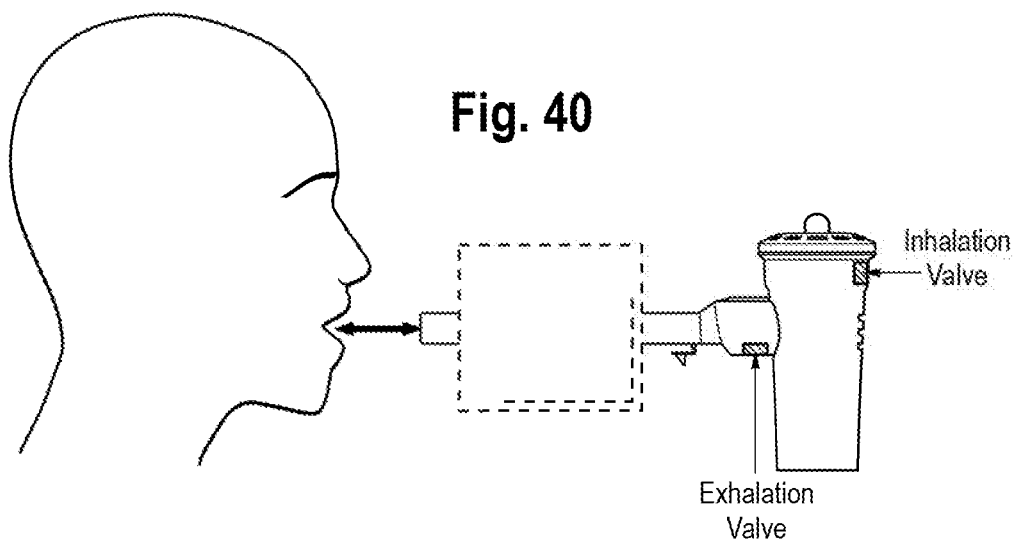
FIG. 40 is a side view showing a patient with one embodiment of a nebulizer.
Figure 41:
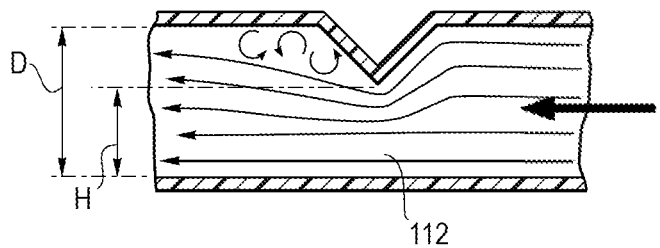
FIG. 41 is a cross-sectional view of one embodiment of a flow path.
Figure 42:
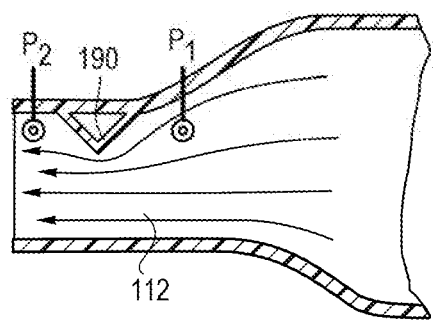
FIG. 42 is a cross-sectional view of one embodiment of a flow path.
Figure 43:
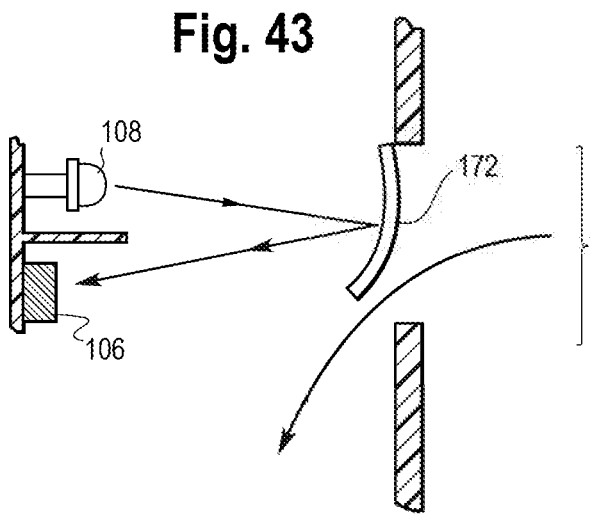
FIG. 43 is a view of a flow path through one embodiment of a valve.
Figure 44:
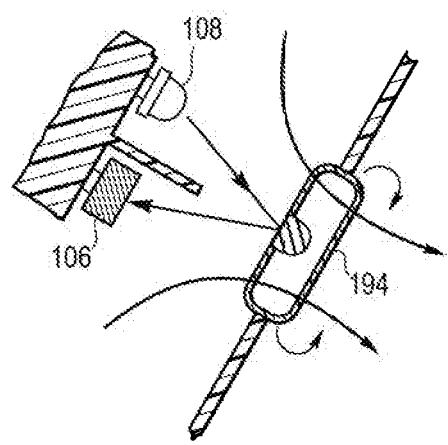
FIG. 44 is a view of a flow path through one embodiment of a valve.

Referring to FIG. 35, the Venturi Effect can be used to measure flow by creating a Venturi tube 180 within the nebulizer that forces a pressure drop in an area with known geometry. A cylindrical tube is created that has a smooth transition from one diameter to another with known cross sectional areas. Assuming the flow is steady state and laminar, and that the compression of the gas is minimal, conservation of mass requires that the velocity must change to maintain the same flow rate. Based on the Bernoulli equation this creates a local pressure drop. The pressure drop can be measured and the flow rate calculated.

A Venturi geometry is incorporated into a portion of the nebulizer such as the mouthpiece 12 as shown in FIG. 36 to create a measurable pressure drop that is recorded as a differential pressure. The disadvantage of this method is the narrowing of the mouthpiece accelerates the aerosol and provides them with more momentum, potentially increasing impaction in the upper airways.

Alternatively, a bypass Venturi tube 182, as shown in FIG. 37, is created off of the main airflow pathway that a portion of the flows moves through. The flow through this portion of the mouthpiece is correlated to the flow of air through the main body. The mouthpiece includes the basic geometry of a cylinder transitioning to a smaller diameter, and may create a measurable localized pressure drop for this embodiment.

Pitot Static Tube

Referring to FIG. 38, in a pitot static tube embodiment, an area of stagnation is created in the flow path typically using a cylindrical shaped geometry 184 with one closed end. The open end of the cylindrical tube faces the incoming flow. A pair of tubes 184 may face in opposite directions. A pressure sensor 186 is placed within the tube usually on the inner side of the closed face. In the presence of airflow a portion of the flow enters the tube and stagnates, building up pressure within the tube. With greater flows rates there is an increased pressure within the tube as the air experiences a greater deceleration and imparts more force on the sensor. This pressure profile can be characterized though testing and a relationship between the pressure in the pitot static tube and flow created. A second sensor may also be placed to measure atmospheric pressure for reference and calibration purposes.

In one embodiment, two pitot static tubes may be placed in the mouthpiece, with the tubes facing in opposite directions of flow. On inhalation, one Pilot tube will experience an increase in pressure while the other would see no change or a small decrease in pressure. This embodiment has the advantage of not only measuring flow but also the direction of flow within the nebulizer.

Restricted Orifice

Referring to FIGS. 39 and 40, similar to the Venturi tube, a restricted orifice method of measuring flow uses a change in cross sectional area to force a measurable pressure drop. Unlike the Venturi embodiment, the restricted orifice 188 is an abrupt change in cross sectional area which allows for a greater change in pressure. However, the restricted orifice results in greater acceleration of the aerosol and disturbs the flow path. In addition, the abrupt change in cross sectional area may increase the impaction of the aerosol. Unlike the Venturi flow measurement, the restricted orifice provides a bidirectional pressure measurement. The restrictive orifice is positioned between the patient/user 183 and any valving or leaks such that it is measuring flow into and out of the patient's lungs.

As shown in FIG. 40, the user 183 has positioned the mouthpiece in their oral cavity. It should be understood that the same depiction applies to all other embodiments disclosed herein, meaning those embodiments are also positioned in the user's mouth during use.

Wedge Flow Measurement

Referring to FIGS. 41 and 42, while similar to the restricted orifice embodiment, one side of the flow path is restricted with a triangular shaped cross-section, or wedge 190, for example within a cylindrical shaped flow path of the mouthpiece 112. The cross section creates a lower pressure differential then a restricted orifice and therefore disrupts the flow less. This embodiment is applicable to air flow that has a low Reynolds number (laminar flow). As with the restricted orifice, this embodiment provides a bidirectional method of measuring flow. In one embodiment, the flow restriction is placed within the mouthpiece having a cylindrical shape, in part because the flow is the least turbulent at this point in the nebulizer.

Light Based Methods

Reflectance—Internal

Referring to FIG. 43, a light source 108 and sensor 106 can be placed adjacent to one another but separated by opaque material such that no direct light from the light source can reach the sensor. The source and sensor are both directed in the same direction towards a component of the nebulizer that moves in response to flow and the degree to which the member moves is dependent upon the flow rate. For illustration purposes, an embodiment that uses the existing inhalation and exhalation valves 192, 194 will be described. When the patent is not breathing through the device the valves are closed and much of the light is reflected off of the valve and back to the light sensor. On inhalation the inhalation valves 192 curl in response to the flow and some light is allowed to pass through the inhalation windows while some is still reflected back to the sensor. As inhalation flow increases so too does the curl angle of the valve and less light is reflected back to the light sensor. The same process happens on exhalation as the exhalation vales 194 moves away from the valve seat with exhalation flow. A relationship may be determined between flow and the intensity of light received by each light sensor. This embodiment has the benefit of being able to determine the direction of flow as a reduced reflectance from the inhalation valve indicates inhalation flow and vice versa. This embodiment and method is not exclusive to the existing inhalation and exhalation vales and may be expanded to any component that moves in response to flow and whose degree of movement is dependent upon the flow rate. This embodiment and method is applicable to all wavelengths of light and all filtering methods.

Shine Through

Figure 45A:
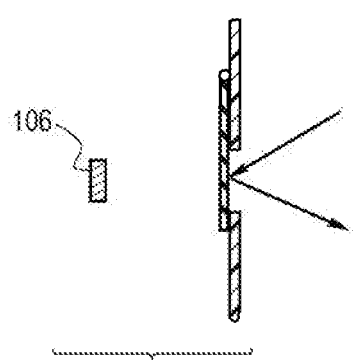
FIGS. 45A and B are views of a flow path with a valve in closed and open positions respectively.
Figure 45B:
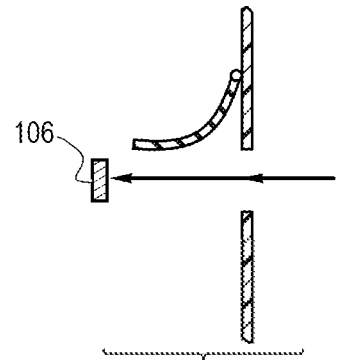
Figure 46:
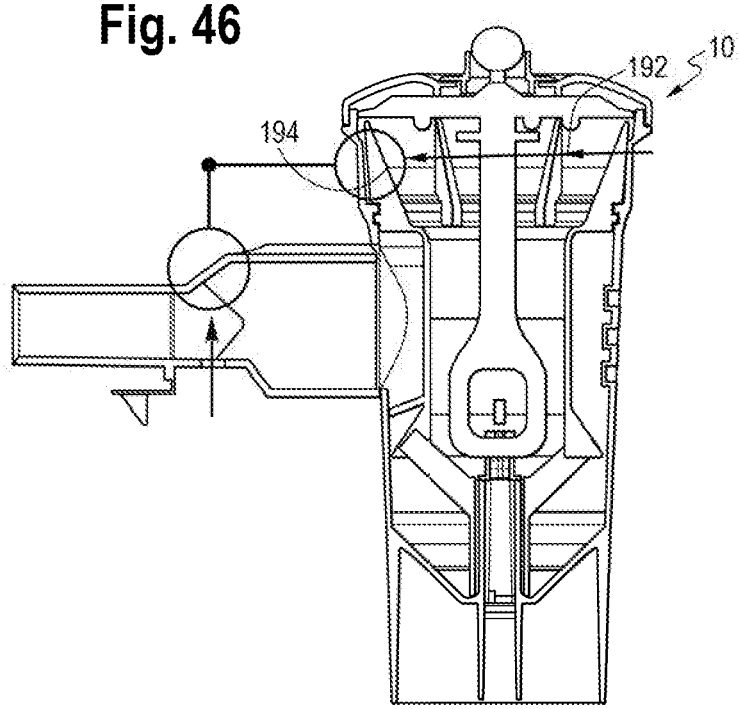
FIG. 46 is a cross-sectional view of one embodiment of a nebulizer.

Referring to FIGS. 45A and B, a light source 108 and sensor 106 are placed on opposite sides of a component 192 that moves in response to flow and restricts the intensity of light that reaches the sensor. The light source can be ambient or generated by a source such as an LED. It is also applicable to all wavelengths of light and is not restricted to the visible spectrum. With increasing flow there is an increasing degree of movement by the moveable component. This allows for increased amount of light to pass through to the sensor. A relationship may be determined between the light intensity registered by the light sensor and the flow rate. As described with respect to the Reflectance—Internal embodiment, one embodiment uses the existing inhalation and exhalation valves (FIG. 46) with a light sensor placed opposite the valves such that on inhalation and exhalation the movement of the valves allow light to pass through to the light sensor.

Oscillating Member

Figure 47A:
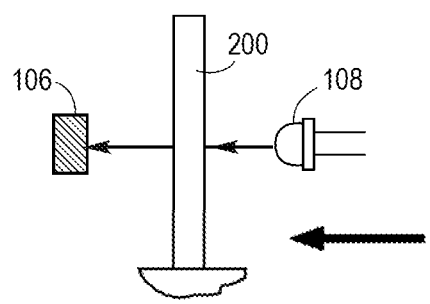
FIGS. 47A-C are schematic representations of various flow paths.
Figure 47B:
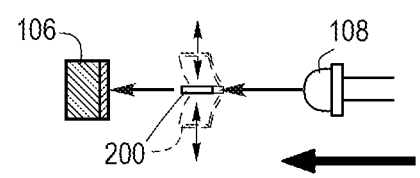
Figure 47C:
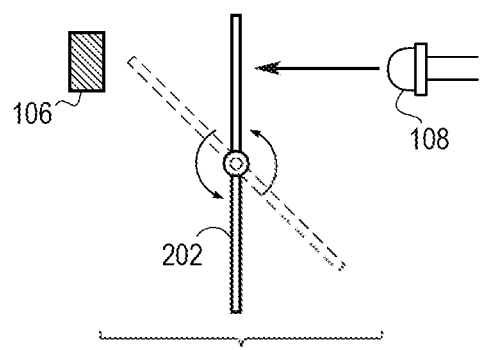

Referring to FIGS. 47A-C, an opaque oscillating component 200 is placed within the flow path 112 with a light source 108 and sensor 106 on either side. When there is flow present the oscillating component moves at a frequency that is unique to the flow rate. The oscillation of the component periodically blocks the path between the light source and sensor. The frequency at which it does so can be related to flow rate. A vibrating element such as a reed 200 could be used (with the reed 200 in one embodiment moving side-to-side (FIG. 47B), or a rotary component 202 (FIG. 47C) such as a pinwheel. However, this embodiment/method is not limited to these two oscillating components, but rather is applicable to any component that moves at a set frequency in the presence of flow and periodically blocks the transmission of light to a sensor.

Temperature Based Methods

Hot Wire Anemometer

Figure 48:
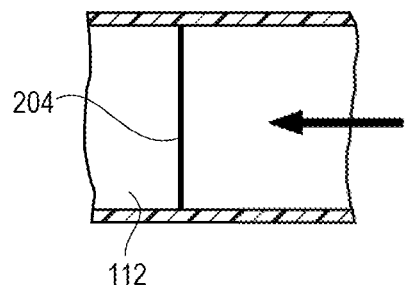
FIG. 48 is a cross-sectional view of one embodiment of a flow path.

Referring to FIG. 48, a wire 204 is heated electronically and placed within the flow path 112. As air flows past the wire 204, the wire is cooled and the resistance of the wire changes. The circuitry used to measure the temperature change can be constant current, constant voltage or a pulse-width modulation configuration. All methods effectively measure the temperature change and may be related to the air flow through experimentation. This embodiment may include any thermistor or thermocouple that is positioned internally in the device.

Thin Film Thermal Sensor

Figure 49A:
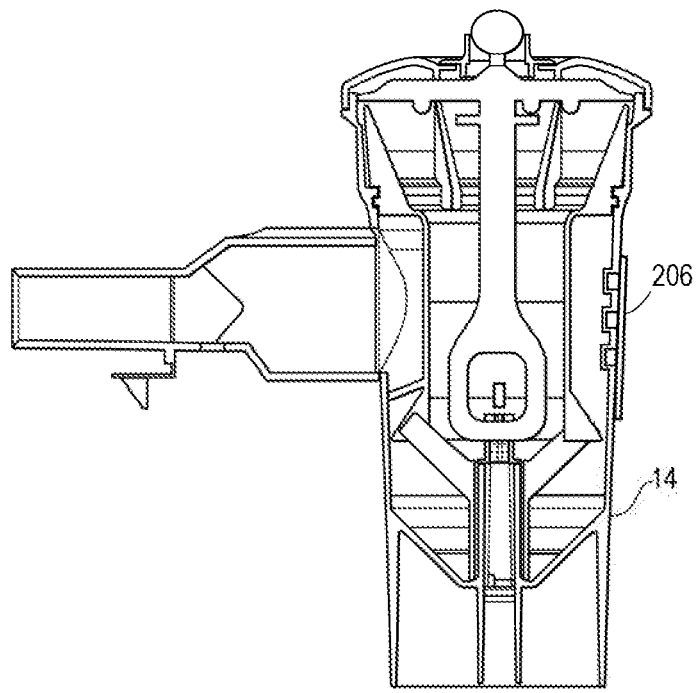
FIGS. 49A and B are cross-sectional and perspective views of one embodiment of a nebulizer respectively.
Figure 49B:
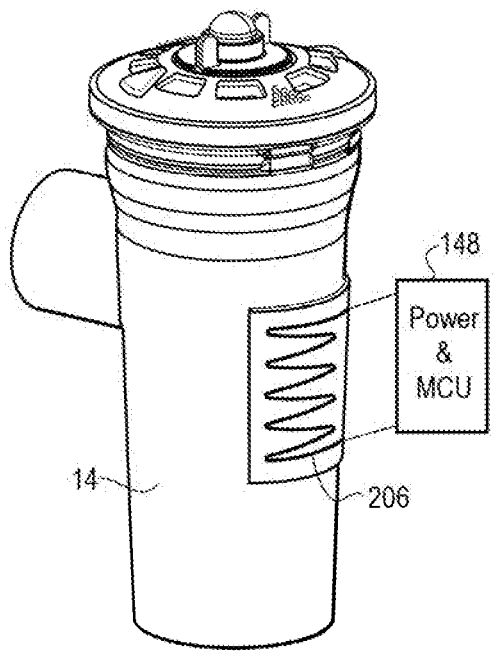
Figure 50:
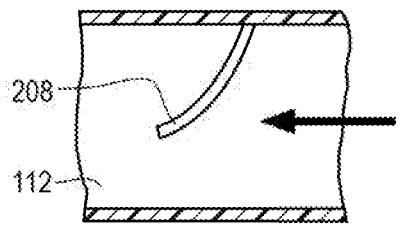
FIG. 50 is a cross-sectional view of one embodiment of a flow path.
Figure 51A:
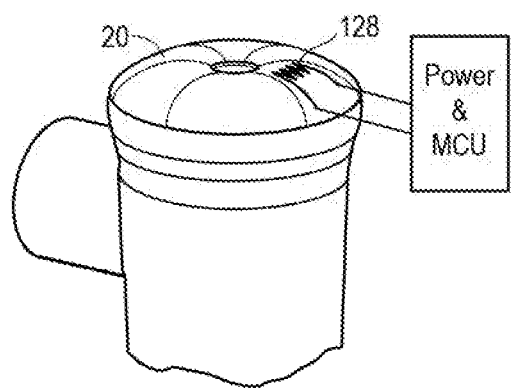
FIGS. 51A and B are perspective views showing a diaphragm during non-inhalation and inhalation respectively.
Figure 51B:
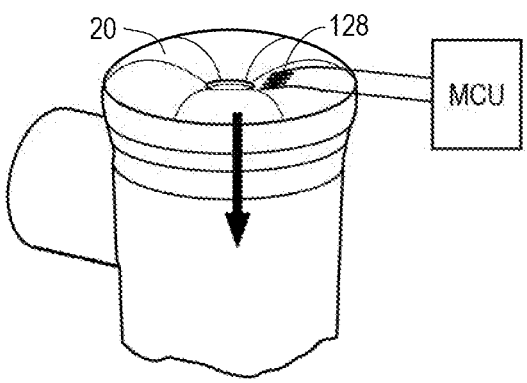
Figure 52:
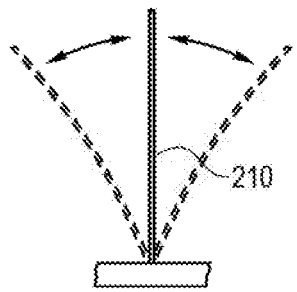
FIG. 52 is a side view of a vibratory sensing element.
Figure 53:
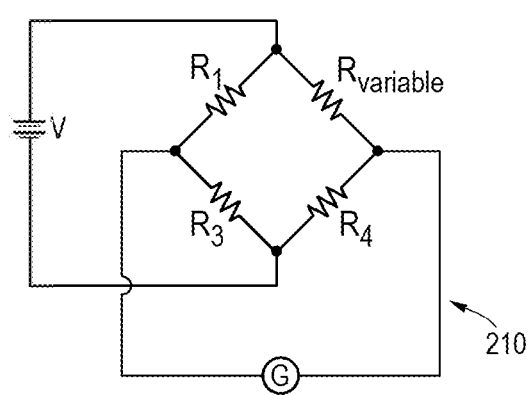
FIG. 53 is a view of a sensing circuit.
Figure 54:
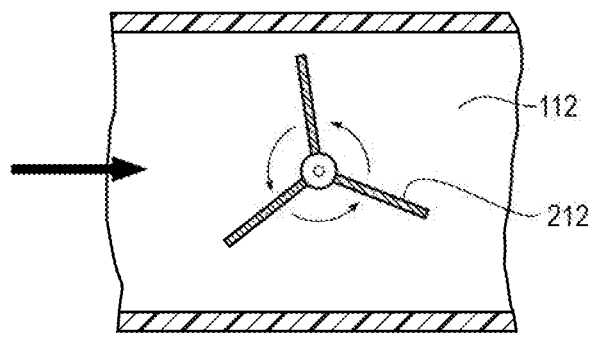
FIG. 54 is a cross-sectional view of one embodiment of a flow path.

Referring to FIGS. 49A and B, a thin film sensor 206 is placed on the internal or external surface of the device (not in the flow path), for example on the outside of the bottom housing 14. When air is flowing in the nebulizer it cools the surfaces of the device and as in the Hot Wire Anemometer configuration, causes a measurable change in resistance in the sensor which may be monitored by, but not exclusively, a microcontroller 148. This embodiment should take into account that the temperature of the nebulizer is also related to the presence of aerosol, and that the response time may be slower as the thermal transfer must occur in the body of the device for the temperature change to be detected by a thin film placed on its surface.

Strain/Flex Sensor

Deflection

Referring to FIG. 50, air flowing past an element 208 in the airflow pathway 112 exerts a force on the element. Increases in airflow also increase the force exerted as the particles experience a greater deceleration when they strike which is directly related to the force they exert. By placing a flex sensor 208 in the airflow path it is possible to calculate the air flow rate based on the level of the deflection of the flex sensor. The level of deflection is related to flow rate through experimentation.

This may also be applied to the existing inhalation and exhalation valves, which respond to inhalation and exhalation flows, with their level of deflection related to the flow entering or exiting the nebulizer. A strain gauge may be printed on the existing valve surfaces to measure their level of deflection which can then be related to flow. Alternatively, the existing valves themselves could be replaced with flex sensors that control the rate and direction of flow.

The flex sensor may be resistance based or made of piezoelectric material. In a resistance based embodiment the deflection of the sensor causes a change in resistance that may be monitored by a control unit using a variety of methods. In a piezoelectric embodiment the deflection of the sensor creates a voltage that is proportional to the amount of deflection.

Strain on Diaphragm

Referring to FIGS. 51A and B, in one embodiment, one or multiple strain gauges 128 are integrated into the biasing element 20, e.g., diaphragm, of the nebulizer to measure the strain experienced by the flexible material. The biasing element may be a spring geometry formed by the silicone diaphragm. On inhalation the diaphragm 20 responds to changes in internal pressure and is pulled down in order to activate the actuator. With increasing inhalation airflow there is an increase in the vacuum pressure and even though the position of the actuator is restrained by the nozzle cover, the diaphragm is continually pulled down and strained further. The level of strain experienced may be related to the inhalation flow rate. On exhalation there is a buildup of positive pressure within the device which also strains the diaphragm and may be related to the exhalation flow rate. Using this embodiment in conjunction with activation/deactivation detection would allow the nebulizer system to determine flow rate and the direction of flow.

Oscillating

Referring to FIGS. 52 and 53, an oscillating component 210 is placed in the air flow pathway 112 that will oscillate at a frequency that is proportional to the flow rate. The component may be composed of a resistive flex sensor that changes impedance on deflection or a piezoelectric material that generates a voltage on deflection. The frequency of the oscillation may be monitored by a control unit that can relate the frequency to flow rate through a relationship determined through experimentation.

Turbine Flowmeter

Referring to FIG. 54, a rotor or pinwheel 212 is placed within the flow path 112. Flow causes the rotor or pinwheel to rotate at a frequency that is related to the flow rate. Rotational speed of the turbine can be measured with many methods such as through Hall Effect elements to detect the passing rotor blades, a contact switch or the breaking of a light curtain. It is important to note that determining the rotational speed of the turbine is not limited to the methods listed here. This method is advantageous as it does not cause a significant pressure drop. However, placing a turbine in the aerosol pathway may increase aerosol impaction and reduce drug output.

Displacement

Figure 55:
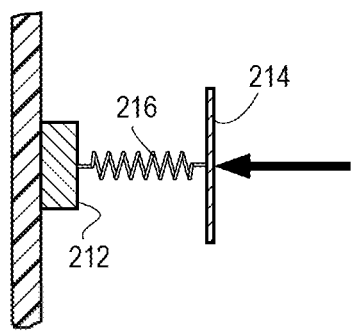
FIG. 55 is a cross-sectional view of one embodiment of a flow path.
Figure 61:
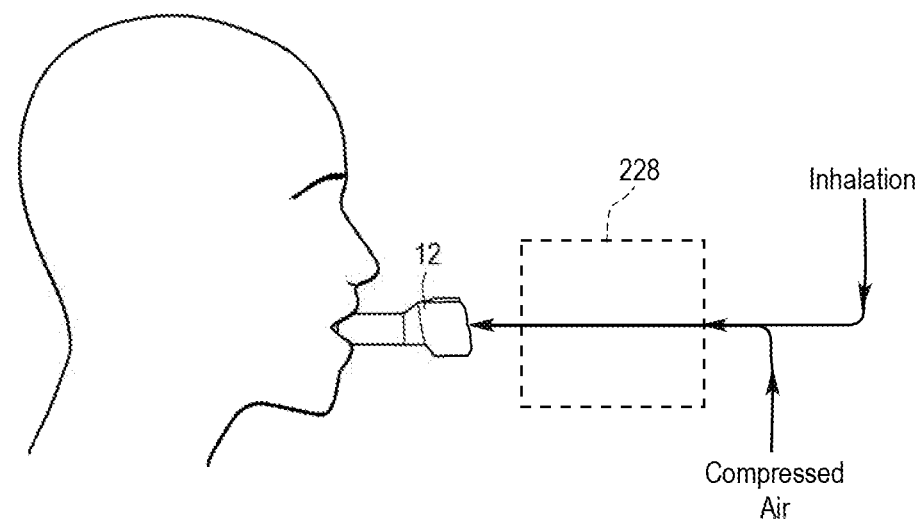
FIG. 61 shows an exemplary schematic of various flow paths in a nebulizer.

Referring to FIG. 55, all methods of measuring displacement have at least two common elements: (1) a stationary component 212 that does not responds to inhalation and exhalation flow; and (2) a moveable component 214 that moves in one axis on inhalation and exhalation. Various embodiments may include a third element: (3) a connecting component connecting the stationary and movable components, such as a spring 216 (linear or non-linear) that returns the movable component to a steady state position when there is no air flow. On inhalation the flow of air moves the movable component relative to the stationary one. A greater flow rate produces a greater displacement as the airflow experiences great deceleration when it strikes the movable component, thus exerting a greater force. The configuration may allow for unidirectional or bidirectional movement depending on the type of spring used which would allow for one configuration to be able to measure both inhalation and exhalation flow rate. As shown in FIG. 61, the displacement is preferably measured in a region 228 between the user/patient and any deviations in the airflow pathway, for example in the mouthpiece.

In various embodiments, disclosed below, the displacement flow rate measurement techniques rely on a measurement of local flow, and are typically positioned between the oral interface and any deviations in the airflow pathway. Leaks and exhalation and inhalation pathways are examples of these deviations. By placing the sensing unit in this area, the airflow experienced by the patient can be measured directly. The sensing element may be placed elsewhere in the nebulizer system, however there no longer is a direct measurement of the flow experienced by the patient.

Hall Effect

Figure 56:
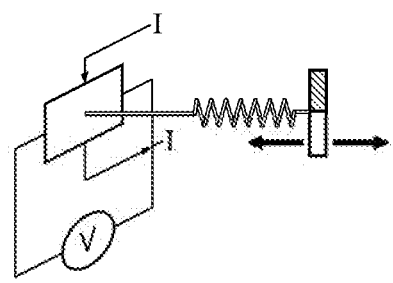
FIG. 56 is a cross-sectional view of one embodiment of a flow path.

Referring to FIG. 56, a Hall Effect sensor 212 is at a stationary position and the movable component 214 is comprised of magnetic material. A spring 216 connects the two components. On inhalation the flow exerts a force on the magnetic element and moves it closer to the Hall element, and produces a change in the magnetic field that is measurable. This change may be related to the displacement of the magnetic component and thus the air flow. On exhalation the element moves further away from the Hall element. Though the embodiment above describes the magnetic element moving closer on inhalation and further on exhalation, the opposite orientation would accomplish the same task.

Capacitance

Figure 57:
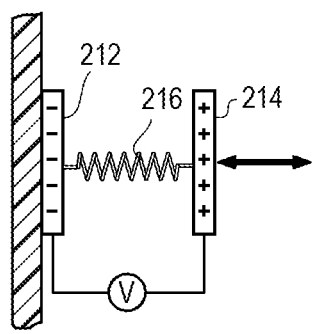
FIG. 57 is a cross-sectional view of one embodiment of a flow path.

Referring to FIG. 57, a capacitance switch/proximity sensor method may also be used to determine the displacement of the movable component in relation to the stationary one. Two parallel plates 212, 214 are positioned such that one plate 212 is placed on a "stationary" component of the nebulizer (does not move in response to the breathing cycle) and one plate 214 on a movable component with the two plates connected by a non-conductive biasing element such as a spring 216. The capacitance between parallel plates is dependent on the permittivity of the free space, dielectric constant of the material in the gap, overlapping area of the plates and the distance between the plates. If the plates are positioned in an area where the overlapping area of the plates, permittivity of the free space and dielectric constant of the material in the gap are fixed then the changing capacitance is due to the changing distance between the plates which is related to the air flow. As with the Hall Effect embodiment this may measure both inhalation and exhalation flow using a single configuration though multiple may be used if more appropriate. This embodiment is preferably used when the dielectric constant of the material in the air gap is unchanging, such that the air gap preferably is not located in the aerosol pathway or the space between the plates is shielded from the aerosol. Capacitance can be monitored with an oscillator or charge/discharge circuit and changes in frequency indicate the flow rate.

Inductance

Figure 58:
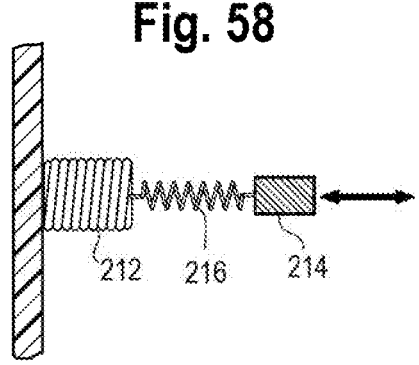
FIG. 58 is a cross-sectional view of one embodiment of a flow path.

Referring to FIG. 58, a conductive element is built into the moving component 214 of the displacement sensor. A corresponding coil 212 is placed around or near the path that the component moves in and is stationary relative to the rest of the nebulizer system. Alternatively, the coil could be moving and the conductive element is stationary. On inhalation, the moving component moves relative to the stationary one. High frequency current is passed though the loop to create an electric field. When the conductive element of the moving component is brought closer or farther away from the loop there is a measurable change in impedance in the loop. This change in impedance is directly related to the displacement of the sensor. This, in turn, is related to flow rate.

Reed Switches

Figure 59:
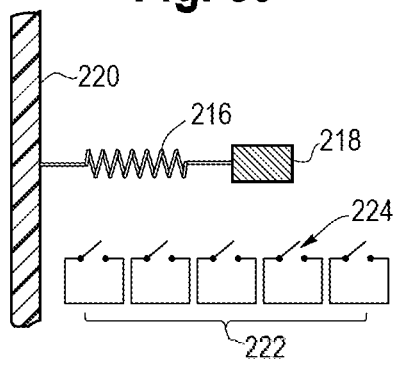
FIG. 59 is a cross-sectional view of one embodiment of a flow path.
Figure 60:
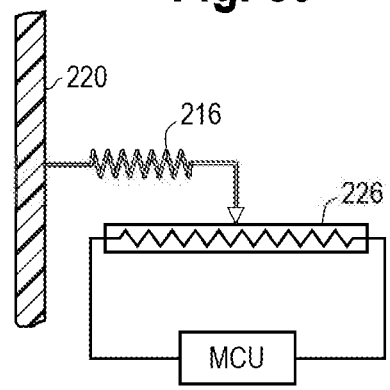
FIG. 60 is a cross-sectional view of one embodiment of a flow path.

Referring to FIGS. 59 and 60, for a reed switch embodiment, a magnetic component 218 is made to be movable relative to a stationary surface 220 and connected by a biasing element 216. As the magnetic element is displaced it changes the state of a series 222 of reed switches 224 positioned such that the activation or deactivation of switches may be related to the displacement of the movable element. This principle can be applied to any number of reed switches and can be applied to a magnetic element that either activates or deactivates the switches. This displacement may then be related to the flow rate.

Potentiometer

Referring to FIG. 60, a movable component 226 is connected to a potentiometer such that on displacement of the movable element it changes the impedance of the potentiometer. Resistance may be monitored using a simple Wheatstone bridge circuit and microcontroller. Note that monitoring of the impedance is not limited to this basic circuit.

Vibration/Acceleration

Figure 62:
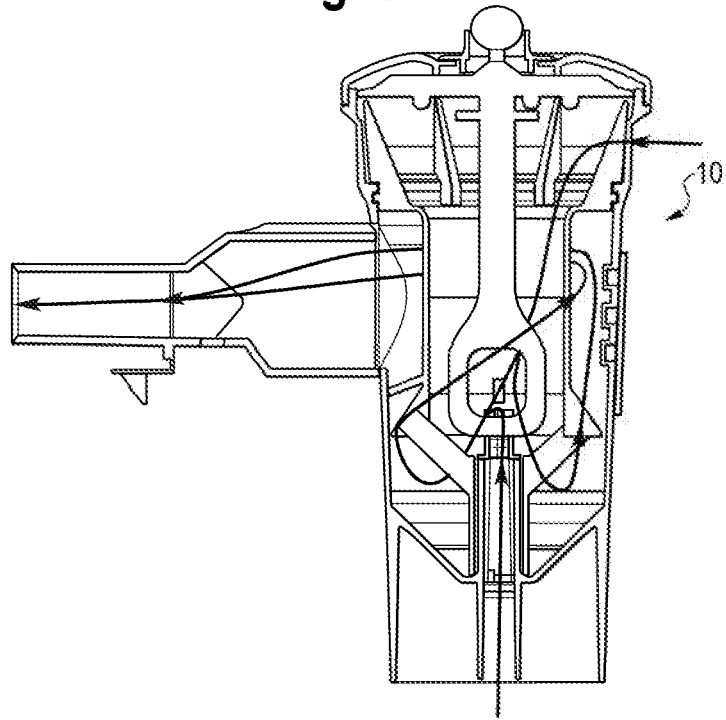
FIG. 62 is a cross-sectional view of one embodiment of a nebulizer.
Figure 63:
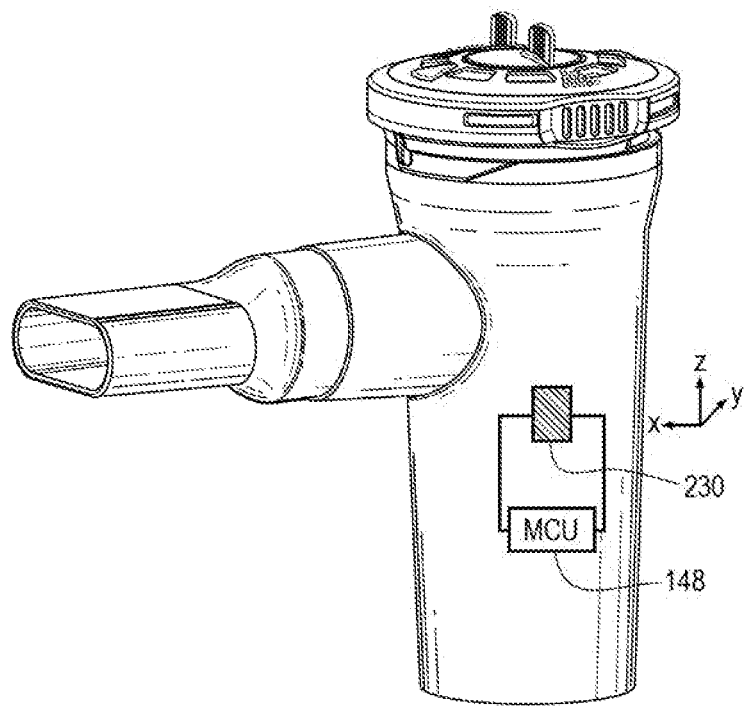
FIG. 63 is a perspective view of the nebulizer shown in FIG. 62.

Referring to FIGS. 62 and 63, similar to a sound based approach, the torturous flow within the nebulizer, designed to generate particles of a respirable size, creates turbulence as the airflow is forced around irregular, blunt geometry. The air flow and aerosol particles striking these surfaces exert a force on the nebulizer and cause the device to vibrate at very low amplitude, high frequency, levels. By placing an accelerometer 230 on the surface of the device it is possible to measure this vibration. This idea is expandable to one (1), two (2) and three (3) axes accelerometers. A microcontroller 148 would sample the data from the accelerometers and perform an analysis of it. This analysis could be programmed into the microcontroller or transmitted to an external unit with greater processing power. The signal may be analyzed by a number of methods in both the time and frequency domain to detect patterns in the acceleration that could be related to the airflow through the device. The accelerometer may record acceleration caused by the movement of the device by the patient, otherwise known as motion artifacts. Typically motion artifacts are low frequency and can be removed using a high pass filter. It is expected that the vibration caused by the airflow to be of a higher frequency and may be separated from the motion artifacts in the frequency domain.

This embodiment may be expanded to include measurement of acceleration generated by an oscillating component. Much like the generated sound method described previously, a component may be added that oscillates at a frequency that is proportional to the flow rate passing over it. Unlike the sound method, the oscillating component does not produce a sound but the oscillation is transferred to the device or to the accelerometer directly to measure the magnitude and frequency of the vibration. This, in turn, may be related to flow.

Air Supply Pressure and Nozzle Flow

Figure 64:
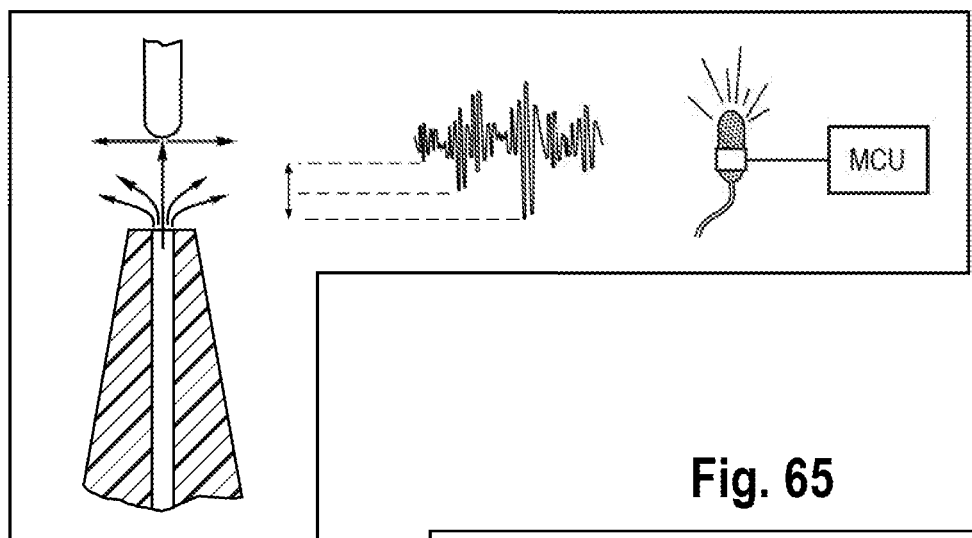
FIG. 64 is a partial cross-sectional view of a nozzle and baffle.
Figure 65:
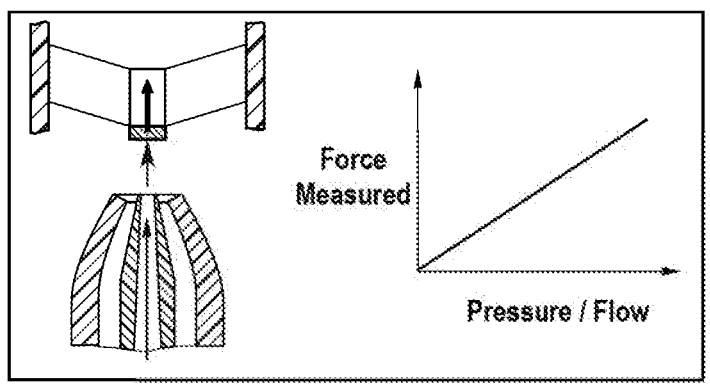
FIG. 65 is a partial cross-sectional view of a nozzle and baffle.

Referring to FIGS. 64 and 65, determining the pressure and airflow that is being supplied to the device is important in accurate calculation of drug output and delivery rate. The two parameters cannot be separated as they both contribute to the drug output rate and particle size. Wall or central air supplies used by hospital are generally capable of delivering 50 psi. However, various nebulizers may provide instructions directing the user or caregiver to dial down the pressure until the flow is between 7 and 8 L/min. Nebulizers may also be configured to work with nebulizer compressors 236, including the Trudell Medical International OMBRA Table Top and Portable compressors. With these supply components, it may not be necessary to reduce the pressure or flow, as they are configured to operate at their maximum performance. Differences in nozzle flow between devices operating on the same compressor are due to variations in the nozzle orifice size and flash. Knowing both the pressure and flow is important as particle size is dependent upon the energy supplied by the compressed air supply. In a situation where the compressors have the same nozzle flow but one has a higher pressure, the higher pressure compressor can potentially produce finer particles, all other factors held equal, as it has more energy to transfer to the liquid to increase the surface area (droplet formation).

Nozzle pressure and flow may be measured directly or inferred. Direct measurement in line with the compressed air supply and the nozzle orifice may be used or measurements may be taken elsewhere in the nebulizer system that are relatable to the air supply pressure and flow.

Embodiments and methods that measure pressure directly are preferably configured to not cause a significant permanent loss in pressure, especially in nebulizers that operate using a compressor well below the 50 [psi] maximum operating pressure.

Direct Pressure Measurement
Absolute or Relative to Atmosphere

Figure 66:
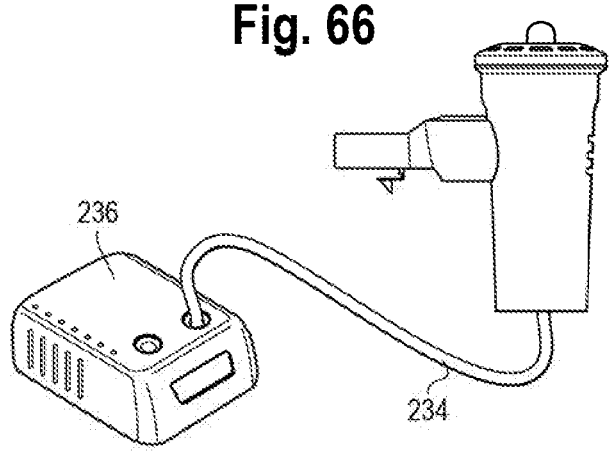
FIG. 66 is a perspective view of a compressor coupled to a nebulizer.
Figure 67:
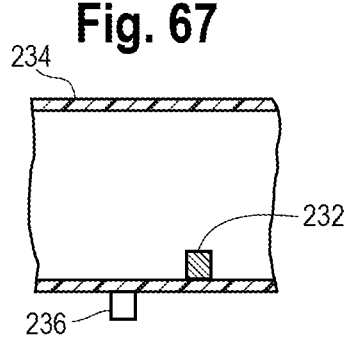
FIG. 67 is a cross-sectional view of one embodiment of a flow path.

Referring to FIGS. 66 and 67, as described in Pressure Based Approach—Flow Measurement a pressure sensor 232 may be placed in-line with the air supply, e.g., tube 234, to the nebulizer and measure the absolute pressure within the device or the with the addition of a second sensor 236 to atmosphere, then the pressure relative to atmosphere. The pressure sensor is not limited to placement within the nozzle and may also be placed within the tubing 234 itself.

Strain Gauge

Figure 68:
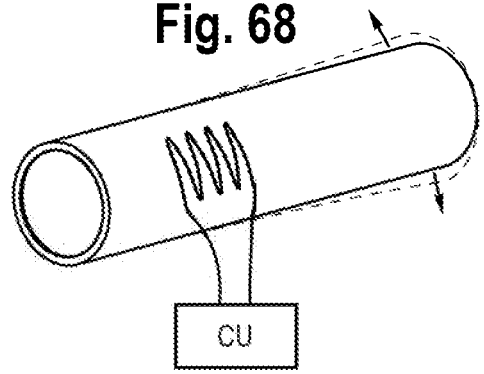
FIG. 68 is view of a portion of a supply tubing.

Referring to FIG. 68, a strain gauge 128 placed on a flexible hosing 234 used to transport the compressed air supply could be used to determine the pressure supplied to the nebulizer. In one embodiment the strain gauge is placed on the tubing used to connect the nebulizer to the wall air or compressor. When the tubing is pressurized it is placed in tension and expands. This expansion can be measured with a strain gauge and communicated to a control unit through physical or wireless communication.

Direct Flow Measurement
Pressure

All flow measurement techniques covered in the Measuring Flow—Pressure Based Approach section are applicable as an in-line flow measurement technique however all of them result in various degrees of permanent pressure loss which should be avoided. This method is also able to provide absolute pressure by monitoring the downstream pressure sensor reading or the pressure relative to atmosphere through the addition of a third sensor exposed to the external environment.

Sound

The Measuring Flow—Time of Flight/Transit Time applies to measuring the air flow applied to the nebulizer. The sensors may be placed anywhere between the tubing attachment and exit orifice of the nebulizer.

Temperature

The Measuring Flow—Temperature Based Methods applies to measuring the air flow applied to the nebulizer. The sensors may be placed anywhere between the tubing attachment and exit orifice of the nebulizer.

Turbine

The Measuring Flow—Turbine Flowmeter applies to measuring the air flow exiting the pressurized gas orifice of the nebulizer. The sensor may be placed anywhere between the tubing attachment and exit orifice of the nebulizer however this method may result in a permanent pressure loss.

Inferential Pressure/Flow Measurement

Inferential pressure and flow calculations are not able to provide direct measurements of pressure or flow but they may be inferred if the calculation error introduced through the range of pressure and flow combinations is not statistically significant. Inferential measurements of pressure and flow are not able to distinguish between pressure and flow as these parameters cannot be separated from one another without direct measurement of each. As such, only pressure will be referred to in the following methods as it is the driver of the flow. Fluctuations in flow at constant pressure are the result of variations in the pressured gas orifice dimensions and the level of flash present.

Intrinsic Sound

When supplied with pressurized air and being run dry, the nebulizer produces a sound that is characteristic of the pressurized gas exiting the orifice. As with flow measurement using sound, the sound is dependent on the flow exiting the orifice and the subsequent turbulence caused by the air following the tortuous pathway in the device. An increase in pressure produces an audible increase in sound intensity and may affect the frequency content of the sound. A single or multiple microphones may be used to monitor the sound and of the nebulizer before treatment is administered to establish the pressure/flow from the air supply. Multiple analysis techniques exist that can analyze the sound using a local control unit or a remote control unit to which data is wirelessly communicated and compared to a known library of sound profiles with known performance characteristics.

Vibration/Acceleration

As with Vibration/Acceleration—Flow Measurements, an accelerometer may be used to measure vibration of the nebulizer prior to aerosolization. These vibrations may provide an indication of the pressure/flow being supplied to the nebulizer with each pressure/flow having a characteristic acceleration signature. The Vibration/Acceleration—Flow Measurements section above provides more details on the implementation of such an embodiment and method.

Flow Through Device

All embodiments and methods described in the Measuring Flow/Breathing Pattern section may be used to measure the pressure/flow being supplied to the nebulizer. Flow measurements taken while the device is being run dry without the patient interfacing with the device are indicative of the pressure/flow supplied to the nebulizer. Local measurements of pressure and flow may be related to the flow through the pressurized gas orifice through experimental testing. These flow measurements may then be compared to a database of supplied pressures/flows and their corresponding local flow measurement.

Force of Air Striking Baffle

In one embodiment, the baffle is constructed from a load cell. When pressurized air is supplied to the nebulizer it exits the pressurized gas orifice and strikes the baffle, exerting a force on it proportional to the flow rate. A control unit can monitor this force calculate the pressure/flow supplied to the device through a relationship determined experimentally. Additionally, this system may be used to wake a control unit from a low energy state as pressurized gas must be supplied to the nebulizer for treatment to occur. This would reduce energy requirements of the system and, if the unit is battery powered, help to prolong the battery life. A pressure sensitive sensor may also be used in place of a load cell.

Compatible Smart Compressor

An alternative approach to having the smart nebulizer system monitoring the air supply pressure and flow is to market a series of compressors that are compatible with the smart nebulizer. These compressors monitor the supply pressure and flow through a variety of means and communicate this data to the nebulizer. This data may be transmitted wirelessly directly to the nebulizer or to the overall control unit, such as a smartphone. The data could also be transmitted through a physical connection such as a data cable ran through the oxygen tubing or by placing the nebulizer is a port on the compressor for data syncing. Please note that the data transmission is not limited to these methods.

Medication Identification

A smart nebulizer system should be able to recognize the medication being administered to the patient. This information is important to the patient, healthcare provider and insurer as it ensures the treatment regime is being adhered to. In addition, knowing the medication being nebulized is also important in calculating the respirable fraction. Though many of the medications commonly nebulized are a solution and yield comparable particle sizes, some medications have different physical properties such as viscosity that affect the particle size the nebulizer is capable of generating. Medication identification can be accomplished in a variety of ways ranging from identification based on the packaging to a chemical analysis of the medication. Each of the individual methods listed below may be used to identify the medication, or a combination of the methods may be used to increase the robustness of the medication identification feature.

Image Processing

Existing Packaging Barcode

Referring to FIG. 76, some medication packaging 240 (boxes and nebules) have existing barcodes 238 that may be read by a bar code scanner. The bar code scanner may be incorporated into the smart nebulizer 10 itself, into to a phone based application that is in communication with the smart nebulizer, or a standalone reader that can communicate with the smart nebulizer system, for example by bluetooth, Supplied Barcode Similar to Existing Packaging Barcode except a specialized barcode may be placed on the medication by the user, distributor or manufacturer rather than relying on existing ones. This embodiment and method ensures any medication that is provided with this barcode has been pre-approved for use.

Text Recognition

Text recognition software can recognize the text written on the medication packaging and identify the applicable information.

Feature Recognition

An image of the packaging is compared to image kernels in a database of compatible medication. The correlation coefficient between the captured image and all image kernels may be calculated and medication identified based on the greatest correlation coefficient. Other matching algorithms are available and may be used.

QR Code

This method is similar to Supplied Barcode except that a QR code is used in place of the barcode.

RFID or NFC Device

Referring to FIGS. 77 and 78, Radio Frequency Identification (RFID) tags 242 or other Near Field Communication (NFC) components may be applied or built into the medication packaging 240. The identification component 242 may be recognized by a reader 244 on the smart nebulizer 10 itself or a standalone device that is in communication with the smart nebulizer. Alternatively, many smartphones have NFC capability built into them. These phones may be used to recognize the medication and communicate with the nebulizer.

Access Patient Electronic Medical Records (EMR)

Referring to FIG. 78, a patient's Electronic Medical Records (EMRs) may be accessed by the smart nebulizer system through direct Wi-Fi access or wireless communication with an Internet accessible device. If the patient has been prescribed multiple medications for nebulization it can supply a subset of medications that another identification method may select from.

Manually Selected by the User

Rather than automatically detecting the medication being used by the patient, the user may manually input the medication they are using. This may be done on the device itself or on a standalone device that is in communication with the smart nebulizer. There are many methods the patient may use to input their medication such as a drop down list or searchable database. Alternatively, a chat bot may be used. This uses an automated assistant that asks the patient a series of questions using a chat window type interface and the patient is able to respond using natural language, eliminating the need to navigate a user interface.

Capacitance

Two oppositely charged features are separated by an air gap. On activation, aerosol flows through the gap. Assuming the aerosols have different dielectric constants from each other, the capacitance change caused by the aerosol in the air gap can be measured and compared to a database of capacitance values of compatible aerosols. Alternatively, as shown in FIG. 71, the two oppositely charged features 246, 248 may be placed on either side of the medicine howl, or reservoir, such that when medication is inserted into the nebulizer the medication fills the space between them. Assuming the dielectric constants of the medications are measurably different, the medication may be identified. The capacitive probe may also be placed directly within the liquid medication.

Single Drug Nebulizer Rather than identifying the drug used in the nebulizer, the nebulizers can be programed with the information pertaining to a single drug and be marketed for use solely with that drug. To reduce the risk of the nebulizer being used with multiple drugs it could be a single use device that may come pre-filled with medication and has no port through which additional medication may be easily inserted. The electronic portion of the nebulizer would be removable and each use, the disposable portion of the nebulizer would be discarded. Information pertaining to the drug in the nebulizer could be programmed into a low cost component such as, but not limited to, an EEPROM chip and accessible by the reusable portion of the nebulizer when docked.

Spectroscopic Drug ID/Colour

Figure 79:
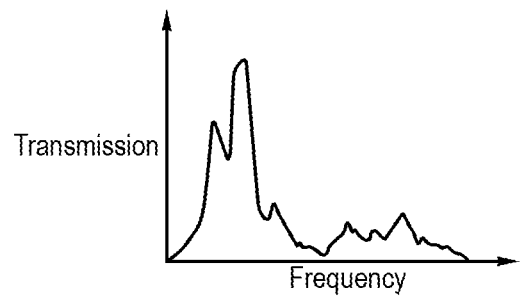
FIG. 79 is a graph of for spectroscopic drug identification.
Figure 80A:
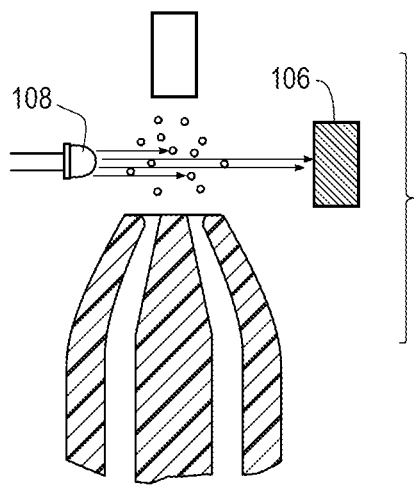
FIGS. 80A and B show embodiments of different flow paths.
Figure 80B:
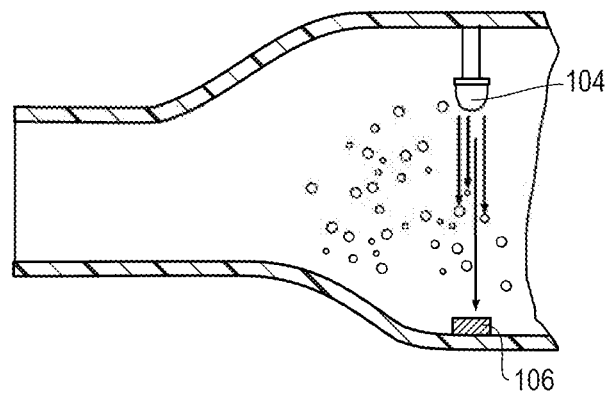
Figure 81:
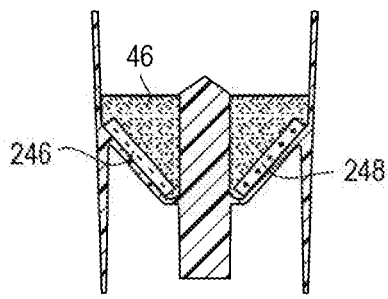
FIG. 81 shows a cross-sectional view of one embodiment of a reservoir.

Referring to FIGS. 79-80B, single or multiple wavelength spectroscopy could be used to analyze the aerosol or liquid medication to determine the chemical structure of it. All chemicals absorb unique wavelengths of light and the degree to which they absorb the light is dependent on the bonds present in their chemical structure. A light source 108 of a single or multiple wavelengths may be shone through the aerosol or liquid medication and the absorbency analyzed by a detector placed opposite the light source. The absorbency information may then be compared to a database of compatible medication. The light source and detector may be placed anywhere along the aerosol pathway, such as within the mouthpiece (FIG. 80B) or within the medication bowl (FIG. 80A) for analysis of the liquid. This is, in effect, an analysis of the colour of the medication, however colour is the measure of what is reflected by the substance rather than absorbency.

pH

Figure 82:
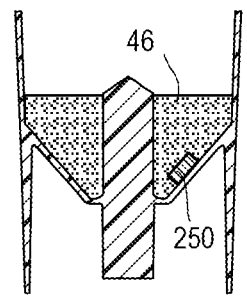
FIG. 82 shows a cross-sectional view of one embodiment of a reservoir.

Referring to FIG. 82, the pH of each medication may be used to help identify the medication or be used to select a subset of medications from which another identification method may select from. Nebulized medications are often pH adjusted in order to balance them to be close to neutral however differences still do exist between medications. An example of this would be differentiating between Acetylcysteine and Albuterol. Assuming a medication has been narrowed down to these two medications through another method, pH could be used to differentiate them as Acetylcysteine solutions have pH ranging from 6.0 to 7.5 while Albuterol solutions are typically between 3.0 and 5.0.

In one embodiment a pH sensor 250 is placed in the medication bowl 46 where it is in contact with the liquid. The sensor is able to measure the pH of the liquid due to the differences in hydrogen ion concentration. The sensor communicates this to a microcontroller which may select the medication or a subset of medication from a database of pH readings and medications, determined experimentally.

Concentration Identification

It would be advantageous if a smart nebulizer could measure the concentration of medication in the medication bowl at any point in time. Identification of the medication does not provide concentration, knowing the concentration is required in order to calculate drug output. Even if medication concentration is obtained when the medication is identified, it is normal for the concentration of medication in the bowl to increase over the course of a treatment and drug output rate to increase as a result. The following methods may or may not be used in conjunction with the medication identification methods described previously.

Capacitance

Referring to FIG. 97, assuming the medication has already been identified, the particular capacitance of the medication at a point in time may be relatable to the concentration. If the capacitance has already been identified, the initial concentration may be measurable from the initial capacitance. It is assumed that the dielectric properties of the medication are different than the aqueous mixture they are diluted with. As a nebulizer treatment progresses and the drug becomes more concentrated in the nebulizer bowl, there may be a change in the overall dielectric constant due to the greater concentration of the medication. This may be measured by insulated parallel features that are oppositely charged. A charge discharge circuit may be used to test the capacitance and be monitored by a microcontroller. In one embodiment, a capacitance probe is integrated into the lowermost section of the nozzle and nozzle cover with the outer surface of the nozzle and inner surface of the nozzle cover acting as the oppositely charged features. The gap between them is positioned such that it is always below the level of the fluid and the distance between them is unchanging. A separate capacitive probe could also be integrated into the bottom surface of the medication howl. The probes are preferably immersed in the medication as the presence of air between the oppositely charged features may affect the capacitance.

Spectroscopy/Colour

Referring to FIG. 99, as with medication identification using spectroscopy/colour, single or multiple wavelength spectroscopy could be used to analyze the liquid to determine the chemical structure of it as well as the relative concentration of each component. All chemicals absorb light to one degree or another and the degree to which they absorb them is dependent on the bonds present in their chemical structure. A light source of a single or multiple wavelengths may be shone through the liquid medication and the absorbency analyzed by a detector placed opposite the light source. The absorbency information may then be compared to a database of compatible medication. The light source and detector may be placed within the medication bowl such that liquid is able to pass between them when present. The concentration of each compound should be reflected in the relative absorbency measurements with more concentrated compounds able to absorb more light. This is, in effect, an analysis of the colour of the medication, however colour is the measure of what is reflected by the medication rather than what is absorbed.

Light Transmission

Referring to FIG. 86, similar to the spectroscopy/colour technique except the relative intensity of light that transmits through the liquid is analyzed rather than a detailed analysis of the detected wavelengths and level of absorption. In one embodiment, a light transmission device/method may look solely at infrared transmission as it would not be visible by the patient. A sensor 262 may be positioned below a transparent/translucent bowl, with a light source 264 positioned in the bowl, with the light passing through the liquid.

Conductivity

Referring to FIG. 100, conductivity may also be used to measure the concentration of the medication. Many nebulized medications use acids and bases to balance the pH which introduces charged particles to the liquid. The number of these charged particles is directly related to the conductivity of the liquid, as a current can more easily conduct in the presence of a greater number of charged particles. This is related to the measurement of pH however it accounts for all ions in the medication while pH is a measure of hydrogen ions only. Conductive sensors tend to measure conductivity through a capacitive change or an inductive change. Preferably, the active region of the sensor is placed within the medication bowl so that it is continually immersed in the liquid medication.

pH

Figure 85:
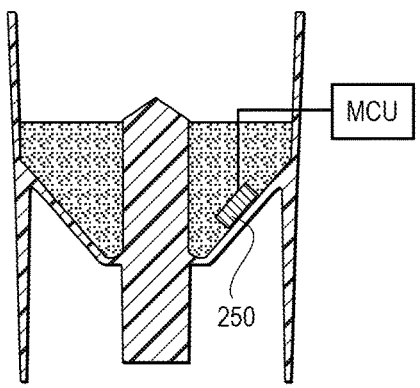
FIG. 85 is a cross-sectional view of one embodiment of a reservoir.
Figure 86:
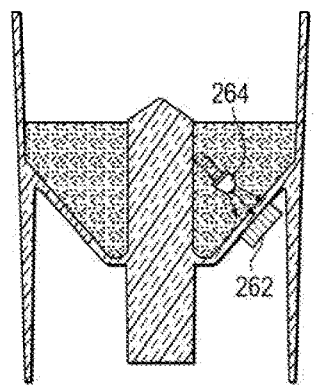
FIG. 86 is a cross-sectional view of one embodiment of a reservoir.
Figure 87A:
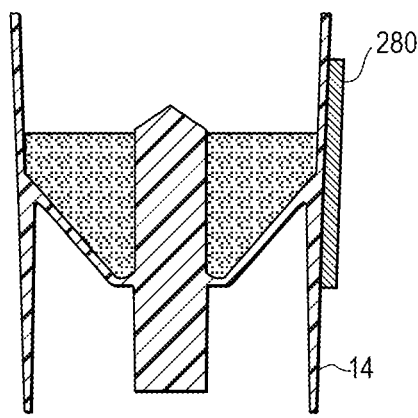
FIGS. 87A-C are cross-sectional views of various reservoir embodiments.
Figure 87B:
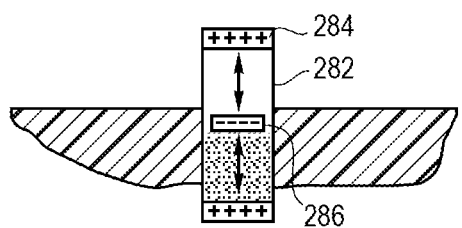
Figure 87C:
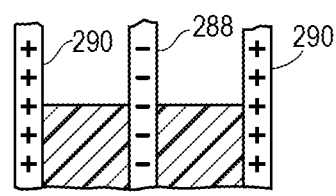
Figure 88:
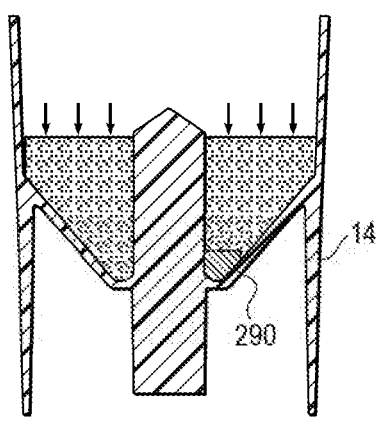
FIG. 88 is a cross-sectional view of one embodiment of a reservoir.
Figure 89:
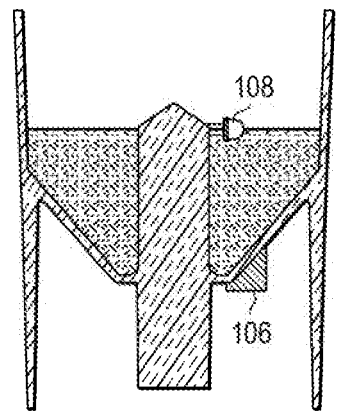
FIG. 89 is a cross-sectional view of one embodiment of a reservoir.
Figure 90:
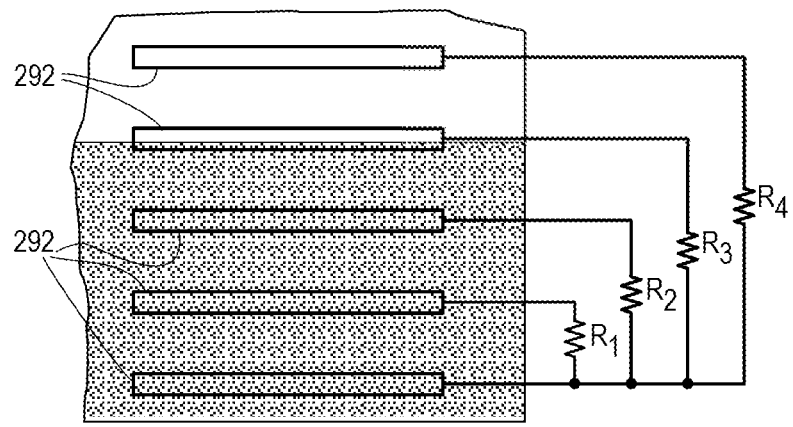
FIG. 90 is a cross-sectional view of one embodiment of a reservoir with conductive strips.
Figure 91:
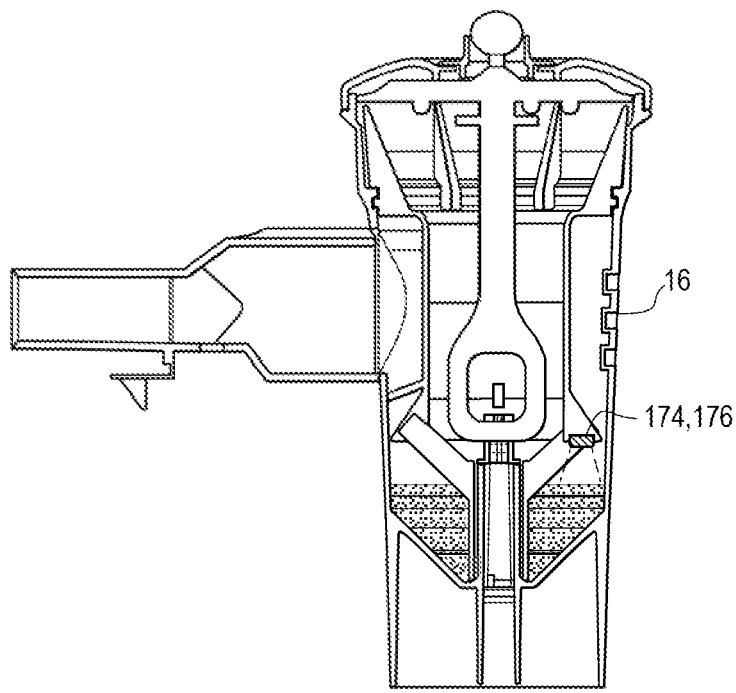
FIG. 91 is a cross-sectional view of one embodiment of a nebulizer.
Figure 92:
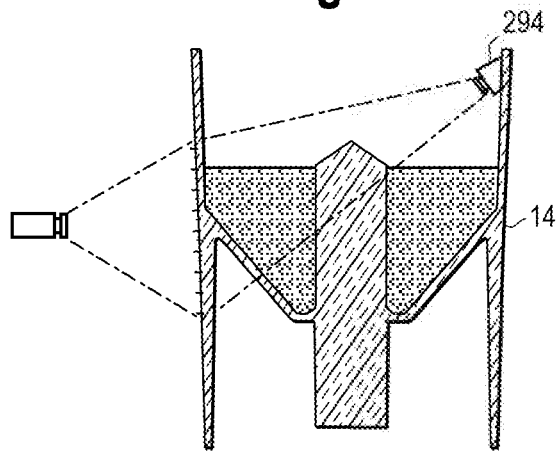
FIG. 92 is a cross-sectional view of one embodiment of a reservoir.
Figure 93:
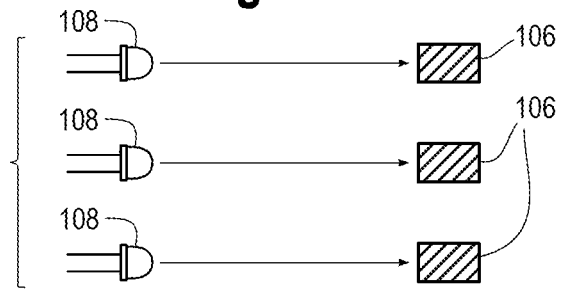
FIG. 93 is a schematic view of one embodiment of a fluid level in a reservoir.
Figure 94:
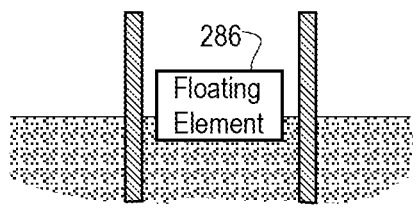
FIG. 94 is a cross-sectional view of one embodiment of a reservoir.

Referring to FIG. 85, if the concentration change of medication results in a change in the number of hydrogen ions in the medication than pH may be related to the concentration. A pH probe 250 may be placed in the medication bowl in contact with the liquid and monitored by a microcontroller 148. Note that this measurement cannot be used to determine the initial concentration and can only measure a change in concentration as most nebulizer medications are balanced through the addition of acids and bases until the phis close to neutral.

Time of Flight

Referring to FIG. 98, if the medication is known, the concentration may be identified based on the time of flight between a transducer 300 and receiver 302. A probe 304 is placed in the medication bowl that contains a transducer and receiver that are directed at one another and separated by an air gap. The probe is placed such that it is always immersed when medication is in the bowl. Air gaps between the transducer and receiver would affect the accuracy of the measurements. Sound ways of the ultrasonic frequency are often used by all frequencies are applicable to this claim. The probe measures the time it takes for the sound to travel from the transducer to the receiver. The concentration of the medication between the transducer and receiver may affect the speed of propagation of the sound wave. A microcontroller would monitor the time of flight and relate this to a concentration from a database of values determined experimentally.

Manual Entry

The initial medication concentration can be manually input into the nebulizer if it is known by the patient. This may be done on the device itself or on a standalone device that is capable of communicating with the nebulizer. This embodiment and method may be particularly useful for medications where the concentration change or the duration of the treatment is not substantial.

Particle Size Measurement

Particle size distribution is an important factor in calculating the dose delivered to the patient. This is because there is a respirable range of particles between 0.4 [μm] to 4.7 [μm]. Particles below this diameter are too small to deposit in the airways and are lost through exhalation while particles above this range impact in the upper airways as they have too much inertia to follow the convoluted pathway into the lower airways. Drug that impacts in the upper airways is not usable by the patient. Dose delivered to the patient is the product of the drug output and the fraction of the particles within the respirable range, also known as the respirable fraction. It is possible to characterize the particle size of the nebulizer based on the inlet pressure and flow as well as the inhalation flow rate and compile these relationships in an electronic database that is searchable by the smart nebulizer system. However, it would be advantageous to be able to directly measure the particle size distribution of the aerosol directly within the nebulizer and not introduce another level of uncertainty into the dose delivery calculation.

Light Diffraction Measurement

Figure 69:
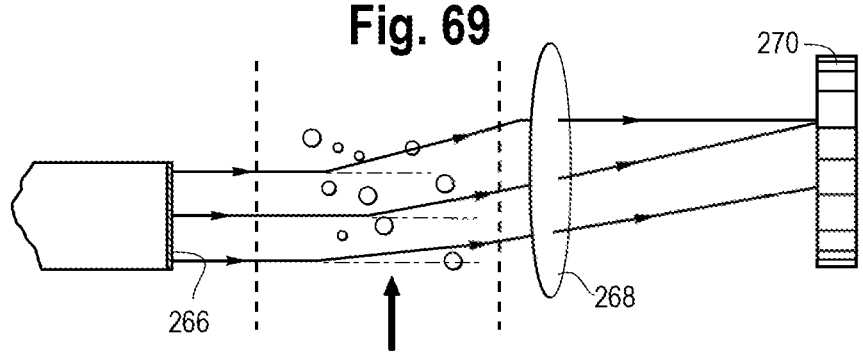
FIG. 69 is a cross-sectional view of one embodiment of a flow path.
Figure 70:
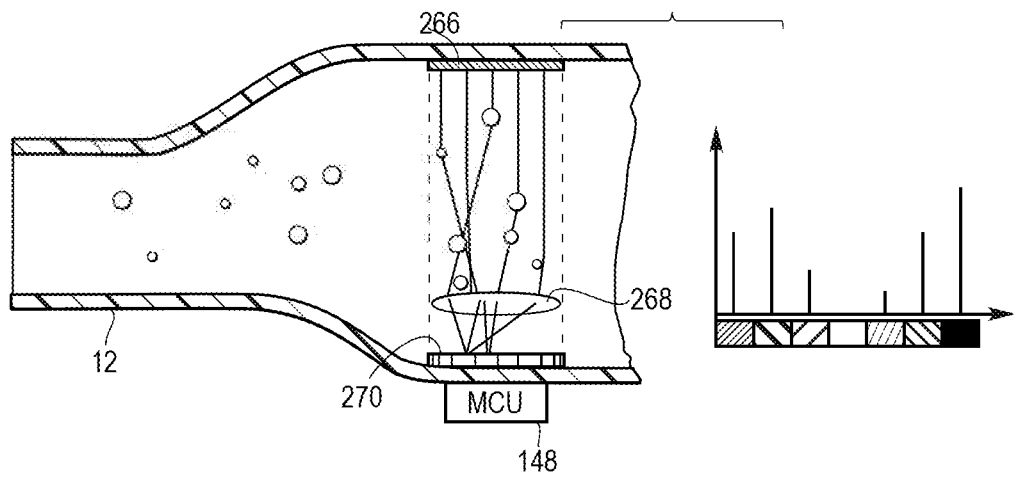
FIG. 70 is a cross-sectional view of one embodiment of a flow path.

Referring to FIGS. 69 and 70, light diffraction measurement of particle size distribution assumes particles are approximately spherical in shape. Monochromatic light, from a light source 266, which is approximately collimated (parallel) is shone through the aerosol as it flows along the inhalation pathway. As the light shines across the aerosol pathway it may or may not pass through aerosol droplets that diffract the light. The angle of diffraction is dependent upon the particle size with particles of equal size diffracting the light equally. Opposite the light source 266, on the other side of the aerosol pathway is a Fourier lens 268 that separates the received light beams by the angle of diffraction and focuses this light on a detector 270 behind it. Light passing through that is diffracted at the same angle will be focused on portions of the detector that are equidistance from the center of the detector. This creates a spatial separation of light based on the angle at which it was diffracted by the aerosol. The pattern of light intensity received by the detector is passed through to a control unit for processing and compared to a database of light intensity patterns with known particle size.

It is important that the set-up be positioned after all baffling as this baffling is responsible for producing the required particle sizes. The torturous path that the airway must follow causes most particles above the respirable range to impact on the internal walls of the device and rain out, back into the medicine bowl where it may be re-nebulized.

One embodiment integrates this particle measurement method into the mouthpiece 12. On one side of the cylindrically shaped mouthpiece is a light source 266 while the other contains the Fourier lens 268 and detector 270. A control unit 148 may also be contained in the mouthpiece to process the signals from the detector. Alternatively, the data may be wirelessly transmitted to an external device for processing, such as a phone. The system may be tied in with one of the activation detection embodiments so that the light source and detectors only turn on when aerosol is present. As aerosol passes through this area it creates a unique diffraction pattern that is spatially encoded by the Fourier lens onto the detector. The nebulizer can then take this data and determine the percentage of aerosol that is in the respirable range. This embodiment could also be used to detect activation. Prior to aerosol production, no aerosol would be passing between the light source and lens and therefore, no light would be scattered and the Fourier lens would focus all light on the DC, or low frequency, section of the detector. On activation, the light would be scattered and focused to other portions of the detector, indicating that aerosol was present as well as its particle size distribution.

Inertial Separation

Figure 71A:
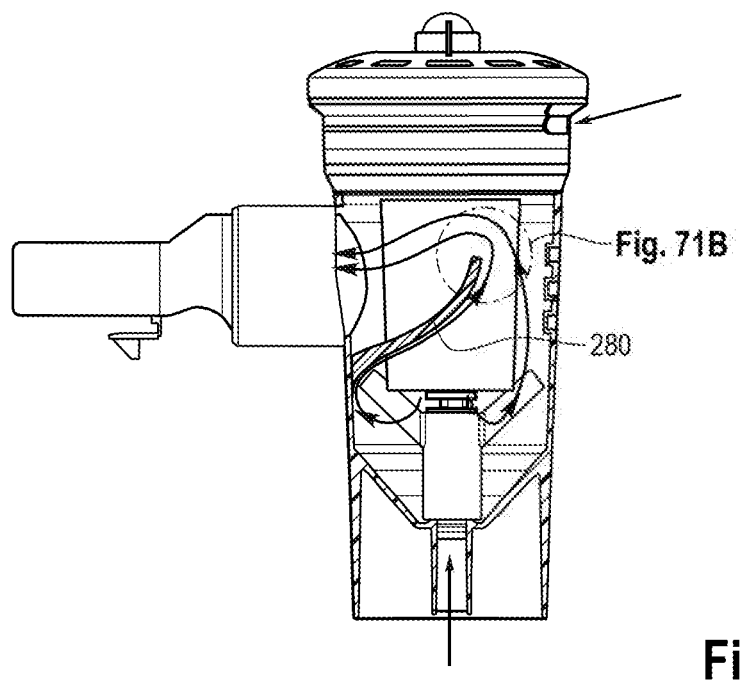
FIGS. 71A-C are a cross-sectional view of one embodiment of a nebulizer and an enlarged portion thereof, with attendant particle separation.
Figure 71C:
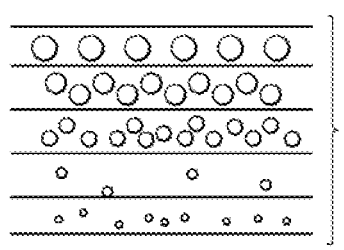
Figure 71B:
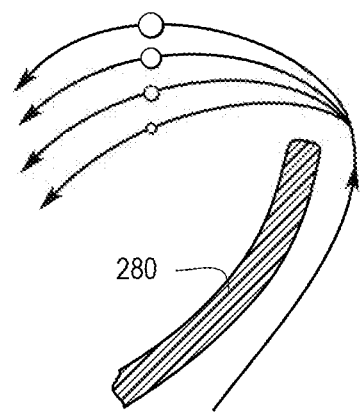

Referring to FIGS. 71A-C, another option for measuring particle size is to mechanically separate the particles based on their size and analyze the flow of these ordered particles past a sensor. Particles of different sizes have different masses. As the airflow forces the aerosol around the baffling within the nebulizer every particle resists the change in direction due to their inertial forces. Particles with larger mass will resist the change in direction more than smaller ones due to their greater inertial force. As a result, smaller particles are able to turn these corners more quickly than larger ones and particles may be separated based on their trajectory. This method of inertial separation may be done in a variety of ways using a multitude of geometries and flow paths such as through microfluidic channel and vortex separation, all of which are applicable to this embodiment.

In one embodiment, the existing geometry of the nebulizer is used. As aerosol is produced, air enters through the compressed gas orifice and the inhalation ports, collects aerosol formed by at the primary baffling and moves around the secondary baffling, henceforth known as the fin 280. As the airflow moves around the top edge of the fin 280 and towards the mouthpiece 12 it forces the airflow to make an approximately 180° directional change (FIG. 71B). The smaller particles are able to follow the contour of the fin while the inertia of the larger ones causes them to take wider trajectories. This creates a spatial separation of the particles sizes into 'bands" with the larger particles tending to be closer to the top half of the device and the smaller ones are lower, closer to the contour of the fin.

Figure 72:
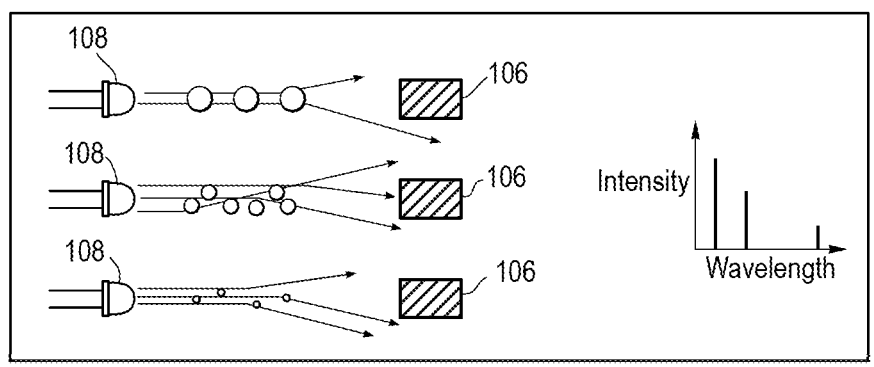
FIG. 72 is a schematic showing light based analysis of particle size.

A light sensor 108 and detector 106, or an array/series thereof, may be placed opposite of each other with this segregated airflow moving between them as shown in FIG. 72. The range of light intensities detected by the opposing sensor, taking into consideration the differences in diffraction of particle sizes, could be related to the particle size distribution. Multiple wavelengths of light sources and detectors may be used for each "band" of particle size. By doing so, diffraction from one band of particles to another detector will not show as an increase in light intensity as the detector will not register light of a different wavelength. Image processing may also be used to look at the relative "density" of the aerosol in each section of the gradient and estimate particle distribution based on this. Alternatively, the particles may be physically separated by guiding a subset of the flow through microfluidic channels and analyze each of the channels separately for characteristics dependent on the amount of aerosol in each channel such as, but not limited to, capacitance, inductance, conductivity, light transmission, light reflectance, pH, temperature and humidity.

Force Sensing Baffle

As described in Air Pressure and Nozzle Flow—Force of Air Striking Baffle, a force or pressure sensing element is incorporated into the baffle. Knowing the force of the aerosol striking the baffle would allow for an estimation of the particle size. This embodiment and method may account for factors such as nozzle misalignment and baffle variation and is a local measurement of the actual energy being applied to the mixed liquid flow to form aerosol.

End of Treatment

Figure 73:
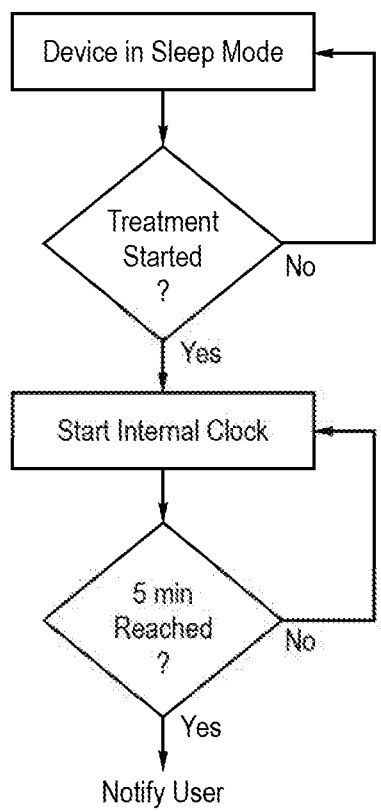
FIG. 73 is a flow chart showing use cycle with end of treatment notification.

End of treatment can be defined in a number of ways. If the dosage is known based on the respirable amount that must be delivered to the patient, end of treatment can be calculated using a combination of methods covered previously. However, many treatment regimens do not provide the respirable dosage for the patient and provide a treatment protocol based on time or sputter. In the United States, a Hospital Protocol Summary has been developed for the current AEROECLIPSE nebulizers. This protocol defines end of treatment based on a volume of drug nebulized until initial sputter is heard or a volume of drug nebulized for five (5) minutes. A smart nebulizer may be capable of determining when sputter has occurred or an internal clock capable of detecting initial activation and counting down treatment time and subsequently notifying the patient when the end of the timed treatment has been reached (see FIG. 73).

Sputter

Microphone

Figure 75A:
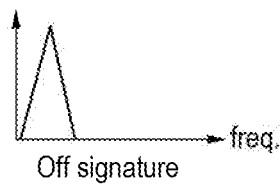
FIGS. 75A and B show switch signatures for “sputter.”
Figure 75B:
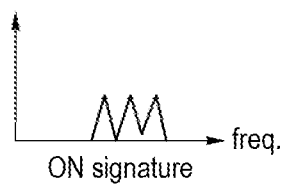
Figure 74:
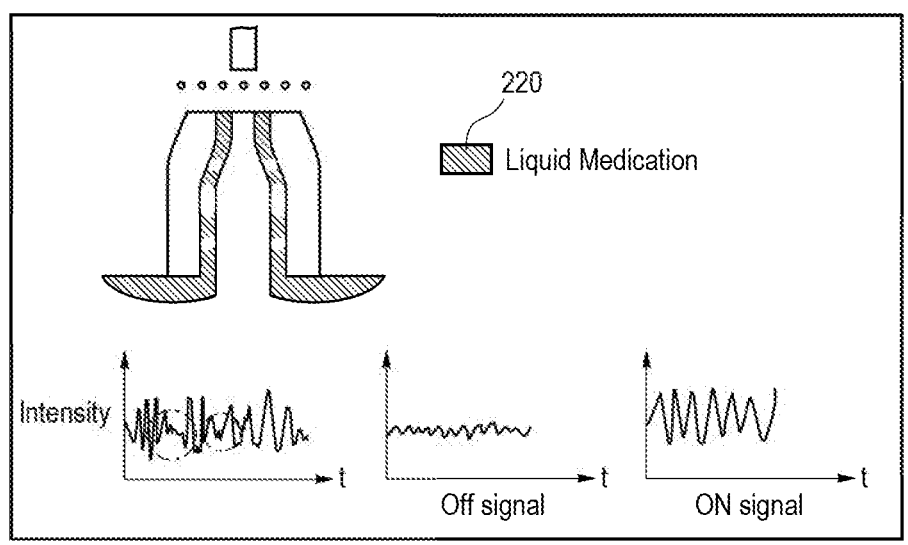
FIG. 74 is a partial cross-sectional view of a nozzle and baffle.
Figure 76:
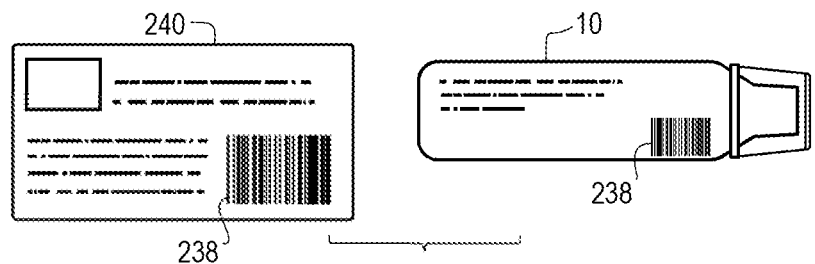
FIG. 76 shows one embodiment of a packaging or nebulizer with bar code.
Figure 77:
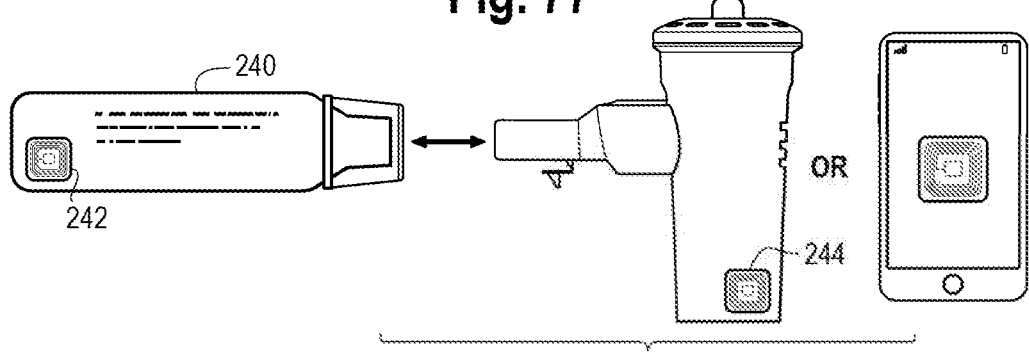
FIG. 77 shows one embodiment of a nebulizer with an RAID tag and reader.
Figure 78:
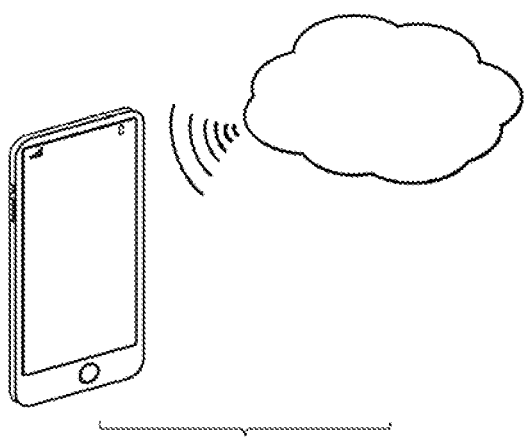
FIG. 78 is a schematic of a communication protocol.

Referring to FIGS. 74-75B, in one embodiment, a microphone 120 is placed within the nebulizer to listen for sputter. Alternatively, a microphone is placed externally or is contained in a separate, stand-alone device. Sputter is caused by gaps in fluid flow through the annular liquid channels due to insufficient medication in the medication bowl. This causes a rapid switching between the ON and OFF states. The ON state is when liquid is being drawn through the liquid channel and is impacting on the primary baffle while the OFF state is when no liquid is being aerosolized and only air is striking the baffle. A control unit could compare the current state of the audio signal to known OFF and ON signals in a database and recognize rapid switching between them. The rate at which the device switches between these states is important as it can differentiate between the activation and deactivation caused by the breathing cycle and gaps in the liquid flow. This analysis is not limited to the time domain and can be processed with alternative methods, all of which are applicable to this embodiment. When the nebulizer recognizes that sputter has occurred it notifies the patient.

Force Sensing Baffle

As in Air Pressure and Nozzle Flow—Force of Air Striking Baffle, a force or pressure-sensing element is incorporated into the baffle. When the actuator is in the OFF position, a reduced flow of air strikes the baffle as much of the flow escapes through vacuum break windows in the nozzle cover. When the actuator is down, all air flow is directed at the baffle as the windows in the nozzle cover are blocked and air is entrained due to the negative pressure over the liquid channel drawing additional flow through the nozzle cover. This force increases further when liquid is pulled up the liquid channel and strikes the baffle. Sputter may be identified as the gaps in the liquid flow reducing the force on the baffle and returning it to levels immediately prior to aerosol formation, but not the levels when the actuator is in the OFF position. This would allow for differentiation between sputter and activation/deactivation of the nebulizer. Alternatively, the rapid switching between the ON and OFF states on sputter may differentiate from the relatively slow frequency of purposeful activation/deactivation. When the nebulizer recognizes that sputter has occurs it notifies the patient.

Timed Treatment

In one embodiment, the control unit of the device has internal clock functions that can determine when a predetermined amount of time has elapsed. When used in conjunction with any method described in the Activation Detection section, activation of the device starts an internal clock that records treatment duration. In the United States, this time is commonly five (5) minutes. At the end of the predetermined amount of time the nebulizer notifies the patient that end of treatment has been reached.

Fill and Residual Volume Determination

It would be beneficial if a smart nebulizer was able to measure the initial fill volume and/or residual volume of the medication. Though the initial fill volume may be made available through the medication identification feature and residual volume estimated based on the drug output calculations, it would be advantageous to be able to measure these parameters directly to remove a degree of uncertainty from the system. Residual volumes in particular are important as they represent the amount of drug that the nebulizer is not able to nebulize and is therefore wasted. Tracking this is important as it can potentially indicate the performance of the nebulizer. A high residual volume after sputter could indicate a device has exceeded its useful life and should be replaced. This ensures the patient is always receiving a consistent level of treatment. A high residual volume could also indicate that the device has been insufficiently cleaned and prompt the user to do so, as well as providing proper instructions for them to follow. Tracking residual volume is may also provide feedback to researchers and product developers.

Fluid Level

Initial fill volume and residual volume may be estimated based on the fluid level in the medication bowl. Knowing the fluid level and the geometry of the medication bowl allows for the calculation of the volume of medication. The disadvantage of such a method is that it cannot account for medication that is coating the internal surfaces of the nebulizer and have not drained back into the medication bowl. Also, calculating fluid level requires the fluid surface to be relatively still. This means that fluid level cannot be measured while the device is aerosolizing due to the turbulence that is created from the pressurized air as it is redirected radially by the primary baffle.

Thin Film Capacitance Sensor

Referring to FIG. 87A, a thin film, flexible capacitive sensor 280 could be placed on the outside side of the medication bowl to measure the fluid volume. As with other capacitive methods described in this document, the dielectric constant of liquid is different than that of air. The presence of liquid near the capacitive sensor causes a change in capacitance that may be measured and related to fluid level through experimentation. The greater the volume of liquid in the medication bowl, the greater the area of the capacitive strip that is in close proximity to the liquid and the greater the capacitance change. The advantage of this method is that the thin film, capacitive sensor may be placed on the outside of the device and not in direct contact with the fluid.

Referring to FIG. 87C, another type of capacitive fluid level sensor involves a cylindrical shaped probe 288 with a cylindrical core inside, separated from the outer casing 290 by an annular air gap. These two elements are oppositely charged to form a capacitor. When the probe is placed into the medication, fluid is allowed to enter the bottom of the probe and fill a portion of the air gap between the oppositely charged probe and outer casing. Since the dielectric constant of the fluid medication will be different than that of air there will be a measurable capacitance change. The degree of capacitance change is related to the level of the fluid in the probe.

Float

Referring to FIGS. 94 and 87B, a float based sensor can also be used to measure the volume of medication in the nebulizer. In a float sensor there is always a floating element 286 that rests on the top surface of the fluid. Changes in the fluid level also change the position of the floating element. The position of the float in relation to a stationary sensing unit 284 may be monitored using a multitude of methods and is related to the volume in the nebulizer based on the known geometry of the nebulizer bowl. The position of the floating element may be tracked by, but not limited to, resistance change of a potentiometer, capacitive proximity sensing, inductive proximity sensing, hall effect, change in state of a series of reed switches and more. This embodiment is applicable for all methods of measuring volume in the nebulizer using a float based probe.

Pressure

Referring to FIG. 88, a pressure sensor 290 may be used to measure the volume of fluid in the bowl. This method is effectively measuring the weight of the liquid above the pressure sensor. In one embodiment the pressure sensor is placed at the lowermost portion of the medication bowl. On addition of liquid into the nebulizer, the pressure sensor is covered by the liquid and registers an increase in pressure due to the weight of the liquid directly above it. As the medication is aerosolized the amount of liquid above the sensor decreases and the sensor registers a lower pressure. This method is not limited to the use of a single sensor as an addition sensor may be added to monitor atmospheric pressure. As with the other fluid level measurements, this method requires the liquid to be still with an unmoving surface and is unable to account for liquid hang-ups on the internal surfaces of the device. A load cell would accomplish the same task as the pressure sensor.

Permittivity of Light

Referring to FIG. 89, the fluid level may be estimated by evaluating the permittivity of light through the liquid. A light source 108 may be positioned above the maximum fluid level with a sensor 106 positioned at the bottom of the bowl. Alternatively, the light source may be placed within the medication bowl and the sensor placed above the maximum fill marker. In the absence of medication the sensor registers maximum light intensity as light is able to travel from the source to sensor with minimal diffraction. On addition of the medication, light is refracted by the liquid and a lower intensity is registered. An increase in the amount of liquid between the source and sensor may decrease the light intensity further and can be related to medication volume experimentally. This embodiment and method is not limited to using a single wavelength or even by the visible spectrum.

Parallel Conductive Strips

Referring to FIG. 90, a number of parallel conductive strips 292 can be placed on the internal surface of the medication bowl with known distances between each strip. A microcontroller can be used to monitor the resistances between or to each conductive strip. If all conductive strips are initially covered by the liquid there would be a low resistance between different strips. As the liquid level lowers and uncovers a strip this will register as a high impedance, potentially an open circuit, as the current can no longer easily flow back to ground. This will give an approximate fluid level height based on the number of conductive strips that are exposed to and the known distances between strips. In one embodiment, the conductive strips are placed to correspond with existing fill volume lines on the nebulizer.

Time of Flight

Referring to FIG. 91, a transducer and receiver 174, 176 may be placed above the fluid such that on creation of a pulse, the pulse will reflect off the fluid surface and back at the receiver. Based on the time it take for the pulse to travel from the transducer, reflect off of the surface and travel back to the receiver the distance of the sensors to the fluid level can be calculated and the fluid level deduced from this. This method is not limited to ultrasonic waves and can use any frequency.

Image Processing

Referring to FIG. 92, an image of the fluid level relative to a known marker may be captured and analyzed by a microcontroller to determine the fluid level in the nebulizer bowl. This can be done by counting the pixels between the marker and the fluid level or by comparing the image to a database of images with known volumes and selecting the fluid level with the highest correlation coefficient. This is not limited to using an internal camera 294 and an external camera such as a smartphones may be used and the images communicated to the smart nebulizer.

Light Curtain

Referring to FIG. 93, as with Activation Detection using a light curtain, a single light source or multiple light sources 108 may be placed such that multiple light detectors 106 are placed opposite of them with an air gap between them where medication fills. Similar to the Light Permittivity method, as fluid passes between the sensors and the light source a reduced intensity of light is detected as more light is reflected or diffracted away from the sensor, By knowing the spacing of the detectors the fluid level may be estimated. Alternatively, multiple light sources could be used and a single detector. When no medication is in the nebulizer a maximum light intensity is measured. As medication covers the light sources, less light is detected.

Weight of Device

Figure 95:
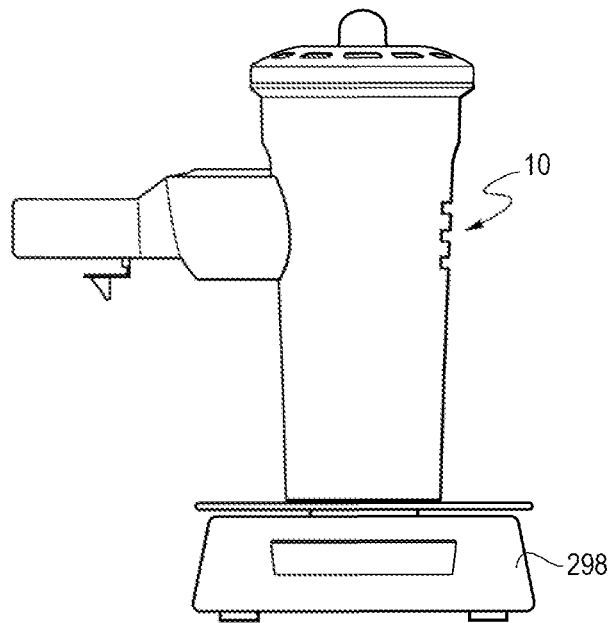
FIG. 95 is a view of a nebulizer and scale.

Referring to FIG. 95, measuring the weight of the device with a scale 298 is one way of determining the residual volume if the initial weight of the device is already known as well as the density of the medication. In most cases it may be acceptable to approximate the density to be that of water. This method of determining residual volume is advantageous as it is not affected by the liquid hang-up within the device. In one embodiment a scale is used to measure the device before medication is added, after medication is added and after treatment is complete. The scale could be a standalone device that is capable of communicating with the smart nebulizer system. The measurement from the scale readout could also be manually input into the smart nebulizer system by the patient. In addition, many currently available smart phones have pressure sensitive displays that could calculate the weight of the nebulizer based on the measured pressure and the surface area in contact with the screen.

Figure 96:
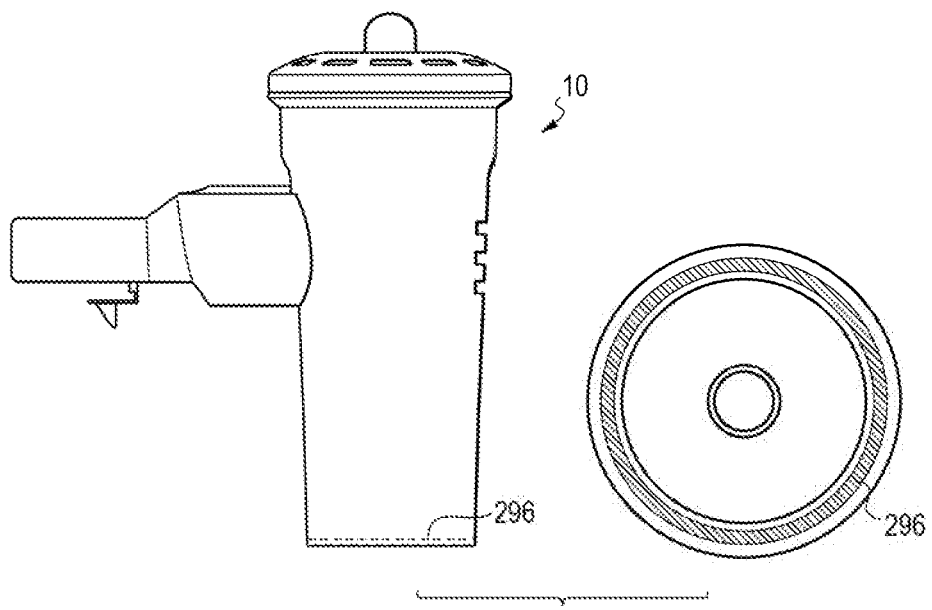
FIG. 96 are side and bottom views of one embodiment of a nebulizer.
Figure 100:
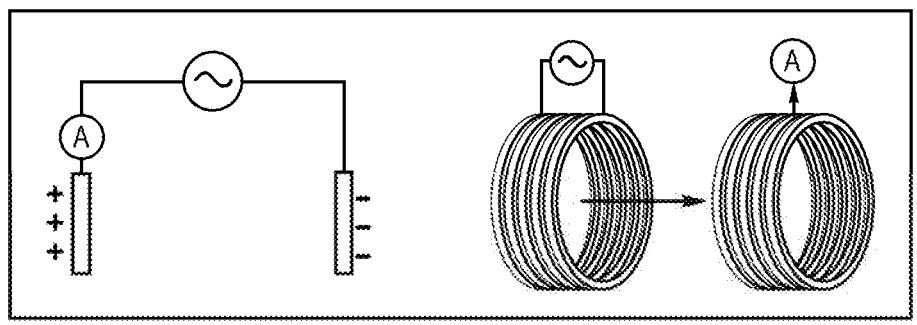
FIG. 100 is a view of a conductivity arrangement for concentration determination.

In another embodiment, shown in FIG. 96, a pressure sensitive surface or load cell 296 is incorporated into the bottom surface of the nebulizer. When the nebulizer is placed on a flat surface the sensors registers the weight of the nebulizer and communicates this information back to a central control unit.

Communication and Data Processing

In order to provide faster and more accurate processing of the sensor data generated within the smart nebulizer, data may be wirelessly communicated to a smart phone, local computing device and/or remote computing device to interpret and act on the raw sensor data.

In one implementation, the smart nebulizer includes circuitry for transmitting raw sensor data in real time to a local device, such as a smart phone. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the smart nebulizer.

In addition to simply presenting data, statistics or instructions on a display of the smart phone or other local computer in proximity of the smart nebulizer, proactive operations relating to the smart nebulizer may be actively managed and controlled. For example, if the smart phone or other local computer in proximity to the smart nebulizer determines that the sensor data indicates the end of treatment has been reached, the smart phone or other local computing device may communicate directly with a pressurized gas line relay associated with the gas supply to the smart nebulizer to shut down the supply of gas. Other variations are also contemplated, for example where a remote server in communication with the smart phone, or in direct communication with the smart nebulizer via a communication network, can make the decision to shut down the pressurized gas supply to the smart nebulizer when an end of treatment status is determined.

In yet other implementations, real-time data gathered in the smart nebulizer and relayed via to the smart phone to the remote server may trigger the remote server to track down and notify a physician or supervising caregiver regarding a problem with the particular nebulization session or a pattern that has developed over time based on past nebulization sessions for the particular user. Based on data from the one or more sensors in the smart nebulizer, the remote server may generate alerts to send via text, email or other electronic communication medium to the user's physician or other caregiver.

The electronic circuitry in the smart nebulizer, the local computing device and/or the remote server discussed above, may include some or all of the capabilities of a computer 500 in communication with a network 526 and/or directly with other computers. As illustrated in FIG. 5, the computer 500 may include a processor 502, a storage device 516, a display or other output device 510, an input device 512, and a network interface device 520, all connected via a bus 508. The computer may communicate with the network The processor 502 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor 502 executes instructions and includes that portion of the computer 500 that controls the operation of the entire computer. Although not depicted in FIG. 6, the processor 502 typically includes a control unit that organizes data and program storage in memory and transfers data and other information between the various parts of the computer 500. The processor 502 receives input data from the input device 512 and the network 526 reads and stores instructions (for example processor executable code) 524 and data in the main memory 504, such as random access memory (RAM), static memory 506, such as read only memory (ROM), and the storage device 516. The processor 502 may present data to a user via the output device 510.

Although the computer 500 is shown to contain only a single processor 502 and a single bus 508, the disclosed embodiment applies equally to computers that may have multiple processors and to computers that may have multiple busses with some or all performing different functions in different ways.

The storage device 516 represents one or more mechanisms for storing data. For example, the storage device 516 may include a computer readable medium 522 such as read-only memory (ROM), RAM, non-volatile storage media, optical storage media, flash memory devices, and/or other machine-readable media. In other embodiments, any appropriate type of storage device may be used. Although only one storage device 516 is shown, multiple storage devices and multiple types of storage devices may be present. Further, although the computer 500 is drawn to contain the storage device 516, it may be distributed across other computers, for example on a server.

The storage device 516 may include a controller (not shown) and a computer readable medium 522 having instructions 524 capable of being executed on the processor 502 to carry out the functions described above with reference to processing sensor data, displaying the sensor data or instructions based on the sensor data, controlling aspects of the smart nebulizer to alter its operation, or contacting third parties or other remotely located resources to provide update information to, or retrieve data from those remotely located resources. In another embodiment, some or all of the functions are carried out via hardware in lieu of a processor-based system. In one embodiment, the controller is a web browser, but in other embodiments the controller may be a database system, a file system, an electronic mail system, a media manager, an image manager, or may include any other functions capable of accessing data items. The storage device 516 may also contain additional software and data (not shown), which is not necessary to understand the invention.

The output device 510 is that part of the computer 500 that displays output to the user. The output device 510 may be a liquid crystal display (LCD) well-known in the art of computer hardware. In other embodiments, the output device 510 may be replaced with a gas or plasma-based flat-panel display or a traditional cathode-ray tube (CRT) display. In still other embodiments, any appropriate display device may be used. Although only one output device 510 is shown, in other embodiments any number of output devices of different types, or of the same type, may be present. In an embodiment, the output device 510 displays a user interface. The input device 512 may be a keyboard, mouse or other pointing device, trackball, touchpad, touch screen, keypad, microphone, voice recognition device, or any other appropriate mechanism for the user to input data to the computer 500 and manipulate the user interface previously discussed. Although only one input device 512 is shown, in another embodiment any number and type of input devices may be present.

The network interface device 520 provides connectivity from the computer 500 to the network 526 through any suitable communications protocol. The network interface device 520 sends and receives data items from the network 526 via a wireless or wired transceiver 514. The transceiver 514 may be a cellular frequency, radio frequency (RF), infrared (IR) or any of a number of known wireless or wired transmission systems capable of communicating with a network 526 or other smart devices 102 having some or all of the features of the example computer of FIG. 2. The bus 508 may represent one or more busses, e.g., USB, PCI, ISA (Industry Standard Architecture), X-Bus, EISA (Extended Industry Standard Architecture), or any other appropriate bus and/or bridge (also called a bus controller).

The computer 500 may be implemented using any suitable hardware and/or software, such as a personal computer or other electronic computing device. The computer 500 may be a portable computer, laptop, tablet or notebook computers, smart phones, PDAs, pocket computers, appliances, telephones, and mainframe computers are examples of other possible configurations of the computer 500. The network 526 may be any suitable network and may support any appropriate protocol suitable for communication to the computer 500. In an embodiment, the network 526 may support wireless communications. In another embodiment, the network 526 may support hard-wired communications, such as a telephone line or cable. In another embodiment, the network 526 may support the Ethernet IEEE (Institute of Electrical and Electronics Engineers) 802.3x specification. In another embodiment, the network 526 may be the Internet and may support IP (Internet Protocol). In another embodiment, the network 526 may be a LAN or a WAN. In another embodiment, the network 526 may be a hotspot service provider network. In another embodiment, the network 526 may be an intranet. In another embodiment, the network 526 may be a GPRS (General Packet Radio Service) network. In another embodiment, the network 526 may be any appropriate cellular data network or cell-based radio network technology. In another embodiment, the network 526 may be an IEEE 802.11 wireless network. In still another embodiment, the network 526 may be any suitable network or combination of networks. Although one network 526 is shown, in other embodiments any number of networks (of the same or different types) may be present.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or use the processes described in connection with the presently disclosed subject matter, e.g., through the use of an API, reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations. Although exemplary embodiments may refer to using aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be spread across a plurality of devices. Such devices might include personal computers, network servers, and handheld devices, for example.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A nebulizer system comprising:
   a nebulizer comprising a housing having an ambient air inlet, a chamber for holding an aerosol, a medication reservoir, a pressurized gas inlet in flow communication with the chamber, and an air outlet communicating with the chamber for permitting the aerosol to be withdrawn from the chamber;
   an activation detector coupled to the nebulizer and operable to detect an activation of the nebulizer;
   a flow detector coupled to the nebulizer and operable to detect an inhalation flow rate through the chamber;
   an air supply detector coupled to the nebulizer and operable to identify a pressure and/or flow rate of a pressurized gas supply coupled to the pressurized gas inlet of the nebulizer;
   a feedback device configured to provide feedback to a user about the inhalation flow rate in real time; and a controller operably connected with the activation detector, flow detector, air supply detector and feedback device, wherein the controller receives input from the activation detector, air supply detector and flow detector and signals the feedback device to provide feedback about an upper inhalation flow rate limit and/or a lower inhalation flow rate limit in real time such that the inhalation flow rate may be adjusted and maintained between the upper inhalation flow rate limit and the lower inhalation flow rate limit in real time, and wherein the controller receives input from the activation detector, air supply detector and flow detector and wherein the controller is configured to calculate a respirable dose of medication based on the received input from the activation detector, air supply detector and flow detector.

2. The nebulizer system of claim 1 further comprising a medication identifier coupled to the nebulizer and operable to identify a type of medication introduced into the medication reservoir.

3. The nebulizer system of claim 1 further comprising a concentration detector coupled to the nebulizer and operable to identify a concentration of a liquid medication disposed in the medication reservoir.

4. The nebulizer system of claim 1 further comprising a particle size detector coupled to the nebulizer and operable to measure a particle size distribution of an aerosolized medication in the chamber.

5. The nebulizer system of claim 4 wherein the particle size detector comprises a light source and a light detector spaced apart from the light source.

6. The nebulizer system of claim 5 further comprising a Fourier lens disposed between the light source and the detector.

7. The nebulizer system of claim 4 wherein the nebulizer comprises a baffle spaced apart from an orifice of the gas inlet, and wherein the particle size detector comprises a force or pressure sensor operably coupled to the baffle.

8. The nebulizer system of claim 1 further comprising an end of treatment detector coupled to the nebulizer and connected to the controller, wherein the controller is operable to notify the user via the feedback device when an end of treatment has been reached.

9. The nebulizer system of claim 8 further comprising a residual volume detector coupled to the nebulizer and connected to the controller, wherein the controller is operable to notify the user via the feedback device of a residual volume of medication when end of treatment has been reached.

10. The nebulizer system of claim 9 wherein the residual volume detector comprises a capacitive sensor operably coupled to the reservoir.

11. The nebulizer system of claim 9 wherein the residual volume detector comprises a moveable floating element disposed in the reservoir and a stationary sensing unit operable to sense the position of the floating element.

12. The nebulizer system of claim 9 wherein the residual volume detector comprises a pressure sensor coupled to the reservoir.

13. The nebulizer system of claim 9 wherein the residual volume detector comprises a light source and a light detector spaced apart from the light source, wherein one of the light source and light detector is disposed in the reservoir.

14. The nebulizer system of claim 9 wherein the residual volume detector comprises a plurality of spaced apart conductive strips disposed along an interior surface of the reservoir.

15. The nebulizer system of claim 9 wherein the residual volume detector comprises a transducer and a receiver spaced above a bottom of the reservoir.

16. The nebulizer system of claim 9 wherein the residual volume detector comprises a camera directed toward the reservoir.

17. The nebulizer system of claim 8 wherein the end of treatment detector comprises a microphone operable to detect a sputter caused by gaps in fluid flow.

18. The nebulizer system of claim 8 wherein the nebulizer comprises a baffle spaced apart from an orifice of the gas inlet, and wherein the end of treatment detector comprises a force or pressure sensor operably coupled to the baffle.

19. The nebulizer system of claim 1 wherein the feedback device is operable to communicate the respirable dose administered to the user.

20. The nebulizer system of claim 1 further comprising storage operable to log treatment occurrences.

21. The nebulizer system of claim 1 wherein the feedback comprises at least one of a visual, auditory and/or vibratory feedback.

22. The nebulizer system of claim 1 further comprising an actuator coupled to a biasing diaphragm, wherein the actuator and biasing diaphragm are coaxially positioned in the nebulizer, and wherein the actuator is configured to move between a non-nebulizing position and a nebulizing position, and wherein the biasing diaphragm assists in the movement of the actuator between the non-nebulizing position when no inhalation is occurring and the nebulizing position when inhalation is occurring.

23. A nebulizer system comprising:
a nebulizer comprising a housing having an ambient air inlet, a chamber for holding an aerosol, a medication reservoir and an air outlet communicating with the chamber for permitting the aerosol to be withdrawn from the chamber;
means for detecting an activation of the nebulizer; and
means for identifying a pressure of a pressurized gas supply coupled to the nebulizer;
means for detecting an inhalation flow rate through the chamber;
means for providing feedback to a user about the inhalation flow rate in real time; and
a controller operably connected with the means for detecting the activation, means for identifying the pressure and means for detecting the inhalation flow rate, wherein the controller receives input from the means for detecting the activation, the means for identifying the pressure and the means for detecting the inhalation flow rate, and signals the means for providing feedback to provide feedback about an upper inhalation flow rate limit and/or a lower inhalation flow rate limit in real time such that the inhalation flow rate may be adjusted and maintained between the upper inhalation flow rate limit and the lower inhalation flow rate limit in real time, and wherein the controller receives input from the means for detecting the activation, the means for identifying the pressure and the means for detecting the inhalation flow rate and is configured to calculate a respirable dose of medication based on the received input from the means for detecting the activation, the means for identifying the pressure and the means for detecting the inhalation flow rate.

24. The nebulizer system of claim 23 further comprising means for identifying a type of medication introduced into the medication reservoir.

25. The nebulizer system of claim 23 further comprising means for identifying the concentration of a liquid medication disposed in the medication reservoir.

26. The nebulizer system of claim 23 further comprising means for measuring a particle size distribution of an aerosolized medication in the chamber.

27. The nebulizer system of claim 26 wherein the means for measuring comprises a light source and a light detector spaced apart from the light source.

28. The nebulizer system of claim 27 further comprising a Fourier lens disposed between the light source and the detector.

29. The nebulizer system of claim 26 wherein the nebulizer comprises a baffle spaced apart from an orifice of the gas inlet, and wherein the means for measuring comprises a force or pressure sensor operably coupled to the baffle.

30. The nebulizer system of claim 23 further comprising means for notifying the user when an end of treatment has been reached.

31. The nebulizer system of claim 30 wherein the means for notifying comprises a microphone operable to detect a sputter caused by gaps in fluid flow.

32. The nebulizer system of claim 30 wherein the nebulizer comprises a baffle spaced apart from an orifice of a gas inlet, and wherein the means for notifying comprises a force or pressure sensor operably coupled to the baffle.

33. The nebulizer system of claim 23 further comprising means for notifying the user of a residual volume of medication when end of treatment has been reached.

34. The nebulizer system of claim 33 wherein the means for notifying comprises a capacitive sensor operably coupled to the reservoir.

35. The nebulizer system of claim 33 wherein the means for notifying comprises a moveable floating element disposed in the reservoir and a stationary sensing unit operable to sense the position of the floating element.

36. The nebulizer system of claim 33 wherein the means for notifying comprises a pressure sensor coupled to the reservoir.

37. The nebulizer system of claim 33 wherein the means for notifying comprises a light source and a light detector spaced apart from the light source, wherein one of the light source and light detector is disposed in the reservoir.

38. The nebulizer system of claim 33 wherein the means for notifying comprises a plurality of spaced apart conductive strips disposed along an interior surface of the reservoir.

39. The nebulizer system of claim 33 wherein the means for notifying comprises a transducer and a receiver spaced above a bottom of the reservoir.

40. The nebulizer system of claim 33 wherein the means for notifying comprises a camera directed toward the reservoir.

41. The nebulizer system of claim 23 wherein the nebulizer further comprises a pressurized gas inlet in flow communication with the chamber.

42. The nebulizer system of claim 23 further comprising an actuator coupled to a biasing diaphragm, wherein the actuator and biasing diaphragm are coaxially positioned in the nebulizer, and wherein the actuator is configured to move between a non-nebulizing position and a nebulizing position, and wherein the biasing diaphragm assists in the movement of the actuator between the non-nebulizing position when no inhalation is occurring and the nebulizing position when inhalation is occurring.

* * * * *